(12) United States Patent
Schotte et al.

(10) Patent No.: US 12,116,607 B2
(45) Date of Patent: Oct. 15, 2024

(54) METHOD FOR THE PRODUCTION OF DOMAIN ANTIBODIES

(71) Applicant: Ablynx N.V., Zwijnaarde (BE)

(72) Inventors: Peter Schotte, De Pinte (BE); Patrick Stanssens, Nazareth (BE); Christine Labeur, Bruges (BE); Jean-Luc Jonniaux, Tienen (BE); Marc Jozef Lauwereys, Haaltert (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 747 days.

(21) Appl. No.: 15/254,027

(22) Filed: Sep. 1, 2016

(65) Prior Publication Data

US 2017/0081692 A1    Mar. 23, 2017

Related U.S. Application Data

(63) Continuation of application No. 13/266,503, filed as application No. PCT/EP2010/055916 on Apr. 30, 2010, now Pat. No. 9,464,138.

(60) Provisional application No. 61/304,834, filed on Feb. 16, 2010, provisional application No. 61/174,184, filed on Apr. 30, 2009.

(51) Int. Cl.
| | |
|---|---|
| *C12P 21/00* | (2006.01) |
| *C07K 16/00* | (2006.01) |
| *C07K 16/18* | (2006.01) |
| *C07K 16/28* | (2006.01) |

(52) U.S. Cl.
CPC ............ *C12P 21/005* (2013.01); *C07K 16/00* (2013.01); *C07K 16/18* (2013.01); *C07K 16/2875* (2013.01); *C07K 2317/14* (2013.01); *C07K 2317/24* (2013.01); *C07K 2317/35* (2013.01); *C07K 2317/56* (2013.01); *C07K 2317/569* (2013.01); *C07K 2317/624* (2013.01); *C07K 2317/626* (2013.01)

(58) Field of Classification Search
None
See application file for complete search history.

(56) References Cited

U.S. PATENT DOCUMENTS

| 4,572,798 | A | | 2/1986 | Koths et al. | |
|---|---|---|---|---|---|
| 5,122,469 | A | * | 6/1992 | Mather ................ | C12N 5/0037 435/383 |
| 9,464,138 | B2 | | 10/2016 | Schotte et al. | |
| 2007/0059304 | A1 | * | 3/2007 | Cho et al. .......... | C07K 16/2863 424/143.1 |
| 2009/0053786 | A1 | * | 2/2009 | Kao et al. ................ | C12N 1/38 435/184 |

FOREIGN PATENT DOCUMENTS

| WO | WO 2004/041863 A2 | 5/2004 |
|---|---|---|
| WO | WO 2006/047340 A2 | 5/2006 |
| WO | WO 2006/138737 A2 | 12/2006 |
| WO | WO 2007/136463 A2 | 11/2007 |
| WO | WO 2008/127305 A2 | 10/2008 |
| WO | WO 2008/142164 A2 | 11/2008 |
| WO | WO 2009/009523 A2 | 1/2009 |

OTHER PUBLICATIONS

Spinelli, Silvia, et al. "Lateral recognition of a dye hapten by a llama VHH domain." Journal of molecular biology 311.1 (2001): 123-129. (Year: 2001).*
Frenken, Leon GJ, et al. "Isolation of antigen specific llama VHH antibody fragments and their high level secretion by *Saccharomyces cerevisiae*." Journal of biotechnology 78.1 (2000): 11-21. (Year: 2000).*
Klooster, Rinse, et al. "Improved anti-IgG and HSA affinity ligands: clinical application of VHH antibody technology." Journal of immunological methods 324.1-2 (2007): 1-12. (Year: 2007).*
Muyldermans, Serge. "Single domain camel antibodies: current status." Reviews in molecular Biotechnology 74.4 (2001): 277-302. (Year: 2001).*
Bazl, M. Rajabi, et al. "Production of Chimeric Recombinant Single Domain Antibody—Green Fluorescent Fusion Protein in Chinese Hamster Ovary Cells." Hybridoma 26.1 (2007): 1-9. (Year: 2007).*
Rahbarizadeh, Fatemeh, et al. "Over expression of anti-MUC1 single-domain antibody fragments in the yeast *Pichia pastoris*." Molecular immunology 43.5 (2006): 426-435. (Year: 2006).*
Atwood et al., Copper mediates dityrosine cross-linking of Alzheimer's amyloid-beta. Biochemistry. Jan. 20, 2004;43(2):560-8.
Borth et al., Effect of increased expression of protein disulfide isomerase and heavy chain binding protein on antibody secretion in a recombinant CHO cell line. Biotechnol Prog. Jan. 2005 Feb.;21(1):106-11.
Chaderjian et al., Effect of copper sulfate on performance of a serum-free CHO cell culture process and the level of free thiol in the recombinant antibody expressed. Biotechnol Prog. Mar.-Apr. 2005;21(2):550-3.
Cooper, Biochemistry of sulfur-containing amino acids. Annu Rev Biochem. 1983;52:187-222. Review. Abstract only.
Damasceno et al., Cooverexpression of chaperones for enhanced secretion of a single-chain antibody fragment in Pichia pastoris. Appl Microbiol Biotechnol. Feb. 2007;74(2):381-9. Epub Oct. 19, 2006.
Gasser et al., Antibody production with yeasts and filamentous fungi: on the road to large scale? Biotechnol Lett. Feb. 2007;29(2):201-12. Epub Nov. 22, 2006.
Gasser et al., Engineering of Pichia pastoris for improved production of antibody fragments. Biotechnol Bioeng. Jun. 5, 2006;94(2):353-61.

(Continued)

*Primary Examiner* — Robert J Yamasaki
(74) *Attorney, Agent, or Firm* — Wolf, Greenfield & Sacks, P.C.

(57) ABSTRACT

The present invention relates to a method for producing a domain antibody in a yeast, wherein the formation of disulfide bridges in the domain antibody is promoted. The method encompasses the addition of oxidizing agents, preferably oxidizing metal ions, preferably one or more selected from $Cu^{2+}$, $Fe^{2+}$, $Fe^{3+}$ and $Zn^{2+}$.

17 Claims, 21 Drawing Sheets

Specification includes a Sequence Listing.

(56) References Cited

OTHER PUBLICATIONS

Gasser et al., Transcriptomics-based identification of novel factors enhancing heterologous protein secretion in yeasts. Appl Environ Microbiol. Oct. 2007;73(20):6499-507. Epub Aug. 31, 2007.

Hackel et al., Production of soluble and active transferrin receptor-targeting single-chain antibody using Saccharomyces cerevisiae. Pharm Res. Apr. 2006;23(4):790-7. Epub Mar. 25, 2006.

Harmsen et al., Llama heavy-chain V regions consist of at least four distinct subfamilies revealing novel sequence features. Mol Immunol. Aug. 2000;37(10):579-90.

Harmsen et al., Properties, production, and applications of camelid single-domain antibody fragments. Appl Microbiol Biotechnol. Nov. 2007;77(1):13-22. Epub Aug. 18, 2007. Review.

Holt et al., Domain antibodies: proteins for therapy. Trends Biotechnol. Nov. 2003;21(11):484-90.

Hsu et al., Rescue of immunoglobulins from insolubility is facilitated by PDI in the baculovirus expression system. Protein Expr Purif. May 1996;7(3):281-8.

Humphreys et al., Co-expression of human protein disulphide isomerase (PDI) can increase the yield of an antibody Fab' fragment expressed in *Escherichia coli*. FEBS Lett. Feb. 12, 1996;380(1-2):194-7.

Kajino et al., A protein disulfide isomerase gene fusion expression system that increases the extracellular productivity of Bacillus brevis. Appl Environ Microbiol. Feb. 2000;66(2):638-42.

Kimura et al., Interactions among yeast protein-disulfide isomerase proteins and endoplasmic reticulum chaperone proteins influence their activities. J Biol Chem. Sep. 9, 2005;280(36):31438-41. Epub Jul. 7, 2005.

Lilie et al., Influence of protein disulfide isomerase (PDI) on antibody folding in vitro. J Biol Chem. May 13, 1994;269(19):14290-6.

Mayer et al., Influence of the oxidoreductase ER57 on the folding of an antibody fab fragment. J Mol Biol. Aug. 20, 2004;341(4):1077-84.

Mayer et al., BiP and PDI cooperate in the oxidative folding of antibodies in vitro. J Biol Chem. Sep. 22, 2000;275(38):29421-5.

Merk et al., Cell-free expression of two single-chain monoclonal antibodies against lysozyme: effect of domain arrangement on the expression. J Biochem. Feb. 1999;125(2):328-33.

Mohan et al., Effect of doxycycline-regulated protein disulfide isomerase expression on the specific productivity of recombinant CHO cells: thrombopoietin and antibody. Biotechnol Bioeng. Oct. 15, 2007;98(3):611-5.

Nilsson et al., Differentiation-associated redox-regulation in human B cell lines from stem cell/pro-B to plasma cell. Immunol Lett. Jun. 15, 2004;94(1-2):83-9.

Pal et al., SCFCdc4-mediated degradation of the Hac1p transcription factor regulates the unfolded protein response in *Saccharomyces cerevisiae*. Mol Biol Cell. Feb. 2007;18(2):426-40. Epub Nov. 15, 2006.

Petersen et al., An in vitro system for studying the kinetics of interchain disulfide bond formation in immunoglobulin G. J Biol Chem. Sep. 10, 1974;249(17):5633-41.

Rahbarizadeh et al., Over expression of anti-MUC1 single-domain antibody fragments in the yeast *Pichia pastoris*. Mol Immunol. Feb. 2006;43(5):426-35. Epub Mar. 25, 2005.

Ryabova et al., Functional antibody production using cell-free translation: effects of protein disulfide isomerase and chaperones. Nat Biotechnol. Jan. 1997;15(1):79-84.

Shusta et al., Increasing the secretory capacity of *Saccharomyces cerevisiae* for production of single-chain antibody fragments. Nat Biotechnol. Aug. 1998;16(8):773-7.

Stadtman, Metal ion-catalyzed oxidation of proteins: biochemical mechanism and biological consequences. Free Radic Biol Med. 1990;9(4):315-25. Review. Erratum in: Free Radic Biol Med 1991;10(3-4):249.

Thomassen et al., Specific production rate of VHH antibody fragments by *Saccharomyces cerevisiae* is correlated with growth rate, independent of nutrient limitation. J Biotechnol. Aug. 22, 2005;118(3):270-7.

Van De Laar et al., Increased heterologous protein production by *Saccharomyces cerevisiae* growing on ethanol as sole carbon source. Biotechnol Bioeng. Feb. 15, 2007;96(3):483-94.

Vinci et al., Hierarchical formation of disulfide bonds in the immunoglobulin Fc fragment is assisted by protein-disulfide isomerase. J Biol Chem. Apr. 9, 2004;279(15):15059-66. Epub Jan. 17, 2004.

Whiteley et al., Thioredoxin domain non-equivalence and antichaperone activity of protein disulfide isomerase mutants in vivo. J Biol Chem. Sep. 5, 1997;272(36):22556-63.

Wilkinson et al., A structural disulfide of yeast protein-disulfide isomerase destabilizes the active site disulfide of the N-terminal thioredoxin domain. J Biol Chem. Mar. 25, 2005;280(12):11483-7. Epub Jan. 13, 2005.

Xu et al., Analysis of unfolded protein response during single-chain antibody expression in *Saccaromyces cerevisiae* reveals different roles for BiP and PDI in folding. Metab Eng. Jul. 2005;7(4):269-79.

PCT/EP2010/055916, Nov. 30, 2010, International Search Report and Written Opinion.

PCT/EP2010/055916, Nov. 10, 2011, International Preliminary Report on Patentability.

EP 15174570.0, Sep. 19, 2019, Third Party Observations.

[No Author Listed] Pichia Fermentation Process Guidelines. Invitrogen Life Technologies. Version B 053002. 2002. 11 pages.

Third Party Observations under Art 115 EPC European Patent Application No. 15174570 (EP2982690) in the name of Ablynx N.V., mailed Sep. 19, 2019.

Communication pursuant to Rule 114(2) EPC for Application No. EP 15174570.0, mailed Oct. 29, 2020.

Firer et al., Efficient elution of functional proteins in affinity chromatography. J Biochem Biophys Methods. Oct. 30, 2001;49(1-3):433-42. doi: 10.1016/s0165-022x(01)00211-1.

[No Author Listed], Annex—calculation of the amount of Cu2+, Fe2+, and Zn2+ ions present at different stages of the fermentation process described in section 2.6 of D2. No date. 3 pages. D2 corresponds to "Thomassen et al., Large-Scale production of VHH antibody fragments by *Saccharomyces cerevisiae*. Enzyme Microbial Technol. 2002;30:273-278."

[No Author Listed], Thioredoxin-1. Uniprot Accession No. P22217. Jan. 8, 1991. 5 pages.

Chisti, Strategies in downstream processing. From Bioseparation and Bioprocessing: A Handbook. Wiley-VCH. 1998;2:3-30.

Cregg, Chapter 4: Rational Design and Optimization of Fed-Batch and Continuous Fermentations. From Methods in Molecular Biology. Pichia Protocols. 2007;389:43-63. 32 pages.

Holliger et al., Engineered antibody fragments and the rise of single domains. Nat Biotechnol. Sep. 2005;23(9):1126-36. doi: 10.1038/nbt1142.

Price et al., Effect of divalent cations on the reduction and re-formation of the disulfide bonds of deoxyribonuclease. J Biol Chem. Feb. 10, 1969;244(3):929-32.

Thomassen et al., Large-scale production of VHH antibody fragments by *Saccharomyces cerevisiae*. Enzyme and Microbial Technol. 2002;30:273-278.

\* cited by examiner

SEQUENCE LISTING

<160> NUMBER OF SEQ ID NOS: 13

<210> SEQ ID NO 1
<211> LENGTH: 28
<212> TYPE: DNA
<213> ORGANISM: Artificial Sequence
<220> FEATURE:
<223> OTHER INFORMATION: Primer

<400> SEQUENCE: 1
gaattcatga agttttctgc tggtgccg                                    28

<210> SEQ ID NO 2
<211> LENGTH: 37
<212> TYPE: DNA
<213> ORGANISM: Artificial Sequence
<220> FEATURE:
<223> OTHER INFORMATION: Primer

<400> SEQUENCE: 2
ctcgagttac aattcatcgt gaatggcatc ttcttcg                          37

<210> SEQ ID NO 3
<211> LENGTH: 522
<212> TYPE: PRT
<213> ORGANISM: Saccharomyces cerevisiae

<400> SEQUENCE: 3

Met Lys Phe Ser Ala Gly Ala Val Leu Ser Trp Ser Ser Leu Leu Leu
1               5                   10                  15

Ala Ser Ser Val Phe Ala Gln Gln Glu Ala Val Ala Pro Glu Asp Ser
                20                  25                  30

Ala Val Val Lys Leu Ala Thr Asp Ser Phe Asn Glu Tyr Ile Gln Ser
            35                  40                  45

His Asp Leu Val Leu Ala Glu Phe Phe Ala Pro Trp Cys Gly His Cys
        50                  55                  60

Lys Asn Met Ala Pro Glu Tyr Val Lys Ala Ala Glu Thr Leu Val Glu
65                  70                  75                  80

Lys Asn Ile Thr Leu Ala Gln Ile Asp Cys Thr Glu Asn Gln Asp Leu
                85                  90                  95

Cys Met Glu His Asn Ile Pro Gly Phe Pro Ser Leu Lys Ile Phe Lys
            100                 105                 110

Asn Ser Asp Val Asn Asn Ser Ile Asp Tyr Glu Gly Pro Arg Thr Ala
        115                 120                 125

Glu Ala Ile Val Gln Phe Met Ile Lys Gln Ser Gln Pro Ala Val Ala
    130                 135                 140

Val Val Ala Asp Leu Pro Ala Tyr Leu Ala Asn Glu Thr Phe Val Thr
145                 150                 155                 160

Pro Val Ile Val Gln Ser Gly Lys Ile Asp Ala Asp Phe Asn Ala Thr
                165                 170                 175

Phe Tyr Ser Met Ala Asn Lys His Phe Asn Asp Tyr Asp Phe Val Ser
            180                 185                 190

Ala Glu Asn Ala Asp Asp Asp Phe Lys Leu Ser Ile Tyr Leu Pro Ser
        195                 200                 205

Ala Met Asp Glu Pro Val Val Tyr Asn Gly Lys Lys Ala Asp Ile Ala

```
                210                 215                 220
Asp Ala Asp Val Phe Glu Lys Trp Leu Gln Val Glu Ala Leu Pro Tyr
225                 230                 235                 240

Phe Gly Glu Ile Asp Gly Ser Val Phe Ala Gln Tyr Val Glu Ser Gly
            245                 250                 255

Leu Pro Leu Gly Tyr Leu Phe Tyr Asn Asp Glu Glu Leu Glu Glu
            260                 265                 270

Tyr Lys Pro Leu Phe Thr Glu Leu Ala Lys Lys Asn Arg Gly Leu Met
            275                 280                 285

Asn Phe Val Ser Ile Asp Ala Arg Lys Phe Gly Arg His Ala Gly Asn
            290                 295                 300

Leu Asn Met Lys Glu Gln Phe Pro Leu Phe Ala Ile His Asp Met Thr
305                 310                 315                 320

Glu Asp Leu Lys Tyr Gly Leu Pro Gln Leu Ser Glu Glu Ala Phe Asp
                325                 330                 335

Glu Leu Ser Asp Lys Ile Val Leu Glu Ser Lys Ala Ile Glu Ser Leu
                340                 345                 350

Val Lys Asp Phe Leu Lys Gly Asp Ala Ser Pro Ile Val Lys Ser Gln
                355                 360                 365

Glu Ile Phe Glu Asn Gln Asp Ser Ser Val Phe Gln Leu Val Gly Lys
                370                 375                 380

Asn His Asp Glu Ile Val Asn Asp Pro Lys Lys Asp Val Leu Val Leu
385                 390                 395                 400

Tyr Tyr Ala Pro Trp Cys Gly His Cys Lys Arg Leu Ala Pro Thr Tyr
                405                 410                 415

Gln Glu Leu Ala Asp Thr Tyr Ala Asn Ala Thr Ser Asp Val Leu Ile
                420                 425                 430

Ala Lys Leu Asp His Thr Glu Asn Asp Val Arg Gly Val Val Ile Glu
                435                 440                 445

Gly Tyr Pro Thr Ile Val Leu Tyr Pro Gly Gly Lys Lys Ser Glu Ser
                450                 455                 460

Val Val Tyr Gln Gly Ser Arg Ser Leu Asp Ser Leu Phe Asp Phe Ile
465                 470                 475                 480

Lys Glu Asn Gly His Phe Asp Val Asp Gly Lys Ala Leu Tyr Glu Glu
                485                 490                 495

Ala Gln Glu Lys Ala Ala Glu Glu Ala Asp Ala Asp Ala Glu Leu Ala
                500                 505                 510

Asp Glu Glu Asp Ala Ile His Asp Glu Leu
                515                 520

<210> SEQ ID NO 4
<211> LENGTH: 259
<212> TYPE: PRT
<213> ORGANISM: Artificial Sequence
<220> FEATURE:
<223> OTHER INFORMATION: Nanobody

<400> SEQUENCE: 4

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
                20                  25                  30

Pro Met Gly Trp Phe Arg Gln Ala Pro Gly Lys Gly Arg Glu Leu Val
            35                  40                  45

Ala Ala Ile Ser Arg Thr Gly Gly Ser Thr Tyr Tyr Pro Glu Ser Val
```

```
                50                  55                  60
Glu Gly Arg Phe Thr Ile Ser Arg Asp Asn Ala Lys Arg Thr Val Tyr
 65                  70                  75                  80

Leu Gln Met Asn Ser Leu Arg Ala Glu Asp Thr Ala Val Tyr Tyr Cys
                 85                  90                  95

Ala Ala Ala Gly Val Arg Ala Glu Gln Gly Arg Val Arg Thr Leu Pro
                100                 105                 110

Ser Glu Tyr Thr Phe Trp Gly Gln Gly Thr Gln Val Thr Val Ser Ser
                115                 120                 125

Ala Ala Ala Glu Val Gln Leu Val Glu Ser Gly Gly Gly Leu Val Gln
                130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
                180                 185                 190

Glu Ser Val Glu Gly Arg Phe Thr Ile Ser Arg Asp Asn Ala Lys Arg
                195                 200                 205

Thr Val Tyr Leu Gln Met Asn Ser Leu Arg Ala Glu Asp Thr Ala Val
210                 215                 220

Tyr Tyr Cys Ala Ala Ala Gly Val Arg Ala Glu Gln Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 5
<211> LENGTH: 245
<212> TYPE: PRT
<213> ORGANISM: Artificial Sequence
<220> FEATURE:
<223> OTHER INFORMATION: Nanobody

<400> SEQUENCE: 5

Glu Val Gln Leu Val Glu Ser Gly Gly Gly Leu Val Gln Pro Gly Gly
 1                   5                  10                  15

Ser Leu Arg Leu Ser Cys Ala Ala Ser Gly Ser Val Phe Lys Ile Asn
                 20                  25                  30

Val Met Ala Trp Tyr Arg Gln Ala Pro Gly Lys Gly Arg Glu Leu Val
                 35                  40                  45

Ala Gly Ile Ile Ser Gly Gly Ser Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Ile Thr Thr Glu Ser Asp Tyr Asp Leu Gly Arg Arg Tyr Trp Gly
                100                 105                 110

Gln Gly Thr Leu Val Thr Val Ser Ser Gly Gly Gly Gly Ser Gly Gly
                115                 120                 125

Gly Ser Glu Val Gln Leu Val Glu Ser Gly Gly Gly Leu Val Gln Pro
                130                 135                 140

Gly Asn Ser Leu Arg Leu Ser Cys Ala Ala Ser Gly Phe Thr Phe Ser
145                 150                 155                 160
```

```
Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser
                245

<210> SEQ ID NO 6
<211> LENGTH: 385
<212> TYPE: PRT
<213> ORGANISM: Artificial Sequence
<220> FEATURE:
<223> OTHER INFORMATION: Nanobody

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Gly Trp Phe Arg Gln Ala Pro Gly Lys Gly Arg Glu Phe Val
        35                  40                  45

Ser Ser Ile Thr Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
            85                  90                  95

Ala Ala Tyr Ile Arg Pro Asp Thr Tyr Leu Ser Arg Asp Tyr Arg Lys
        100                 105                 110

Tyr Asp Tyr Trp Gly Gln Gly Thr Leu Val Thr Val Ser Ser Gly Gly
    115                 120                 125

Gly Gly Ser Gly Gly Gly Ser Glu Val Gln Leu Val Glu Ser Gly Gly
    130                 135                 140

Gly Leu Val Gln Pro Gly Asn Ser Leu Arg Leu Ser Cys Ala Ala Ser
145                 150                 155                 160

Gly Phe Thr Phe Ser Ser Phe Gly Met Ser Trp Val Arg Gln Ala Pro
            165                 170                 175

Gly Lys Gly Leu Glu Trp Val Ser Ser Ile Ser Gly Ser Gly Ser Asp
        180                 185                 190

Thr Leu Tyr Ala Asp Ser Val Lys Gly Arg Phe Thr Ile Ser Arg Asp
    195                 200                 205

Asn Ala Lys Thr Thr Leu Tyr Leu Gln Met Asn Ser Leu Arg Pro Glu
    210                 215                 220

Asp Thr Ala Val Tyr Tyr Cys Thr Ile Gly Gly Ser Leu Ser Arg Ser
225                 230                 235                 240

Ser Gln Gly Thr Leu Val Thr Val Ser Ser Gly Gly Gly Gly Ser Gly
            245                 250                 255

Gly Gly Ser Glu Val Gln Leu Val Glu Ser Gly Gly Gly Leu Val Gln
        260                 265                 270
```

```
Pro Gly Gly Ser Leu Arg Leu Ser Cys Ala Ala Ser Gly Phe Thr Phe
        275                 280                 285

Ser Ser Tyr Pro Met Gly Trp Phe Arg Gln Ala Pro Gly Lys Gly Arg
    290                 295                 300

Glu Phe Val Ser Ser Ile Thr Gly Ser Gly Gly Ser Thr Tyr Tyr Ala
305                 310                 315                 320

Asp Ser Val Lys Gly Arg Phe Thr Ile Ser Arg Asp Asn Ala Lys Asn
            325                 330                 335

Thr Leu Tyr Leu Gln Met Asn Ser Leu Arg Pro Glu Asp Thr Ala Val
                340                 345                 350

Tyr Tyr Cys Ala Ala Tyr Ile Arg Pro Asp Thr Tyr Leu Ser Arg Asp
            355                 360                 365

Tyr Arg Lys Tyr Asp Tyr Trp Gly Gln Gly Thr Leu Val Thr Val Ser
    370                 375                 380

Ser
385

<210> SEQ ID NO 7
<211> LENGTH: 261
<212> TYPE: PRT
<213> ORGANISM: Artificial Sequence
<220> FEATURE:
<223> OTHER INFORMATION: Nanobody

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Gly Trp Phe Arg Gln Ala Pro Gly Lys Gly Arg Glu Phe Val
        35                  40                  45

Ser Ser Ile Thr Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Tyr Ile Arg Pro Asp Thr Tyr Leu Ser Arg Asp Tyr Arg Lys
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Glu Val Gln Leu Val Glu Ser Gly Gly
    130                 135                 140

Gly Leu Val Gln Pro Gly Gly Ser Leu Arg Leu Ser Cys Ala Ala Ser
145                 150                 155                 160

Gly Phe Thr Phe Ser Ser Tyr Pro Met Gly Trp Phe Arg Gln Ala Pro
                165                 170                 175

Gly Lys Gly Arg Glu Phe Val Ser Ser Ile Thr Gly Ser Gly Gly Ser
            180                 185                 190

Thr Tyr Tyr Ala Asp Ser Val Lys Gly Arg Phe Thr Ile Ser Arg Asp
        195                 200                 205

Asn Ala Lys Asn Thr Leu Tyr Leu Gln Met Asn Ser Leu Arg Pro Glu
    210                 215                 220

Asp Thr Ala Val Tyr Tyr Cys Ala Ala Tyr Ile Arg Pro Asp Thr Tyr
225                 230                 235                 240
```

```
Leu Ser Arg Asp Tyr Arg Lys Tyr Asp Tyr Trp Gln Gly Thr Leu
                245                 250                 255

Val Thr Val Ser Ser
            260

<210> SEQ ID NO 8
<211> LENGTH: 408
<212> TYPE: PRT
<213> ORGANISM: Artificial Sequence
<220> FEATURE:
<223> OTHER INFORMATION: Nanobody

<400> SEQUENCE: 8

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
    130                 135                 140

Leu Val Glu Ser Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285

Ser Gly Gly Gly Leu Val Gln Pro Gly Gly Ser Leu Arg Leu Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335
```

```
Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
            355                 360                 365

Arg Pro Glu Asp Thr Ala Val Tyr Tyr Cys Ala Gly Thr Pro Leu
370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
            405

<210> SEQ ID NO 9
<211> LENGTH: 398
<212> TYPE: PRT
<213> ORGANISM: Artificial Sequence
<220> FEATURE:
<223> OTHER INFORMATION: Nanobody

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Leu Ser Ser Tyr
            20                  25                  30

Ala Met Gly Trp Phe Arg Gln Ala Pro Gly Lys Gly Arg Glu Phe Val
        35                  40                  45

Ala Arg Ile Ser Gln Gly Gly Thr Ala Ile Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Lys Asp Pro Ser Pro Tyr Tyr Arg Gly Ser Ala Tyr Leu Leu Ser
            100                 105                 110

Gly Ser Tyr Asp Ser Trp Gly Gln Gly Thr Leu Val Thr Val Ser Ser
        115                 120                 125

Gly Gly Gly Gly Ser Gly Gly Gly Ser Gly Gly Gly Gly Ser Glu
    130                 135                 140

Val Gln Leu Val Glu Ser Gly Gly Leu Val Gln Pro Gly Asn Ser
145                 150                 155                 160

Leu Arg Leu Ser Cys Ala Ala Ser Gly Phe Thr Phe Ser Ser Phe Gly
                165                 170                 175

Met Ser Trp Val Arg Gln Ala Pro Gly Lys Gly Leu Glu Trp Val Ser
            180                 185                 190

Ser Ile Ser Gly Ser Gly Ser Asp Thr Leu Tyr Ala Asp Ser Val Lys
        195                 200                 205

Gly Arg Phe Thr Ile Ser Arg Asp Asn Ala Lys Thr Thr Leu Tyr Leu
    210                 215                 220

Gln Met Asn Ser Leu Arg Pro Glu Asp Thr Ala Val Tyr Tyr Cys Thr
225                 230                 235                 240

Ile Gly Gly Ser Leu Ser Arg Ser Ser Gln Gly Thr Leu Val Thr Val
                245                 250                 255

Ser Ser Gly Gly Gly Gly Ser Gly Gly Gly Gly Ser Gly Gly Gly Gly
            260                 265                 270

Ser Glu Val Gln Leu Leu Glu Ser Gly Gly Gly Leu Val Gln Pro Gly
        275                 280                 285
```

```
Gly Ser Leu Arg Leu Ser Cys Ala Ala Ser Gly Arg Ile Phe Ser Leu
        290                 295                 300
Pro Ala Ser Gly Asn Ile Phe Asn Leu Leu Thr Ile Ala Trp Tyr Arg
305                 310                 315                 320
Gln Ala Pro Gly Lys Gly Arg Glu Leu Val Ala Thr Ile Asn Ser Gly
                325                 330                 335
Ser Arg Thr Tyr Tyr Ala Asp Ser Val Lys Gly Arg Phe Thr Ile Ser
            340                 345                 350
Arg Asp Asn Ser Lys Lys Thr Val Tyr Leu Gln Met Asn Ser Leu Arg
        355                 360                 365
Pro Glu Asp Thr Ala Val Tyr Tyr Cys Gln Thr Gly Ser Gly Ser Ser
370                 375                 380
Pro Asn Phe Trp Gly Gln Gly Thr Leu Val Thr Val Ser Ser
385                 390                 395

<210> SEQ ID NO 10
<211> LENGTH: 386
<212> TYPE: PRT
<213> ORGANISM: Artificial Sequence
<220> FEATURE:
<223> OTHER INFORMATION: Nanobody

<400> SEQUENCE: 10

Glu Val Gln Leu Leu Glu Ser Gly Gly Gly Leu Val Gln Pro Gly Gly
1               5                   10                  15
Ser Leu Arg Leu Ser Cys Ala Ala Ser Gly Arg Ile Phe Ser Leu Pro
            20                  25                  30
Ala Ser Gly Asn Ile Phe Asn Leu Leu Thr Ile Ala Trp Tyr Arg Gln
        35                  40                  45
Ala Pro Gly Lys Gly Arg Glu Leu Val Ala Thr Ile Asn Ser Gly Ser
    50                  55                  60
Arg Thr Tyr Tyr Ala Asp Ser Val Lys Gly Arg Phe Thr Ile Ser Arg
65                  70                  75                  80
Asp Asn Ser Lys Lys Thr Val Tyr Leu Gln Met Asn Ser Leu Arg Pro
                85                  90                  95
Glu Asp Thr Ala Val Tyr Tyr Cys Gln Thr Gly Ser Gly Ser Ser Pro
            100                 105                 110
Asn Phe Trp Gly Gln Gly Thr Leu Val Thr Val Ser Ser Gly Gly Gly
        115                 120                 125
Gly Ser Gly Gly Gly Ser Glu Val Gln Leu Val Glu Ser Gly Gly Gly
    130                 135                 140
Leu Val Gln Pro Gly Asn Ser Leu Arg Leu Ser Cys Ala Ala Ser Gly
145                 150                 155                 160
Phe Thr Phe Ser Ser Phe Gly Met Ser Trp Val Arg Gln Ala Pro Gly
                165                 170                 175
Lys Gly Leu Glu Trp Val Ser Ser Ile Ser Gly Ser Gly Ser Asp Thr
            180                 185                 190
Leu Tyr Ala Asp Ser Val Lys Gly Arg Phe Thr Ile Ser Arg Asp Asn
        195                 200                 205
Ala Lys Thr Thr Leu Tyr Leu Gln Met Asn Ser Leu Arg Pro Glu Asp
    210                 215                 220
Thr Ala Val Tyr Tyr Cys Thr Ile Gly Gly Ser Leu Ser Arg Ser Ser
225                 230                 235                 240
Gln Gly Thr Leu Val Thr Val Ser Ser Gly Gly Gly Gly Ser Gly Gly
                245                 250                 255
```

```
Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
        355                 360                 365

Leu Ser Gly Ser Tyr Asp Ser Trp Gly Gln Gly Thr Leu Val Thr Val
    370                 375                 380

Ser Ser
385

<210> SEQ ID NO 11
<211> LENGTH: 386
<212> TYPE: PRT
<213> ORGANISM: Artificial Sequence
<220> FEATURE:
<223> OTHER INFORMATION: Nanobody

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Val Tyr Leu Gln Met Asn Ser Leu Arg Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Ser Glu Val Gln Leu Val Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220
```

```
Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
                245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
    290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Val Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
        355                 360                 365

Leu Ser Gly Ser Tyr Asp Ser Trp Gly Gln Gly Thr Leu Val Thr Val
    370                 375                 380

Ser Ser
385

<210> SEQ ID NO 12
<211> LENGTH: 398
<212> TYPE: PRT
<213> ORGANISM: Artificial Sequence
<220> FEATURE:
<223> OTHER INFORMATION: Nanobody

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Leu Ser Ser Tyr
            20                  25                  30

Ala Met Gly Trp Phe Arg Gln Ala Pro Gly Lys Gly Arg Glu Phe Val
        35                  40                  45

Ala Arg Ile Ser Gln Gly Gly Thr Ala Ile Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Ala Lys Asp Pro Ser Pro Tyr Tyr Arg Gly Ser Ala Tyr Leu Leu Ser
        100                 105                 110

Gly Ser Tyr Asp Ser Trp Gly Gln Gly Thr Leu Val Thr Val Ser Ser
    115                 120                 125

Gly Gly Gly Gly Ser Gly Gly Gly Ser Gly Gly Gly Gly Ser Glu
130                 135                 140

Val Gln Leu Val Glu Ser Gly Gly Gly Leu Val Gln Pro Gly Asn Ser
145                 150                 155                 160

Leu Arg Leu Ser Cys Ala Ala Ser Gly Phe Thr Phe Ser Ser Phe Gly
            165                 170                 175

Met Ser Trp Val Arg Gln Ala Pro Gly Lys Gly Leu Glu Trp Val Ser
        180                 185                 190
```

```
Ser Ile Ser Gly Ser Gly Ser Asp Thr Leu Tyr Ala Asp Ser Val Lys
            195                 200                 205

Gly Arg Phe Thr Ile Ser Arg Asp Asn Ala Lys Thr Thr Leu Tyr Leu
        210                 215                 220

Gln Met Asn Ser Leu Arg Pro Glu Asp Thr Ala Val Tyr Tyr Cys Thr
225                 230                 235                 240

Ile Gly Gly Ser Leu Ser Arg Ser Ser Gln Gly Thr Leu Val Thr Val
                245                 250                 255

Ser Ser Gly Gly Gly Gly Ser Gly Gly Gly Ser Gly Gly Gly Gly
            260                 265                 270

Ser Glu Val Gln Leu Leu Glu Ser Gly Gly Leu Val Gln Pro Gly
        275                 280                 285

Gly Ser Leu Arg Leu Ser Cys Ala Ala Ser Gly Arg Ile Phe Ser Leu
        290                 295                 300

Pro Ala Ser Gly Asn Ile Phe Asn Leu Leu Thr Ile Ala Trp Tyr Arg
305                 310                 315                 320

Gln Ala Pro Gly Lys Gly Arg Glu Leu Val Ala Thr Ile Glu Ser Gly
                325                 330                 335

Ser Arg Thr Tyr Tyr Ala Asp Ser Val Lys Gly Arg Phe Thr Ile Ser
            340                 345                 350

Arg Asp Asn Ser Lys Lys Thr Val Tyr Leu Gln Met Asn Ser Leu Arg
            355                 360                 365

Pro Glu Asp Thr Ala Val Tyr Tyr Cys Gln Thr Ser Gly Ser Gly Ser
        370                 375                 380

Pro Asn Phe Trp Gly Gln Gly Thr Leu Val Thr Val Ser Ser
385                 390                 395

<210> SEQ ID NO 13
<211> LENGTH: 386
<212> TYPE: PRT
<213> ORGANISM: Artificial Sequence
<220> FEATURE:
<223> OTHER INFORMATION: Nanobody

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160
```

-continued

```
Phe Thr Phe Ser Ser Phe Gly Met Ser Trp Val Arg Gln Ala Pro Gly
            165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
            195                 200                 205

Ala Lys Thr Thr Leu Tyr Leu Gln Met Asn Ser Leu Arg Pro Glu Asp
            210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
            245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
            275                 280                 285

Ser Tyr Ala Met Gly Trp Phe Arg Gln Ala Pro Gly Lys Gly Arg Glu
            290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
            325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
            355                 360                 365

Leu Ser Gly Ser Tyr Asp Ser Trp Gly Gln Gly Thr Leu Val Thr Val
    370                 375                 380

Ser Ser
385
```

METHOD FOR THE PRODUCTION OF DOMAIN ANTIBODIES

RELATED APPLICATIONS

This application is a continuation of U.S. patent application Ser. No. 13/266,503, filed Mar. 8, 2012, which is a national stage filing under 35 U.S.C. § 371 of international application PCT/EP2010/055916, filed Apr. 30, 2010, which was published under PCT Article 21(2) in English, and claims the benefit under 35 U.S.C. § 119(e) of U.S. provisional application Ser. No. 61/174,184, filed Apr. 30, 2009, and of U.S. provisional application Ser. No. 61/304,834, filed Feb. 16, 2010, the disclosures of which are incorporated by reference herein in their entireties.

FIELD OF THE INVENTION

The present invention is based on the surprising finding that expression of domain antibodies in non-*E. coli* hosts results in a product related variant which lacks the formation of at least one disulfide bond, but nevertheless is, in most cases, fully functional.

Hence, the present invention relates to an improved method for the manufacture of immunoglobulins, in particular domain antibodies. More specifically, the present invention relates to a method of producing homogeneous domain antibodies in which the proportion of variants lacking at least one disulfide bridge is strongly reduced or absent. The domain antibodies produced according to the invention are superior in terms of product homogeneity because the product related variant lacking at least one disulfide bond is reduced or absent. This is beneficial e.g. in the context of a therapeutic application of the domain antibody. Therefore, the present invention also relates to improved domain antibodies for therapeutic use, obtainable by methods of the present invention.

TECHNICAL BACKGROUND

For therapeutic applications, antibodies or antibody fragments must be of very high product quality. This requires, amongst others, homogeneity in structural terms. Moreover, the production costs are strongly influenced by difficulties encountered during the production process. Low yields or lack of homogeneity will impact the economics of the production process, and hence, the costs for the therapeutic, overall. For example, difficulties to separate structural variants of the desired antibody or antibody fragment will necessitate complex and costly purification strategies.

Amongst other requirements, therapeutic antibodies or their fragments must be properly folded. Protein folding is a spontaneous process leading to a uniquely folded structure depending on the given amino acid sequence. Cell surface and secreted proteins such as immunoglobulins often contain disulfide bonds (also referred to as disulfide bridges) that covalently link two cysteines and impart structural stability in the environment outside of the cell. An important event in the folding of these proteins is therefore the formation of these disulfide bonds. The number and position of the disulfide bridges will be determined by the number and location of suitable cysteine residues in the amino acid sequence of the antibody or antibody fragment.

The correct formation of all disulfide bridges is instrumental for proper folding and the stability of the obtained product. Proteins comprising disulfide bonds are oftentimes difficult to express recombinantly. For example, the expression of conventional immunoglobulins or their fragments, including Fab or scFv fragments, is problematic in terms of yield and functionality. For example, a conventional IgG molecule comprises a multitude of disulfide bonds both within single chains and between the four chains constituting the complete molecule. Early studies have already pointed to the difficulties in obtaining properly formed disulfide bridges for IgG molecules and have investigated various in vitro conditions (Litske & Dorrington J. Biol. Chem. 249: 5633, 1974).

In case one or more disulfide bridges are lacking in a conventional immunoglobulin (e.g. IgG, IgA, IgE, IgM), or a fragment derived therefrom, e.g. Fab, F(ab')2 or scFv, functionality of the resulting product is typically compromised. Significant portions of the product obtained by recombinant expression will be non functional because of the missing disulfide bride(s), as widely reported in the art. Moreover, in the case of conventional antibodies or antibody fragments, such as Fab or scFv fragments, the formation of disulfide bridges has been reported to be rate limiting for the secretion of any product, in the first place.

It is known that e.g. formation of functional Fab, the heavy chain constant domains CH2 and CH3, or scFv is severely limited. For example, the amount of functional scFv may be entirely limited by correct disulfide formation (Ryabova et al., Nature Biotechn. 15: 79, 1997). The majority of the protein may form inactive aggregates, unless several folding helpers, including e.g. heavy chain binding protein (BiP) and protein disulfide isomerase (PDI) are overexpressed and act in an ATP dependent fashion (Mayer et al., J. Biol. Chem. 275: 29421, 2000; Lilie et al., J. Biol. Chem. 269: 14290, 1994; Vinci et al. J. Biol. Chem. 279: 15059, 2004; Merk et al., J. Biochem. 125: 328, 1999; Xu et al., Metabol. Engineer. 7: 269, 2005).

The limitation of obtaining adequate yields of functional product has been reported for conventional immunoglobulins and their fragments across a broad range of expression systems, including in vitro translation, *E. coli*, *Saccharomyces cerevisiae*, Chinese hamster ovary cells and baculovirus systems in insect cells or *P. pastoris*, amongst others (Ryabova et al., Nature Biotechnology 15: 79, 1997; Humphreys et al., FEBS Letters 380: 194, 1996; Shusta et al., Nature Biotech. 16: 773, 1998; Hsu et al., Protein Expr. & Purif. 7: 281, 1996; Mohan et al., Biotechnol. & Bioeng. 98: 611, 2007; Xu et al., Metabol. Engineer. 7: 269, 2005; Merk et al., J. Biochem. 125: 328, 1999; Whiteley et al., J. Biol. Chem. 272: 22556, 1997; Gasser et al., Biotechnol. Bioeng. 94: 353, 2006).

Thus the correct formation of canonical disulfide bridges is considered to be generally limiting to conventional antibody expression in microorganisms, including mammalian host cells.

In contrast to these difficulties observed with conventional four-chain antibodies or their fragments, including Fab and scFv, domain antibodies can be readily expressed and secreted in a correctly folded, fully functional form from hosts like *E. coli* or *P. pastoris* at a sufficient rate and level. Domain antibodies are characterized by formation of the antigen binding site by a single antibody domain, which does not require interaction with a further domain (e.g. in the form of VH/VL interaction) for antigen recognition. Production of Nanobodies, as one specific example of a domain antibody, in lower eukaryotic hosts such as *Pichia pastoris* has been extensively described in WO 94/25591.

The fact that fully functional domain antibodies can readily be produced in e.g. *E. coli* or yeast represents an important advantage of this immunoglobulin-format over conventional immunoglobulins. The production of domain antibodies in *E. coli* and yeast results in a good yield of functional product. The problems of obtaining sufficient amounts of functional product known from other immunoglobulin formats is hence unknown for domain antibodies.

SUMMARY OF THE INVENTION

Surprisingly, despite the good yield and functionality, a product related variant has been observed in the expression of domain antibodies in non-*E. coli* hosts. The present invention relates to improved methods of producing domain antibodies, characterized by the reduction or absence of the product related variant.

The present inventors have unexpectedly observed that despite the high yield and functionality of domain antibodies produced in non-*E. coli* hosts, in particular yeast, there is a quantitatively significant fraction of product that represents a structural variant. In particular, it has unexpectedly been found that a fraction of the product lacks at least one disulfide bond. The finding of considerable quantities of such a variant in non-*E. coli* hosts was entirely unexpected. It is consistently reported in the art that conventional antibodies, or fragments thereof, lacking at least one disulfide bond, are characterized by a loss of function, typically together with problems in secretion from the host.

Hence, in one aspect the present invention relates to identifying and characterizing the product related variant in the first place.

Based on the full characterization of the product related variant observed it was established by the inventors that the variant lacked at least one disulfide bond.

In a further aspect of the present invention, methods are provided which reduce or eliminate the product related variant lacking at least one disulfide bond.

Consequently, the present invention provides methods of producing domain antibodies which overcome this unexpected problem.

More specifically, the present invention provides methods for reducing the formation of variants lacking at least one disulfide bond. Such methods may reside in adapting the culturing conditions in terms of temperature, pH, conductivity, and/or addition of yeast extract and/or peptone, as well as the addition of oxidizing agents whilst culturing the host.

In addition, the present invention also comprises treatment of the domain antibodies after removal of the host from the culture medium, i.e. during one or more of the purification steps, e.g. by the addition of oxidizing agents, increasing pH and/or temperature, applying high pressure or applying refolding conditions e.g. the exposure to a redox couple, with or without presence of a denaturant. Furthermore, the present invention provides methods of removing variants lacking at least one disulfide bridge e.g. by means of exposure to immobilized thiol groups in the presence of a denaturant, or by RP-HPLC.

More specifically, the present invention relates to methods for producing a domain antibody in a host other than *E. coli*, preferably yeast, comprising
  a) applying conditions that promote the formation of disulfide bridges in domain antibodies, or
  b) removing domain antibodies lacking at least one disulfide bridge, or
  c) a combination of (a) and (b).

Particular aspects of the invention comprise methods as outlined above, wherein the conditions that promote the formation of disulfide brides are selected from one or more of the following:
  a) addition of oxidizing agents, preferably oxidizing metal ions, preferably one or more selected from $Cu^{2+}$, $Fe^{2+}$, $Fe^{3+}$ and $Zn^{2+}$;
  b) enhancing expression of a thiol isomerase, which can advantageously be selected from Protein Disulfide Isomerase (PDI), calsequestrin and other PDI-related proteins comprising, but not limited to ERp72, ERp57, ERp60, ERp44, ERp5, ERp27 and PDIR, preferably PDI;
  c) adapting the culturing conditions by one or more selected from the following: lowering culturing temperature and/or optimizing the culturing medium, including but not limited to reduction of methanol feed for hosts requiring a methanol feed, lowering conductivity of the culture medium, addition of yeast extract and/or peptone, or any combination thereof; in particular embodiments, said culturing temperature is lowered by 5° C. as compared to the standard culturing temperature for the host organism, and/or said methanol feed is lowered by 30-80% as compared to the standard methanol feed for the respective host and/or said conductivity of the culture medium is lowered by 30% to 80% as compared to the standard medium for the respective host, and/or yeast extract and/or peptone are added to the culture medium in an amount of 0 to 20% of the feed;
  d) refolding the domain antibody in the presence of redox-buffer, preferably in the additional presence of denaturant, for example refolding the domain antibody in the presence of denaturant and redox-buffer using 2M guanidinium hydrochloride and 1:5 mM/mM cystamine/cysteamine;
  e) treating the domain antibody by oxygenation, increasing temperature, increasing pH, or high pressure or any combination thereof, for example treating the domain antibody by increasing the temperature to 40-60° C., preferably 55° C., increasing pH to pH 8-9, and/or subjecting the domain antibody to high pressure, for example 250 to 10000 bar, such as about 1000 to about 2000 bar, optionally combined with oxygenation by purging with oxygen; and
  f) combinations of any of a) through e).

The invention also relates to methods as set forth above, wherein an oxidizing agent, preferably oxidizing metal ions, more preferably one or more selected from $Cu^{2+}$, $Fe^{2+}$, $Fe^{3+}$ and $Zn^{2+}$, are added to at least one production step of the domain antibody, preferably selected from: culturing the host to produce the domain antibody, the culture broth after fermentation, the supernatant comprising the domain antibody after removal of the host, any step after purification of the domain antibody, or the purified domain antibody.

In one embodiment, the invention pertains to methods as described above, wherein conditions that remove domain antibodies lacking at least one disulfide bridge are selected from
  a) binding domain antibodies comprising free thiol groups to suitable reactive groups, including but not limited to immobilized thiol groups, optionally under denaturing conditions;
  b) reverse phase high performance chromatography.

The invention also relates to any of the above methods, wherein said addition of oxidizing agents, preferably oxidizing metal ions, preferably $Cu^{2+}$, $Fe^{2+}$, $Fe^{3+}$ and $Zn^{2+}$, more preferably 1-10 mM Cu2+, is performed alone, or in combination with one or more of the conditions described above.

In particular embodiments of the invention, the non-*E. coli* host is selected from prokaryotic hosts other than *E. coli*, or eukaryotic hosts, for example eukaryotic host selected from insect cells, mammalian cells, and lower eukaryotic hosts comprising yeasts such as *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis*, preferably *Pichia pastoris*.

The present invention relates to domain antibodies comprising or essentially consisting of, but not limited to, a domain antibody that is a light chain variable domain sequence or a heavy chain variable domain sequence, more specifically a domain antibody which is a heavy chain variable domain sequence that is derived from a conventional four-chain antibody or a heavy chain variable domain sequence that is derived from a heavy chain antibody, in particular a domain antibody (or an amino acid sequence that is suitable for use as a domain antibody) which is a single domain antibody (or an amino acid sequence that is suitable for use as a single domain antibody), a "dAb" (or an amino acid sequence that is suitable for use as a dAb) or a Nanobody (including but not limited to a VHH sequence), preferably a Nanobody.

The method according to the present invention as described above comprises at least the steps of culturing the host to produce the domain antibody comprising:
  i) cultivating said host or host cell under conditions that are such that said host or host cell will multiply
  ii) maintaining a host or host cell under conditions that are such that said host or host cell expresses and/or produces the domain antibody
optionally followed by:
  iii) isolating and/or purifying the secreted domain antibody from the medium.

According to the invention, the methods as described above, wherein conditions that promote the formation of disulfide bridges are applied at one or more of step i), step ii), after step ii), or at or after step iii) or conditions that remove domain antibodies lacking at least one disulfide bridge are applied after step iii).

The invention also relates to domain antibodies obtainable by any of the methods as set forth herein, pharmaceutical compositions and other compositions comprising such domain antibodies, and therapeutic uses of the domain antibodies or methods of treatment comprising the use of the domain antibodies.

DETAILED DESCRIPTION OF THE INVENTION

Definitions

Figure 1:
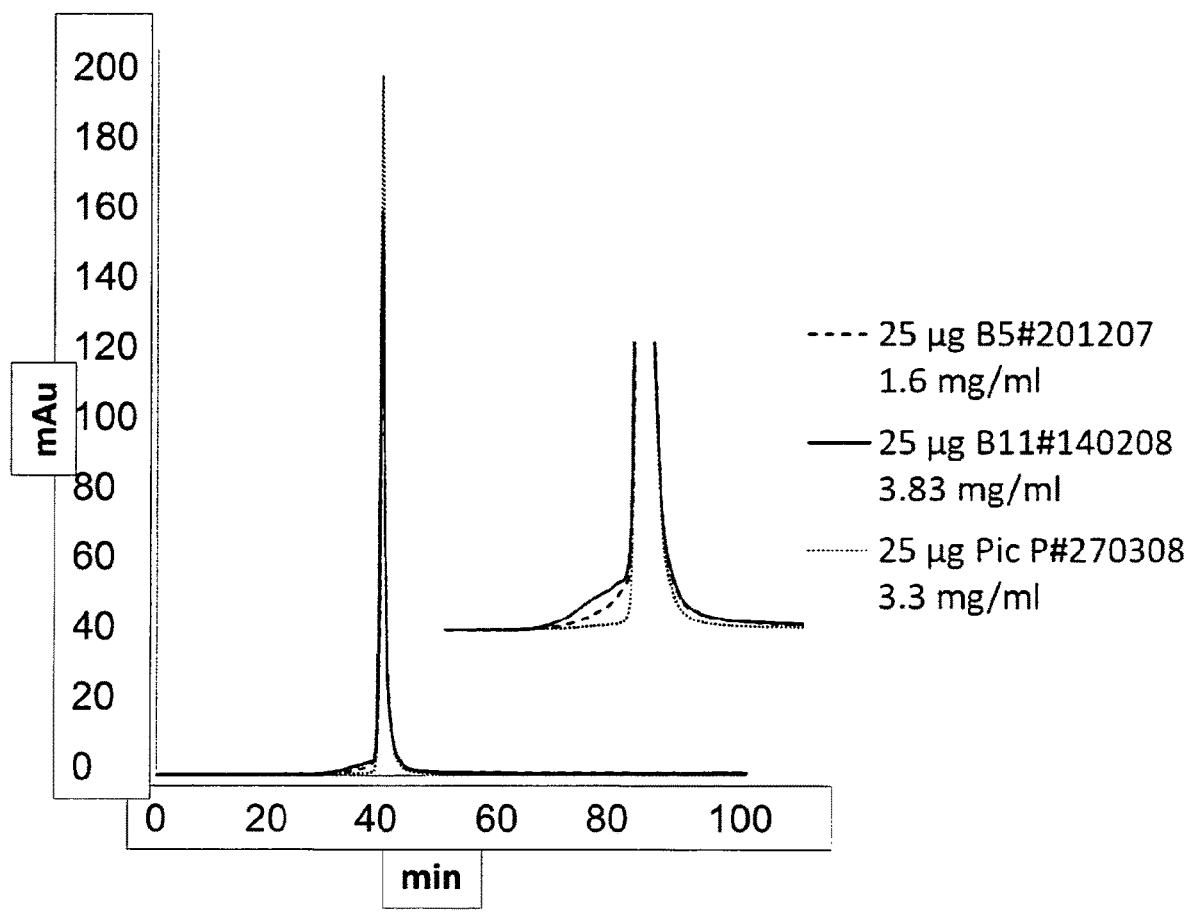
FIG. 1: SEC-HPLC chromatogram of two RANKL008a *E. coli* batches compared to a batch prepared from *P. pastoris* fermentation; all batches have been purified using similar purification protocols. X axis: retention time in minutes, Y-axis: OD monitored at 280 nm.
Figure 2:
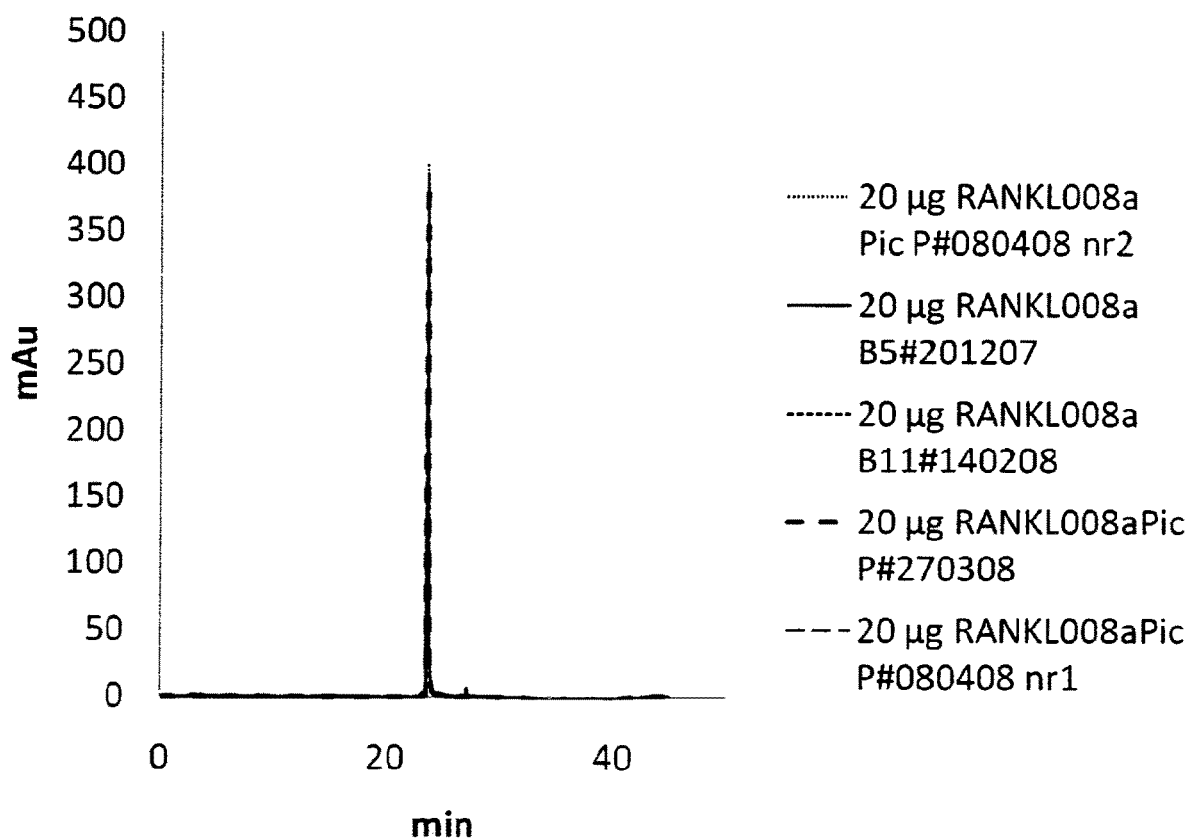
FIGS. 2 and 3 illustrate the comparison of the *E. coli* and *P. pastoris* material upon analysis by IEX-HPLC. A zoom on the main peak base area (FIG. 3) shows that materials prepared from *P. pastoris* fermentations show less, and less pronounced minor pre- and postpeaks.
Figure 3:
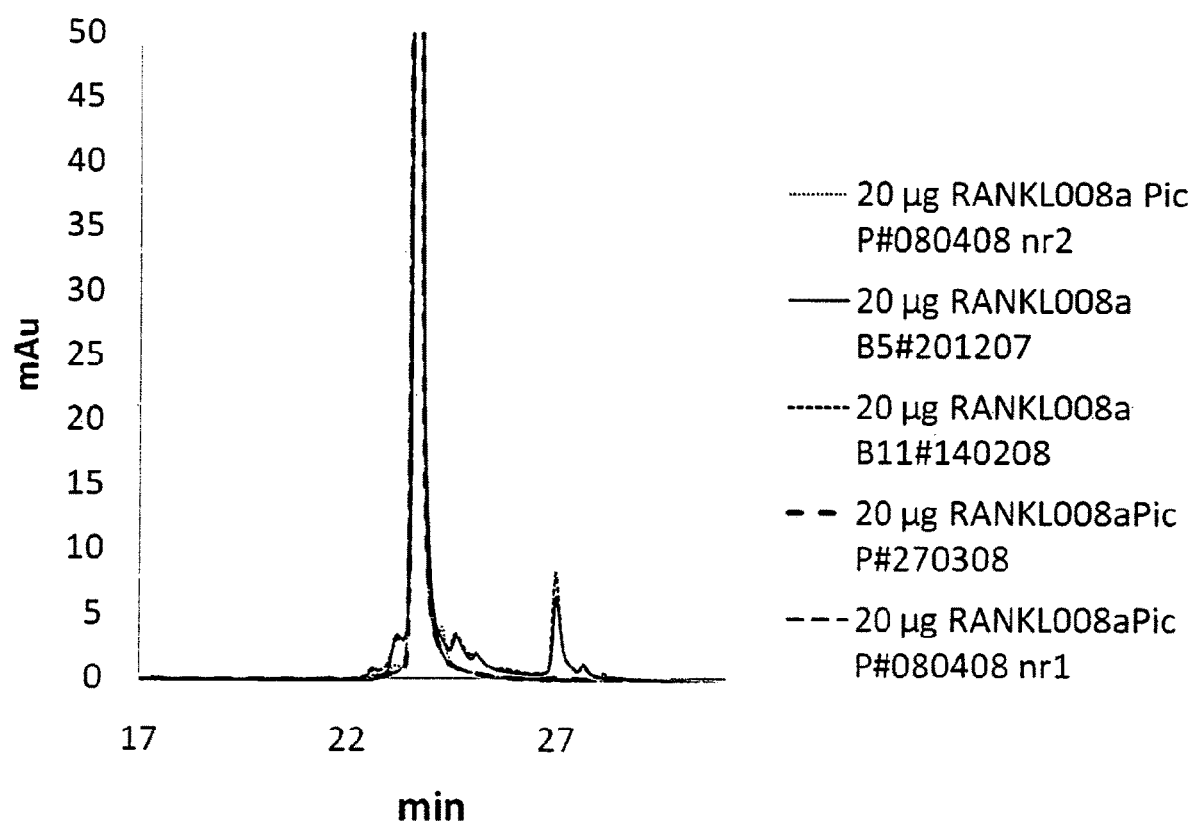

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, CA (1981); Roitt et al., "Immunology" (6th. Ed.), Mosby/Elsevier, Edinburgh (2001); Roitt et al., Roitt's Essential Immunology, 10th Ed. Blackwell Publishing, U K (2001); and Janeway et al., "Immunobiology" (6th Ed.), Garland Science Publishing/Churchill Livingstone, New York (2005), as well as to the general background art cited herein.

Domain Antibodies

The term "domain antibody", interchangeably used with "single domain antibody", "single variable domain" and "immunoglobulin single variable domain" defines molecules wherein the antigen binding site is present on, and formed by, a single immunoglobulin domain. This sets domain antibodies apart from "conventional" immunoglobulins or their fragments, wherein two immunoglobulin domains, in particular two variable domains interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of a domain antibody is formed by a single VH or VL domain. Hence, the antigen binding site of a domain antibody is formed by no more than three CDRs.

The term "domain antibody", "single domain antibody", "single variable domain" or "immunoglobulin single variable domain" hence does not comprise conventional immunoglobulins or their fragments which require interaction of at least two variable domains for the formation of an antigen binding site. However, these terms do comprise fragments of conventional immunoglobulins wherein the antigen binding site is formed by a single variable domain.

Generally, single variable domains will be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's, as further described herein). Such single variable domains and fragments are most preferably such that they comprise an immunoglobulin fold or are capable for forming, under suitable conditions, an immunoglobulin fold. As such, the single variable domain may for example comprise a light chain variable domain sequence (e.g. a $V_L$-sequence) or a suitable fragment thereof; or a heavy chain variable domain sequence (e.g. a $V_H$-sequence or $V_{HH}$ sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a $V_H/V_L$ interaction—to form a functional antigen binding domain). For example, the single variable domain of a domain antibody (or an amino acid sequence that is suitable for use as a domain antibody) may be a single domain antibody (or an amino acid sequence that is suitable for use as a single domain antibody), a "dAb" or dAb (or an amino acid sequence that is suitable for use as a dAb) or a Nanobody® (as defined herein, and including but not limited to a $V_{HH}$ sequence) [Note: Nanobody® and Nanobodies® are registered trademarks of Ablynx N.V.]; other single variable domains, or any suitable fragment of any one thereof. For a general description of (single) domain antibodies, reference is also made to the prior art cited herein, as well as to EP 0 368 684. For the term "dAb's", reference is for example made to Ward et al. (Nature 1989 Oct. 12; 341 (6242): 544-6), to Holt et al., Trends Biotechnol., 2003, 21(11):484-490; as well as to for example WO 04/068820, WO 06/030220, WO 06/003388 and other published patent applications of Domantis Ltd. It should also be noted that, although less preferred in the context of the present invention because they are not of mammalian origin, single domain antibodies or single variable domains can be derived from certain species of shark (for example, the so-called "IgNAR domains", see for example WO 05/18629).

In particular, the amino acid sequence of the invention may be a Nanobody or a suitable fragment thereof. For a further description of $V_{HH}$'s and Nanobodies, reference is made to the review article by Muyldermans in Reviews in Molecular Biotechnology 74(2001), 277-302; as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular $V_{HH}$ sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164.

Thus, in the meaning of the present invention, the term "single domain antibody", "domain antibody", "single variable domain" or "immunoglobulin single variable domain" comprises polypeptides which are derived from a non-human source, preferably a camelid, preferably a camel heavy chain antibody. They may be humanized, as previously described. Moreover, the term comprises polypeptides derived from non-camelid sources, e.g. mouse or human, which have been "camelized", as previously described.

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). The terms antigen-binding molecules or antigen-binding protein are used interchangeably with immunoglobulin sequence, and include Nanobodies.

In one embodiment of the invention, the domain antibodies are light chain variable domain sequences (e.g. a $V_L$-sequence), or heavy chain variable domain sequences (e.g. a $V_H$-sequence); more specifically, the domain antibodies can be heavy chain variable domain sequences that are derived from a conventional four-chain antibody or heavy chain variable domain sequences that are derived from a heavy chain antibody.

The domain antibodies provided by the invention are preferably in essentially isolated form (as defined herein), or form part of a protein or polypeptide of the invention (as defined herein), which may comprise or essentially consist of one or more domain antibodies and which may optionally further comprise one or more further amino acid sequences (all optionally linked via one or more suitable linkers). For example, and without limitation, the one or more domain antibodies may be used as a binding unit in such a protein or polypeptide, which may optionally contain one or more further amino acid sequences that can serve as a binding unit (i.e. against one or more other targets than cell associated antigens), so as to provide a monovalent, multivalent or multispecific polypeptide of the invention, respectively, all as described herein. Such a protein or polypeptide may also be in essentially isolated form (as defined herein).

The invention includes immunoglobulin sequences of different origin, comprising mouse, rat, rabbit, donkey, human and camelid immunoglobulin sequences. The invention also includes fully human, humanized or chimeric immunoglobulin sequences. For example, the invention comprises camelid immunoglobulin sequences and humanized camelid immunoglobulin sequences, or camelized domain antibodies, e.g. camelized dAb as described by Ward et al (see for example WO 94/04678 and Davies and Riechmann (1994 and 1996)). Moreover, the invention comprises fused immunoglobulin sequences, e.g. forming a multivalent and/or multispecific construct (for multivalent and multispecific polypeptides containing one or more $V_{HH}$ domains and their preparation, reference is also made to Conrath et al., J. Biol. Chem., Vol. 276, 10. 7346-7350, 2001, as well as to for example WO 96/34103 and WO 99/23221), and immunoglobulin sequences comprising tags or other functional moieties, e.g. toxins, labels, radiochemicals, etc., which are derivable from the immunoglobulin sequences of the present invention.

The amino acid sequence and structure of an immunoglobulin sequence, in particular a Nanobody can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively.

According to the invention, domain antibodies comprise constructs comprising two or more antigen binding units in the form of single domains, as outlined above. For example, two (or more) domain antibodies with the same or different antigen specificity can be linked to form e.g. a bivalent, trivalent or multivalent construct. By combining domain antibodies of two or more specificities, bispecific, trispecific etc. constructs can be formed. For example, a domain antibody according to the invention may comprise two or three domain antibodies directed against the same target, or two domain antibodies directed against target A, and one domain antibody against target B. Such constructs and modifications thereof, which the skilled person can readily envisage, are all encompassed by the term domain antibody as used herein.

The total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein.

Domain antibodies will oftentimes comprise at least one intradomain disulfide bridge between cysteine 22 and cysteine 92 (residues numbered according to Kabat numbering). Sometimes, Nanobodies comprise a disulfide bond between CDR3 and Cys45 in the framework region FR2. There may also be a disulfide bond between CDR2 and CDR3 for example between cysteine 45 and CDR3 or between cysteine 50 and CDR3 (Muyldermans, 2001). More specifically, crystal structure analysis of domain antibodies has exhibited 9β strands folded in two sheets that pack against each other and are stabilized by a conserved disulfide bond. The abundant disulfide bridges known from conventional antibodies to form between different chains are absent from domain antibodies.

All these molecules are also referred to as "polypeptide of the invention", which is synonymous with "immunoglobulin sequences of the invention".

In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acid sequences or nucleotide sequences encoding the same, unless the context requires a more limited interpretation.

For a general description and for some non-limiting examples of Nanobodies (and of polypeptides comprising the same) that are directed against RANKL and that can be expressed/produced using the methods described herein, reference is made to the International application WO 08/142164. For a general description and for some non-limiting examples of Nanobodies (and of polypeptides comprising the same) that are directed against IL-6R and that can be expressed/produced using the methods described herein, reference is made to the International application WO 08/020079, and in particular to the International application PCT/EP2010/054764 filed by Ablynx N.V. on Apr. 12, 2010 and entitled "Improved amino acid sequences directed against IL-6R and polypeptides comprising the same for the treatment of IL-6R related diseases and disorders" and the International application PCT/EP2010/054747 filed by Ablynx on Apr. 12, 2010 and entitled "Improved amino acid sequences directed against IL-6R and polypeptides comprising the same for the treatment of IL-6R related diseases and disorders."

For a general description and for some non-limiting examples of Nanobodies (and of polypeptides comprising the same) that are directed against IL-23 (and in particular the subunit p19 of IL23) and that can be expressed/produced using the methods described herein, reference is made to the International application WO 09/068627, and in particular to the U.S. provisional application 61/181,384 filed by Ablynx N.V. on May 27, 2009 and entitled "Biparatopic protein constructs directed against IL-23" and the US provisional filed by Ablynx on Apr. 30, 2010 and entitled "Amino acid sequence directed against the p19 subunit of the heterodimeric cytokine IL-23."

For a general description and for some non-limiting examples of Nanobodies (and of polypeptides comprising the same) that are directed against IL-23 (and in particular the subunit p19 of IL23) and that can be expressed/produced using the methods described herein, reference is made to the International application WO 09/068627, and in particular to the U.S. provisional application 61/181,384 filed by Ablynx N.V. on May 27, 2009 and entitled "Biparatopic protein constructs directed against IL-23" and the US provisional filed by Ablynx on Apr. 30, 2010 and entitled "Amino acid sequence directed against the p19 subunit of the heterodimeric cytokine IL-23."

For a general description and for some non-limiting examples of Nanobodies (and of polypeptides comprising the same) that are directed against IL-23 (and in particular the subunit p19 of IL23) and that can be expressed/produced using the methods described herein, reference is made to the International application WO 09/068627, and in particular to the U.S. provisional application 61/181,384 filed by Ablynx N.V. on May 27, 2009 and entitled "Biparatopic protein constructs directed against IL-23" and the US provisional filed by Ablynx on Apr. 30, 2010 and entitled "Amino acid sequence directed against the p19 subunit of the heterodimeric cytokine IL-23."

Hosts

The terms "host" and "host cells" are used interchangeably. The present invention relates to hosts without limitation other than *E. coli*, provided that they are suitable for the production of a domain antibody. In particular the present invention relates to non-*E. coli* hosts producing domain antibodies, wherein a part of the produced domain antibodies is lacking at least one disulfide bridge.

Specific examples of suitable hosts comprise prokaryotic organisms, such as coryneform bacteria or enterobacteriaceae other than *E. coli*. Also comprised are insect cells, in particular insect cells suitable for baculovirus mediated recombinant expression like Trioplusiani or *Spodoptera frugiperda* derived cells, including, but not limited to BTI-TN-5B1-4 High Five™ insect cells (Invitrogen), SF9 or Sf21 cells; mammalian cells like CHO cells and lower eukaryotic hosts comprising yeasts such as *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis*. Yeast is a preferable host of the present invention, and particularly preferred is *P. pastoris*.

The host of the present invention will be capable of producing a domain antibody. It will typically be genetically modified to comprise one or more nucleic acid sequences encoding one or more domain antibodies. Non-limiting examples of genetic modifications comprise the transformation e.g. with a plasmid or vector, or the transduction with a viral vector. Some hosts can be genetically modified by fusion techniques. Genetic modifications include the introduction of separate nucleic acid molecules into a host, e.g. plasmids or vectors, as well as direct modifications of the genetic material of the host, e.g. by integration into a chromosome of the host, e.g. by homologous recombination. Oftentimes a combination of both will occur, e.g. a host is transformed with a plasmid, which, upon homologous recombination will (at least partly) integrate into the host chromosome. The skilled person knows suitable methods of genetic modification of the host to enable the host to produce domain antibodies.

Disulfide Bridge

Disulfide bridge, or disulfide bond (used interchangeably) means the covalent bond formed between two cysteine residues that are in an appropriate location within the amino acid sequence of a domain antibody. The present invention thus relates to intramolecular, intradomain disulfide bridges.

Typically, domain antibodies, including VH and VHH domain antibodies, encompass one conserved disulfide bond, most often linking C22 and C92 (according to Kabat numbering). Some VHH may have an additional disulfide bridge linking two CDRs, such as CDR2 (e.g. position 50 according to Kabat numbering) and CDR3, CDR1 and CDR2 or CDR1 and CDR3.

In domain antibody constructs comprising more than one antibody domain, there will be a respectively higher number of disulfide bonds. For example, a construct comprising three antigen binding domains (e.g. three VHH domains), there will oftentimes be three disulfide bridges (one per VHH domain).

Any reference to disulfide bond or disulfide bridge is to be understood to also refer to more than one bond, i.e. to disulfide bonds or disulfide bridges, unless otherwise specified.

The intramolecular disulfide bridge within the domain antibody is formed in the process of protein folding and stabilizes the proper conformation of the domain antibody.

It has surprisingly been found that the disulfide bond within domain antibodies, despite their role in defining and/or stabilizing the three dimensional structure in the course of protein folding, are not essential for either the efficient production of the domain antibody by the host, nor its function. This represents a fundamental difference to reports in the art, according to which disulfide bonding is decisive for production yield and function of antibody fragments like Fab fragments (Gasser et al. Biotechnol. Bioeng. 94: 535, 2006).

In the context of this application, the term "product related variant" means a domain antibody lacking at least one disulfide bridge. In a construct comprising e.g. three VHH domains, the term product related variant will accordingly encompass variants lacking e.g. one, two or three disulfide bridges. At some instances the product related variant is abbreviated as "variant".

General Methods

The skilled person is well aware of general methods for producing domain antibodies in non-*E. coli* hosts.

For example, production of Nanobodies in lower eukaryotic hosts such as *Pichia pastoris* has been extensively described in WO 94/25591. The contents of this application are explicitly referred to in the connection with general culturing techniques and methods, including suitable media and conditions. The contents of this document are incorporated by reference. The skilled person can also devise suitable genetic constructs for expression of domain antibodies in non-*E. coli* hosts on the basis of common general knowledge. The present invention also relates to specific conditions and genetic constructs described in the art, for example the general culturing methods, plasmids, promoters and leader sequences described in WO 94/25591, Gasser et al. Biotechnol. Bioeng. 94: 535, 2006; Gasser et al. Appl. Environ. Microbiol. 73: 6499, 2007; or Damasceno et al. Microbiol. Biotechnol. 74: 381, 2007.

In a significant fraction of the domain antibodies, in particular Nanobodies produced by non-*E. coli* hosts, in particular *Pichia*, the presence of free thiol is observed, due to unpaired cysteine residues (although in most cases these Nanobodies are still functional and well-expressed). The absence of these disulfide bridges might have an impact on the quality and the homogeneity of the final Nanobody product. A high product quality and homogeneity is, however, a prerequisite for e.g. the therapeutic use of these products.

The present invention provides methods for the manufacture of domain antibodies wherein the quality of the domain antibodies is improved (i.e. with a reduced level of free thiol, or its absence). The quality of the domain antibodies is improved by applying specified conditions in which the formation of the missing disulfide bridge(s) is promoted during the growth of the host, during the expression of the domain antibody, and/or after the expression (i.e. before or after purification of the domain antibody). The present invention also provides methods of removing the product related variant.

Any reference to conditions that promote the formation of disulfide bonds is equally understood to mean conditions that remove or reduce the product related variant, and vice versa.

In the context of the present invention, the "removal" of product related variant can either mean that the missing disulfide bridge(s) are properly formed, such that the variant becomes structurally identical to the desired domain antibody. Alternatively, removal can mean that the product related variant is physically separated from the mixture of domain antibodies comprising both the desired domain antibody species having all disulfide bridges, and the product related variant. The correct meaning will be apparent from the context. In a preferred embodiment, removal has the first meaning, i.e. the product related variant forms all disulfide bridges and thus becomes the desired domain antibody. In view of the quantitatively significant contribution of the product related variant, which can, depending on the culturing conditions, amount to 15-25% of the overall domain antibody yield, the conversion of the variant into the desired product is highly advantageous.

More particularly, the present invention provides a method for producing an immunoglobulin at least comprising the steps of:
i) cultivating a host or host cell (as defined herein) under conditions that are such that said host or host cell will multiply
ii) maintaining said host or host cell under conditions that are such that said host or host cell expresses and/or produces the immunoglobulin optionally followed by:
iii) isolating and/or purifying the secreted immunoglobulin from the medium, wherein conditions are applied that promote the formation of a disulfide bridge at step i), at step ii), after step ii) and/or at or after step iii).

In one embodiment of the invention, the conditions that promote the formation of a disulfide bridge are applied at step i). Accordingly such a method comprises at least the steps of: i) cultivating a host or host cell under conditions that are such that said host or host cell will multiply and that promote the formation of a disulfide bridge, e.g. at least including the following:
a) addition of oxidizing agents, preferably oxidizing metal ions, preferably one or more selected from $Cu^{2+}$, $Fe^{2+}$, $Fe^{3+}$ and $Zn^{2+}$;
b) enhancing expression of a thiol isomerase, which can advantageously be selected from PDI, calsequestrin and other PDI-related proteins comprising, but not limited to ERp72, ERp57, ERp60, ERp44, ERp5, ERp27 and PDIR, preferably PDI;
c) adapting the culturing conditions by one or more selected from the following: lowering culturing temperature and/or optimizing the culturing medium, including but not limited to reduction of methanol feed for hosts requiring a methanol feed, lowering conductivity of the culture medium, addition of yeast extract and/or peptone, all as further described herein, or any combination thereof; and combinations of any of a) through c); ii) maintaining said host or host cell under conditions that are such that said host or host cell expresses and/or produces the domain antibody, optionally followed by: iii) isolating and/or purifying the secreted domain antibody from the medium.

In one embodiment of the invention, the conditions that promote the formation of a disulfide bridge are applied at step ii).

Accordingly, said method comprises at least the steps of: i) cultivating a host or host cell under conditions that are such that said host or host cell will multiply; ii) maintaining a host or host cell under conditions that are such that said host or host cell expresses and/or produces the domain antibody and that promote the formation of a disulfide bridge, e.g. at least including the following:
a) addition of oxidizing agents, preferably oxidizing metal ions, preferably one or more selected from $Cu^{2+}$, $Fe^{2+}$, $Fe^{3+}$ and $Zn^{2+}$;
b) enhancing expression of a thiol isomerase, which can advantageously be selected from PDI, calsequestrin and other PDI-related proteins comprising, but not limited to ERp72, ERp57, ERp60, ERp44, ERp5, ERp27 and PDIR, preferably PDI;
c) adapting the culturing conditions by one or more selected from the following: lowering culturing temperature and/or optimizing the culturing medium, including but not limited to reduction of methanol feed for hosts requiring a methanol feed, lowering conductivity of the culture medium, addition of yeast extract and/or peptone, all as further described herein, or any combination thereof; and combinations of any of a) through c; optionally followed by: iii) isolating and/or purifying the secreted domain antibody from the medium.

In one embodiment of the invention, the conditions that promote the formation of a disulfide bridge are applied after step ii). In one embodiment of the invention, the conditions that promote the formation of a disulfide bridge are applied before step iii).

Accordingly, the method for producing a domain antibody in a non-*E. coli* host, preferably yeast at least comprises the steps of: i) cultivating a host or host cell under conditions that are such that said host or host cell will multiply; ii) maintaining a host or host cell under conditions that are such that said host or host cell expresses and/or produces the domain antibody; maintaining the domain antibody obtained in step ii) under conditions that promote the formation of a disulfide bridge e.g. under following conditions:
  a) addition of oxidizing agents, preferably oxidizing metal ions, preferably one or more selected from $Cu^{2+}$, $Fe^{2+}$, $Fe^{3+}$ and $Zn^{2+}$;
  b) enhancing expression of a thiol isomerase, which can advantageously be selected from PDI, calsequestrin and other PDI-related proteins comprising, but not limited to ERp72, ERp57, ERp60, ERp44, ERp5, ERp27 and PDIR, preferably PDI;
  c) adapting the culturing conditions by one or more selected from the following: lowering culturing temperature and/or optimizing the culturing medium, including but not limited to reduction of methanol feed for hosts requiring a methanol feed, lowering conductivity of the culture medium, addition of yeast extract and/or peptone, as is further described herein, or any combination thereof;
  d) refolding the domain antibody in the presence of redox-buffer, preferably in the additional presence of denaturant, for example refolding the domain antibody in the presence of denaturant and redox-buffer using 2M guanidinium hydrochloride and 1:5 mM/mM cystamine/cysteamine;
  e) treating the domain antibody by oxygenation, increasing temperature, or increasing pH or any combination thereof, for example treating the domain antibody by increasing the temperature to 40-60° C., preferably 55° C., and/or increasing pH to pH 8-9, optionally combined with oxygenation by purging with oxygen; and
  f) combinations of any of a) through e); optionally followed by: iii) isolating and/or purifying the secreted domain antibody from the medium.

The present invention also encompasses applying the conditions that promote the formation of a disulfide bridge at or after step iii).

Accordingly, the method for producing a domain antibody in a non-*E. coli* host, preferably yeast at least comprises the steps of: i) cultivating a host or host cell under conditions that are such that said host or host cell will multiply; ii) maintaining a host or host cell under conditions that are such that said host or host cell expresses and/or produces the domain antibody; iii) isolating and/or purifying the secreted domain antibody from the medium and applying conditions that promote the formation of a disulfide bridge e.g. under following conditions:
  a) addition of oxidizing agents, preferably oxidizing metal ions, preferably one or more selected from $Cu^{2+}$, $Fe^{2+}$, $Fe^{3+}$ and $Zn^{2+}$;
  d) refolding the domain antibody in the presence of redox-buffer, preferably in the additional presence of denaturant, for example refolding the domain antibody in the presence of denaturant and redox-buffer using 2M guanidinium hydrochloride and 1:5 mM/mM cystamine/cysteamine;
  e) treating the domain antibody by oxygenation, increasing temperature, increasing pH, or high pressure or any combination thereof, for example treating the domain antibody by increasing the temperature to 40-60° C., preferably 55° C., increasing pH to pH 8-9, and/or subjecting the domain antibody to high pressure, for example 250-10000 bar, such as about 1000 to 2000 bar, optionally combined with oxygenation by purging with oxygen; and
  f) combinations of any of a) through e).

The present invention also relates to the combination of any of the above. For example, the present invention relates to culturing and maintaining the non-*E. coli* host under conditions that prevent or reduce the formation of the product related variant lacking at least one disulfide bridge, in combination with maintaining the domain antibody under conditions that lead to the removal or reduction of the product related variant. Suitable further combination can readily be envisaged by the skilled person on the basis of the teaching of the present application.

In the present invention, the host can be removed from the culture medium by routine means. For example, the host can be removed by centrifugation or filtration. The solution obtained by removal of the host from the culture medium is also referred to as culture supernatant, or clarified culture supernatant.

According to the present invention domain antibodies can be purified by standard methods from culture supernatant. Standard methods include, but are not limited to chromatographic methods, including size exclusion chromatography, hydrophobic chromatography, ion exchange chromatography, and affinity chromatography. These methods can be performed alone or in combination with other purification methods, e.g. precipitation or gel electrophoresis. The skilled person can devise suitable combinations of purification methods for domain antibodies on the basis of common general knowledge. For specific examples the art cited herein is referred to. It is envisaged that any of the above conditions a), d), e), f), or a combination thereof, that promote the formation of a disulfide bridge, can also be applied at or between any step of these purification methods. In one embodiment, any of the above conditions a), d), e), f), or a combination thereof may be applied as part of a chromatographic purification procedure, e.g. on the domain antibodies attached to a stationary phase of a chromatographic column. Examples of representative chromatographic refolding processes may include size exclusion (SEC); solvent exchange during reversible adsorption on protein A column or MEP HyperCel™ column; hydrophobic interaction chromatography (HIC); reversed-phase chromatography (RPC); ion exchange chromatography (IEX); or the use of any resin suitable for domain antibody purification. The on-column refolding is attractive because it is easily applied during preparative chromatographic steps.

The conditions that promote the formation of a disulfide bridge may be applied on the column on a partially or highly purified preparation of domain antibody. The conditions can also be applied during another step, such as on a solid phase or during filtering or any other step in purification.

In one exemplary embodiment, domain antibodies can be purified from culture supernatant by a combination of affinity chromatography on Protein A, ion exchange chromatography and size exclusion chromatography. Reference to any "step of purification", includes, but is not limited to these particular methods.

More specifically, domain antibodies can be purified from culture supernatant using a process wherein the clarified supernatant (obtained by centrifugation) is captured on a Protein A resin; followed by a SOURCE 15S (GE Healthcare) cation exchange chromatography step and a Superdex 75 (GE Healthcare) SEC step.

In the following, particular examples of conditions that promote the formation of disulfide bonds suitable for the methods according to the present invention are discussed in more detail. Applying these conditions will also be referred to as "treatment" of the domain antibody.

The skilled person can readily determine the suitable treatment time for any of the method steps described below. The effects of the treatment, i.e. the reduction of the product related variant can be monitored by means described herein, e.g. RP-HPLC. Typical treatment times will range from 0.5 h to overnight treatment. In some instances treatment times will, however, be in the range of 2 to 4 weeks, as set forth below. Preferably, the treatment time will range between 1 and 12 h, more preferably 1 to 6 h, and most preferably 1 to 3 h. In exemplary embodiments of the invention, the treatment time may be 1, 2, 3, 4, 5, or 6 h.

The treatment temperature will depend on the stage of applying the treatment. If the treatment is performed during the culturing phase of the host, the treatment temperature will be the same as the culturing temperature, or below the culturing temperature. The skilled person knows suitable culturing temperatures for different hosts. If the treatment is performed in the presence of the host but at a reduced temperature, the temperature may be e.g. 5° C. below the culturing temperature usually employed for the respective non-*E. coli* host. Exemplary treatment temperatures are room temperature (22° C.), 25° C., 30° C. or 37° C.

After removal of the host, the temperature can also be raised up to 70° C., preferably up to 60° C., more preferably up to 55° C. in view of the high temperature stability of domain antibodies, in particular Nanobodies. A preferable treatment temperature is room temperature.

The various treatments can be performed at different pH. If the treatment is performed during the culturing phase in the presence of the host, the pH will be chosen to be suitable for the host. After removal of the host, the pH can be chosen in a wider range, e.g. from pH 3 to 10, preferably 4 to 9. Specific examples of suitable pH comprise a pH of approximately 4, 5, 6, 7, 8 or 9 (each ±0.5).

After removal of the host, the domain antibody may be present in a wide range of suitable buffers. Examples include, but are not limited to PBS or Tris-HCl. The domain antibody may also be present in physiological saline. Preferably the domain antibody is present in a buffer that does not contain any phosphates.

Subsequent to any one, or any combination of treatments according to the present invention, the domain antibody can be transferred to a new buffer system, if desired. The transfer can be accomplished by routine means. For example, the domain antibody can be transferred into PBS by dialysis. The domain antibody may also be transferred into physiological saline. The skilled person can readily chose other suitable buffer systems.

a) Addition of Oxidizing Agents

In one embodiment of the invention, oxidizing agents can be added to promote the formation of disulfide bonds. The agents can be added during culturing of the host, and/or after removal of the host. In a preferred embodiment of the invention, oxidizing agents are used after removal of the host, i.e. in the context of culture supernatant, or at any stage of purifying the domain antibody.

In the present invention, "oxidizing agents" are any agents that can be used to promote the formation of disulfide bonds. The skilled person is well aware of agents that promote the formation of disulfide bonds.

Specific non-limiting examples of oxidizing agents comprise metals or metal ions, all agents that can act as a redox couple, all redox proteins (including PDI and proteins having oxidative refolding activities, see e.g. Kimura et al. J. Biol. Chem. 280: 31438, 2005), cofactors such as FAD (flavine adenine dinucleotide), FMN (flavine mononucleotide), NADH (reduced nicotinamide adenine dinucleotide), other oxidizing agents like $H_2O_2$ or DMSO. Oxidizing agents are usually chemical substances with elements in high oxidation numbers (e.g., $H_2O_2$, $MnO_4-$, $CrO_3$, $Cr_2O_7^{2-}$, $OsO_4$) or highly electronegative substances that can gain one or two extra electrons by oxidizing a substance (O, F, Cl, Br, I), oxygen-rich compounds with atoms in the highest possible state of oxidation (e.g. potassium permanganate, potassium nitrate) as well as cations of precious metals.

The present invention considers the use of combinations of oxidizing agents, e.g. the combination of more than one oxidizing metal ion, or the combination of an oxidizing metal ion with one or more further oxidizing agents e.g. as set forth above.

The list of specific examples can be easily expanded by the skilled person on the basis of the teaching of the present invention. The skilled person will also readily understand under which condition which oxidizing agent can suitably be used. Depending on the particular circumstances of exposing domain antibodies to oxidizing agents, the skilled person will select different suitable kinds of oxidizing agents.

For example, the exposure to the oxidizing agent must not damage the domain antibody, and should preferably not lead to structural variants other than such lacking a disulfide bridge. In other words, exposure to the oxidizing agent must be conducted under conditions favoring formation of disulfide bridges without damage to the domain antibody. In this connection the high chemical stability of domain antibodies is of great advantage.

If the skilled person chooses to add oxidizing agents during the culturing of the host, the oxidizing agent must not compromise the ability of the host to divide and/or produce the domain antibody.

In one particular embodiment, the oxidizing agent is oxygen, per se. Thus, the culture of the host and/or culture supernatant and/or the solution of the domain antibody at any purification stage after the host has been removed can be oxygenated. In the latter case, oxygenation can also be combined with increasing the temperature e.g. up to 55° C., and/or increasing pH, e.g. to pH 8 or 9.

In another embodiment of the invention, oxidizing metal ions can be added to the culture per se, or the solution comprising domain antibodies after removal of the host at any stage of purification. Specific non-limiting examples of metal ions comprise $Cu^{2+}$, $Fe^{2+}$, $Fe^{3+}$ or $Zn^{2+}$. The metal ions can be added in the form of a suitable salt, for example as sulfates. A specific non limiting example is $CuSO_4$.

Metal ions, including the above examples, e.g. Cu2+ can be added to the culture of the host, or the domain antibody solution after removal of the host in µM to mM concentrations. Specific examples include a final concentration of the metal ion, e.g. Cu2+ of between 0.001 and 100 mM, preferably 0.01 to 10 mM, preferably 0.1 to 10 mM, preferably 0.15 to 10 mM, preferably 1 to 10 mM, more preferably 1 to 5 mM, for example approximately 0.01 mM, 0.1 mM, 1 mM, 5 mM or 10 mM. In one embodiment, the concentration of metal ions is higher than 100 µM, preferably higher than 120 µM. In one particular embodiment, the solution comprises 1 mM metal ion, preferably Cu2+, more preferably in the form of CuSO4. In one embodiment, the concentration of CuSO4 is not between 5 µM and 100 µM.

The above concentrations can also be used for other oxidizing agents. If a combination of oxidizing agents is used, the end concentration of each oxidizing agent by itself may reside within the concentration ranges specified above.

The said concentrations can be applied in the culture medium or the solution comprising domain antibodies after removal of the host at any stage of purification. In case the metal ion is added to the culture medium, the skilled person can readily ascertain a concentration which leads to a reduction or abolishment of the product related variant, whilst it does not affect viability of the host, in particular does not affect the capacity to grow and/or produce domain antibody.

According to the invention, oxidizing agents, in particular metal ions, can be applied to pure domain antibodies, or semi-purified samples (e.g. domain antibody having a purity of >80%, more preferably >90%, more preferably >95%) or on material that is present in the un-clarified culture broth and/or in clarified culture medium. According to the invention even in such less pure protein mixtures the variant can be reduced or removed by treating the samples with the oxidizing agent. In one embodiment, the oxidizing agent, in particular CuSO4, is not added to the culture medium. In one embodiment, the oxidizing agent is applied to the domain antibody attached to a stationary phase of a chromatographic column, as described herein.

The temperature at which the oxidizing agent is added depends on the stage of addition. During culture, the culturing temperature will be applied. After removal from the host, higher temperatures can be employed, if desired. In a preferred embodiment, the temperature will be room temperature after removal of the host.

The oxidizing agent can be added to any suitable buffer. It may be necessary to select a buffer which does not form precipitating salts with the oxidizing agent. For example, the addition of CuSO4 to PBS may result in the formation of precipitates. In this case, the skilled person will select another suitable buffer, e.g. Tris-HCl, which does not form a precipitate with Cu2+.

The treatment duration can be readily determined by the skilled person, e.g. by monitoring the reduction of the product related variant. The treatment may extend over several phases, for example it may extend from the culturing phase of the host to one or several of the purification stages of the domain antibody. Alternatively, the treatment may be performed e.g. in a single step of domain antibody purification. Preferably, the oxidizing agent is used during an early step of antibody purification. Once all disulfide bridge (s) have formed to convert the product related variant into the desired product, this structure will be stable under standard conditions (e.g. in buffers like PBS or Tris-HCl, pH 4 to 10). Thus, if the product related variant is converted into the desired product at an early stage of the purification procedure, the variant will not spontaneously reoccur. Thus, the remainder of the purification method can be performed on the homogeneous desired product. Moreover, the oxidizing agent can be removed by the purification steps following the step including treatment with the oxidizing agent. This has the additional advantage that the final product will be free of the oxidizing agent.

In a preferred embodiment, domain antibodies are treated at any stage after removal of host by addition of a metal salt, preferably CuSO4 to a final concentration of 1 mM at room temperature for at least 2h. More preferably, the treatment with a metal ion, e.g. Cu2+ is performed in the clarified culture supernatant at a pH of 4 for at least 2 h.

The use of CuSO4 in the context of producing conventional humanized antibodies comprising 16 disulfide bonds by CHO cells has previously been reported (Chaderjian et al. Biotechnol. 21: 550, 2005). In this instance, 5-100 µM CuSO4 were added to a culture of CHO cells. At the highest concentration, viability of the host was already compromised.

In one particular embodiment of the invention, the non-*E. coli* host is not CHO, when the oxidizing agent is CuSO4. In one embodiment, the non-*E. coli* host is not CHO, when CuSO4 is added at a concentration of 5 to 100 µM. In one embodiment CuSO4 is not added to the culture medium at a concentration ranging from 5 to 100 µM.

According to the present invention, the addition of an oxidizing agent suitable for promoting the formation of disulfide bridges can result in the fast and complete removal of the product related variant lacking at least one disulfide bond. In this connection, removal means that the variant forms the missing disulfide bridge(s) and thus becomes structurally identical with the desired domain antibody.

b) Increasing a Thiol Isomerase, Preferably Protein Disulfide Isomerase, in the Host The enzyme Protein Disulfide Isomerase (PDI), a 55 kDa protein, has been shown to be a catalyst in protein folding, disulfide bond formation and isomerization in the endoplasmic reticulum (ER) of eukaryotic cells (Freedman et al. Trends Biochem. Sci. 19: 331, 1994; Wilkinson et al. 2005, J. Biol. Chem. 280: 11483). PDI is involved in structure formation of immunoglobulins in vivo. (Gonzalez et al. Biotechnol. Prog., 17: 217, 2001; Nilsson et al. Immunol. Lett. 94: 83, 2004). In hosts like *Saccharomyces* further proteins having oxidative refolding activities have been reported (Kimura et al., J. Biol. Chem. 280: 31438, 2005).

Co-expression of conventional antibodies or their fragments, like Fab or scFv with PDI has been applied to increase secretion rates and/or levels of functional product in hosts like *E. coli, Saccharomyces*, CHO, baculovirus transfection of insect cells, or *Pichia* (Humphreys et al. FEBS Lett. 380: 194, 1996; Hsu et al. Protein Expr. Purif. 7: 281, 1996; Shusta et al. Nat. Biotechnol. 16: 773, 1998; Xu et al. Metabolic Engineering 7: 269, 2005; Borth et al. Biotechnol. Prog. 21: 106, 2005; Mohan et al. Biotechnology and Bioengineering 98: 611, 2007; Damasceno et al. Appl. Microbiol. Biotechnol. 74: 381, 2007; Gasser et al. Appl. & Env. Microbiol. 73: 6499, 2007). In these methods, co-expression with PDI was applied to obtain increased rates and/or levels of functional product.

In contrast, co-expression with PDI is not a requirement for efficient production of domain antibodies in e.g. *E. coli*. Good yields of fully functional domain antibodies have been achieved by recombinant expression in *E. coli*.

However, in a fraction of the domain antibodies, in particular Nanobodies obtained from non-*E. coli* hosts, in particular yeasts, more particularly *Pichia*, the presence of free thiol was observed, due to unpaired cysteine residues. This finding was entirely unexpected, because most of these domain antibodies, in particular Nanobodies, were still functional and well-expressed.

Consequently, in a further embodiment of the invention, expression of a thiol isomerase can be enhanced in the host by commonly known means, including e.g. use of suitable control sequences, e.g. a strong promoter, and/or increasing the gene dose, e.g. by increasing the copy number of the respective gene. The copy number can be increased e.g. by introducing genetic constructs suitable for expression of thiol isomerase. If the host already comprises endogenous thiol isomerase, the additional presence of the plasmid will increase the overall copy number. In this instance, the thiol isomerase may be the same or different to the thiol isomerase endogenous to the host. In case the host does not endogenously contain thiol isomerase, the introduction of exogenous thiol isomerase, e.g. in the form of a plasmid or vector, also increases the copy number in this host, even if present as a single copy.

Moreover, genetic constructs that can multiply independently of the host genome and are present in multiple copies in the host can be used. For example, multi copy plasmids or vectors may be present in copy numbers between 5 and 50 in the host cell.

The skilled person will know a multitude of possibilities of enhancing the expression of thiol isomerase, all of which are encompassed by the present invention. The skilled person can also readily ascertain on the basis of routine means that the expected correlation between enhanced gene dose and enhanced enzymatic activity is present. Most importantly, the reduction of the product related variant can be monitored.

Hence, the domain antibody can be co-expressed in the host with a thiol isomerase. This approach can be taken alone or in combination with any other approach to avoid, reduce or remove product related variants as described herein.

Specific examples of thiol isomerases include, but are not limited to calsequestrin and other PDI-related proteins like ERp72, ERp57, ERp60, ERp44, ERp5, ERp27 and PDIR, preferably protein disulfide isomerase (PDI).

The thiol isomerase and the domain antibody can be expressed from the same or different nucleic acids, e.g. the same or different vector or plasmid. A nucleic acid suitable for transforming a host and/or expression of the domain antibody in the host is also referred to as genetic construct. Such a genetic construct will oftentimes comprise regulatory elements, such as suitable promoters, enhancer elements polyadenylation sequences, etc.

Accordingly, the present invention also relates to nucleic acids or genetic constructs encoding a domain antibody and a thiol isomerase. Furthermore, the present invention relates to hosts comprising such genetic constructs or nucleic acids.

The skilled person can introduce the nucleic acids of the invention into hosts by routine measures, e.g. by transformation. The skilled person can then select suitable host cells comprising the nucleic acids, e.g. by monitoring the expression of the thiol isomerase on the nucleic acid and/or protein level. A strain with a satisfactory level of expression will be selected. A high expression of thiol isomerase is desirable, however, it should not be so high as to result in competition with expression of the domain antibody. This can be determined by routine methods.

For further guidance, the skilled person can consult the exemplary sequence of PDI provided in the experimental part of the application, the GenBank entry NP_009887, or sequences reported in the art (see e.g. Wilkinson et al. J. Biol. Chem. 280: 11483, 2005; Mayer et al. 341: 1077, 2004). Further proteins having oxidative refolding activities are known in the art and can be used in the context of the present invention, alone or preferably in combination with the thiol isomerases set forth above (Kimura et al. J. Biol. Chem. 280: 31438, 2005). Also considered for expression in combination with thiol isomerases are factors known to enhance heterologous protein secretion in yeasts, as described e.g. in Gasser et al. (Appl. Environm Microbiol. 73: 6499, 2007) or Damasceno et al. (Microbiol. Biotechnol. 74: 381, 2007).

Also exemplified are methods to clone PDI in a suitable vector and transform hosts, as well as selection of suitable transformants. The skilled person can select any one or more of these aspects to arrive at embodiments of the invention, alone or in combination with any of the general teaching of the application.

According to the invention, the coexpression of a thiol isomerase with a domain antibody can result in the significant reduction of the product related variant. The invention includes the further treatment of domain antibodies obtained from expression in hosts co-expressing a thiol isomerase to reduce or remove the product related variant.

c) Adapting the Culturing Conditions

In a further embodiment of the invention, which can be employed alone or in combination with any other embodiment as described herein to reduce the formation of product related variants lacking at least one disulfide bond, the culture conditions can be adapted.

The skilled person knows standard culturing conditions for non-*E. coli* hosts suitable for recombinant production of domain antibodies.

As a specific example, the yeast *Pichia*, in particular *P. pastoris*, is typically cultured in glycerol fed batches and induction is initiated by the addition of methanol. The standard protocol is the Invitrogen protocol, expression at 30° C. in basal salt medium with a methanol feed rate of 10 ml/L*h. Other methods for the culturing of non-*E. coli* host will be know to the skilled person and are e.g. described in Methods in Molecular Biology™, *Pichia* protocols, second edition, Humana Press.

As compared to standard conditions, including, but not limited to the ones exemplified for *P. pastoris*, one or more selected from the following adaptations of culturing conditions can be applied: reduction of methanol feed, lowering conductivity of the culture medium, lowering culturing temperature, addition of yeast extract and/or peptone, or any combination thereof.

The following detailed description will be given in the context of the standard protocol (the Invitrogen protocol) for culturing *P. pastoris*, as set forth above. The skilled person will readily be in a position to adapt this teaching to the standard protocols used for other non-*E. coli* hosts. For example, where the standard temperature for culturing *P. pastoris* is 30° C., a reduction in culturing temperature means e.g. 25° C. It is clear to the skilled person that for a non-*E. coli* host, the standard culturing temperature of which is 37° C., 32° C. or 30° C. may represent a reduced culturing temperature.

Without wanting to be bound by theory, it is envisaged that culturing conditions which reduce metabolic stress to the non-*E. coli* host will reduce or abolish the formation of the product related variant lacking at least one disulfide bond.

One possible adaptation of the culturing conditions relates to a reduced methanol feed. An example of reduced methanol feed is a reduction by 30%, 50%, 70% or 80% as compared to the standard protocol, for example ≤7 ml/l*h, ≤5 ml/l*h, ≤4 ml/l*h, ≤3 ml/L*h.

A further adaptation of the culturing conditions, to be applied alone or together with reduced methanol feed, or any other embodiment of the invention described herein, is the reduction of conductivity of the culturing medium, e.g. the basal salt medium. Such reduction can be a reduction by 30%, 50%, 70% or 80% as compared to the standard protocol, for example ≤28 mS:cm, ≤20 mS:cm, ≤12 mS:cm.

A further adaptation of the culturing conditions, to be applied alone or together with one or more of reduced methanol feed, reduced conductivity, and/or any other embodiment of the invention described herein, is lowering the culturing temperature. For example, the culturing temperature can be lowered by 2, 3, 4, 5, or 6° C. In a preferred embodiment the culturing temperature is lowered by 5° C., e.g. from 30° C. to 25° C.

A further adaptation of the culturing conditions, to be applied alone or together with one or more of reduced methanol feed, reduced conductivity, lowering the culturing temperature and/or any other embodiment of the invention described herein, is the addition of yeast extract and/or peptone. For example, yeast extract and/or peptone can be added at a concentration in the feed of 0 to 20% to the culture medium.

For the overall production process the addition of yeast extract and/or peptone has the additional advantage of strongly reducing, or completely avoiding the occurrence of fragments of domain antibodies. This additional structural variant is likely formed by proteolytic activity. Without wanting to be bound by theory, the addition of yeast extract and/or peptone may provide alternative substrates for proteases, such that the formation of degraded domain antibodies is reduced or avoided all together.

A further adaptation of the culturing conditions, to be applied alone or together with one or more of reduced methanol feed, reduced conductivity, lowering the culturing temperature, addition of yeast extract and/or peptone, and/or any other embodiment of the invention described herein, is the use of an optimized culturing medium. For example, instead of basal salt medium, Rich medium as defined in the experimental section can be used.

The skilled person can readily combine the above measures such as to devise optimized culturing conditions. The level of product related variant under the different conditions can be readily determined e.g. by RP-HPLC.

The above measures, alone or in a suitable combination, can result in a significant reduction of product related variant. For example, as compared to a standard protocol (e.g. the Invitrogen protocol), resulting in 15% of product related variant, the above measures can lead to a reduction to between 1 and 4% product related variant, preferably 1% product related variant or less.

d) Refolding in the Presence of Denaturant and Redox-Buffer

As outlined above, the adaptation of the culturing conditions may result in a considerable reduction of the product related variant. However, there may still be residual product related variant. Similarly, domain antibodies may have been produced by standard protocols or in procedures optimized for titer in non-*E. coli* hosts, and may comprise 15-25% of product related variant.

Hence, in a further embodiment the present invention relates to the refolding of the product related variant in the presence of a denaturant and under conditions suitable for the formation of the missing disulfide bond(s). This may be applied alone or together with one or more of the other embodiments of the invention as described herein.

To achieve formation of the missing disulfide bridge, the domain antibody preparation is advantageously treated with a denaturant. This will typically be done after separation from the host, in culture supernatant or after any of the different purification steps routinely applied. In a preferred embodiment this treatment will be applied to purified domain antibody. Suitable denaturants include GdnHCl (Guanidinium hydrochloride, also abbreviated GuHCl) or urea. The denaturant has to be applied in a high enough concentration to achieve partial denaturation of the product related variant and at the same time will unfold the intact domain antibody. For example, 0.125 to 2 M GdnHCl, preferably 1 M, more preferably 2 M GdnHCl; or 1-3 M urea, preferably 2 M, more preferably 3 M, can be employed. The skilled person will know other suitable denaturants having a comparable effect on the product related variant.

Moreover, refolding of the variant and the intact domain antibody has to be performed in the presence of a suitable redox buffer. The skilled person can readily select suitable redox buffers on the basis of the teaching of the present application. Specific examples of suitable redox buffers comprise mixtures of cystamine/cysteamine. Suitable ratios are in the range of 1:5 mM/mM to 5:1 mM/mM, preferably 1:5 mM/mM cystamine/cysteamine.

In one preferred embodiment, refolding is performed in 2 M GdnHCl and 1:5 mM/mM cystamine/cysteamine. Under these conditions a complete refolding and formation of the lacking disulfide bond and the refolding of the intact domain antibody can be achieved in the course of approximately 2 h at room temperature.

The domain antibody can be unfolded by exposure to the denaturant, and subsequently exposed to the redox buffer. Alternatively, the denaturant and redox buffer can be used at the same time.

Exposure to the denaturant and redox buffer can be achieved by standard techniques, exemplified, but not limited to addition of denaturant/redox buffer to the solution of the domain antibody to achieve a suitable final concentration, by dialysis, or by buffer exchange techniques. The contacting with the denaturant and redox buffer can also be performed with domain antibodies attached to a stationary phase of a chromatographic column, while the denaturant and redox buffer are part of the mobile phase.

Subsequent to refolding, the domain antibody can be transferred to a new buffer system, if desired. The transfer can be accomplished by routine means. For example, the domain antibody can be transferred into PBS by dialysis. The skilled person can readily chose other suitable buffer systems.

e) Oxygenation, Increasing Temperature, Increasing pH, High Pressure

After separation of the domain antibody from the host, the domain antibody can be treated in several ways that increase the formation of disulfide bridges.

The domain antibody solution can be oxygenated. For example, the solution can be purged with oxygen gas. Alternatively, compounds liberating oxygen can be added. Suitable compounds are known to the skilled person. The amount of soluble oxygen in the solution is needed to maintain the fully oxidized form of the domain antibody, depletion of the amount of oxygen supply to the solution by, for example a nitrogen gas overlay during the fill process, will not be preferred.

Oxygenation can be performed at a suitable temperature, e.g. between room temperature and 70° C., preferably between 37° C. and 60° C., advantageously at 55° C. Whereas oxygenation alone can lead to the reduction of the product related variant, the combination of oxygenation and increased temperature will increase the rate by which the missing disulfide bridge(s) are formed.

Treatment duration can be chosen as appropriate, e.g. between 2 hours and 48 hours, advantageously 3-24 h, preferably 5 to 12 h. The skilled person can monitor the progress of disulfide bridge formation e.g. by RP-HPLC to determine a suitable treatment duration.

The buffer system is not limited, provided it is suitable for oxygenation. Standard buffer systems like PBS or Tris-HCl can be used.

As an alternative to oxygenation, domain antibodies can be treated by increasing the temperature alone, i.e. without oxygenation. Increasing the temperature to e.g. 70° C., preferably 40-60° C., more preferably 55° C. will result in the reduction of the product related variant by formation of the missing disulfide bridge(s).

Treatment duration can be chosen as appropriate and may range from several days to several weeks, for example 2 to 4 weeks at 37° C. At higher temperatures, treatment duration can be reduced. A reduction in the product related variant can be observed, for example, after treating the domain antibody at 50° C. overnight, preferably 1 to 2 days, preferably 3 to 7 days.

The above measures of oxygenation and/or increasing temperature can furthermore be combined with increasing the pH. Examples of an increased pH are e.g. in the range of pH 7.5 to 10, more specifically approximately pH 8 or 9. Said increase of the pH will also lead to the reduction of product related variants on its own, i.e. without combination with oxygenation and/or increased temperature.

As an alternative to oxygenation, increasing temperature, increasing pH and/or in addition to these measures, domain antibodies can be subjected to high pressure. Increasing the pressure to 250-10000 bar, preferably 500-5000 bar, such as 1000-4000 bar, e.g. about 1000-about 2000 bar will result in reduction of the product related variant by formation of the missing disulfide bridge(s).

Treatment duration can be chosen as appropriate and may range from one or a few hours to 50 hours, for example about 20-25 hours at room temperature.

It can be appreciated that combinations of one or more of the measures of oxygenation, increased temperature, increased pH and high pressure will enhance the formation of disulfide bridge(s) in the product related variant, such that the variant is reduced more quickly and/or to a greater extent.

One or more of the above measures can also be applied to the domain antibodies attached to a stationary phase of a chromatographic column as described herein.

f) Removal of Product Related Variant by Binding to Activated Thiol-Sepharose and/or RP-HPLC The above described measures, alone or in combination, aim at reducing the product related variant by forming the missing disulfide bridge(s). In other words, these measures lead to the conversion of the product related variant into the desired product. The advantages are self evident, in that a significant proportion of the starting material may be present in the form of the variant, and the conversion into the desired product increases the yield of the overall process.

Nevertheless, in a further embodiment, which can be used alone or in combination with one or more of the above measures or treatments, the present invention also relates to the removal of product related variant. In this context, removal means the physical separation from the desired product, and is distinct from the conversion of the variant into the desired product by formation of the lacking disulfide bridge(s).

The skilled person can utilize a range of standard techniques for removing the product related variant by virtue of the presence of free thiol groups which are present in the variant in view of the lacking disulfide bridge(s). These free thiol groups can be used for binding the variant to reactive groups which are, for example, immobilized on a suitable carrier. One example of suitable reactive groups are thiol groups. Thus, thiol immobilized on a carrier, e.g. a substrate suitable for chromatography, can be used for binding the free thiol in the variant. Standard techniques, comprising, but not limited to chromatography, can be used for separating the bound variant from the desired product.

Free thiol groups can be used for separation of the product related variant in case the desired domain antibody does not contain free thiol groups once all disulfide bridges have been formed. For example, if the domain antibody contains one or more cystein(s) which do not participate in disulfide bridge formation in the desired product, binding to thiol groups will not distinguish between the product and the product related variant.

Preferably, the domain antibodies are exposed to the reactive groups under denaturing conditions. This ensures that all free thiols present in the product related variant will be accessible to the reactive groups. Denaturing conditions as exemplified in the context of the refolding strategy (denaturant+redox buffer) can be employed, albeit under omission of the redox buffer. Examples include Guanidinium hydrochloride and urea at the concentrations specified hereinabove. In addition, conditions as used in the examples section (e.g. 6M urea) can be applied.

A further approach to remove the product related variant according to the present invention resides in the use of RP-HPLC. Amongst several chromatographic methods discussed in the experimental part of this application, RP-HPLC has surprisingly shown to have a good resolution for the desired domain antibody and the product related variant. Hence, RP-HPLC can not only be used to monitor the effects of various treatments according to the present invention, and to evaluate the quality of a domain antibody product in terms of product homogeneity. In addition, RP-HPLC can be used for physical separation of the variant from the desired product.

Removal of the product related variant by physical separation from the desired domain antibody can be performed alone, or in combination with any of the other embodiments of the invention as described herein. Advantageously in the case of a combination, one or more methods or treatments that reduce the amount of product related variant by formation of the missing disulfide bridge(s) will be performed first, followed by a step of removing the remaining variant by physical separation.

Domain Antibody of the Invention

The present invention also relates to the domain antibody obtainable by the methods of the invention as described herein. It is characterized by a reduced level, or the complete absence, of the product related variant lacking at least one disulfide bridge. For example, the domain antibody obtainable by the methods of the present invention comprises 0-5%, more preferably 0-4%, 0-3%, 0-2% or 0-1% product related variant. Most preferably, the domain antibody of the present invention will be free of the product related variant.

The skilled person can readily determine the proportion of product related variant—as a % of the total—e.g. by RP-HPLC as described herein.

In other words, the domain antibody obtainable by the methods of the present invention is characterized by an improved structural homogeneity as compared to prior art preparations. In particular, prior art preparations may comprise 15-25%, or even higher proportions of product related variant.

In view of the improved structural homogeneity, the domain antibody obtainable by the method of the present invention is advantageous as compared to prior art preparations. For example, the domain antibody of the present invention is advantageous for therapeutic applications. In the connection of therapeutic antibody use, structural homogeneity is of foremost clinical and regulatory importance. Even though the product related variant surprisingly is fully functional, its presence in therapeutic preparations is undesired.

Accordingly, the present invention also relates to pharmaceutical preparations and other compositions comprising the domain antibody obtainable by the methods of the present invention. The present invention also relates to the medical use of the domain antibody obtainable by the method of the present invention.

The skilled person can readily formulate pharmaceutically suitable formulations on the basis of common general knowledge. Moreover, the references specifically dealing with domain antibodies, which are cited herein, are explicitly referred to. Without limitation, formulations for standard routes of application can be prepared, including formulations for nasal, oral, intravenous, subcutaneous, intramuscular, intraperitoneal, intravaginal, rectal application, topical application or application by inhalation.

Based on the present invention, the skilled person can also readily devise suitable methods of treatment characterized by the use of a therapeutically effective amount of the domain antibody of the present invention.

EXAMPLES

The experimental section describes the surprising identification of a product related variant that occurs upon expression of single domain antibodies, like Nanobodies, in non *E. coli* hosts, such as *Pichia pastoris*. Also described is the analysis and elimination of the product related variant.

The variant does not occur in *E. coli*.

Several standard chromatographic methods cannot separate the "intact" material from the variant; neither a cationic ion exchange (IEX) chromatographic step, nor a Hydrophobic Interaction Chromatography showed any resolving power for the variant. Moreover, most of the variants are fully functional as determined by binding (e.g. Biacore, ELISA) to their respective ligands. In other words, by standard analytical techniques the non-*E. coli* produced material (comprising the variant) was indistinguishable from *E. coli* produced material (without the variant).

For these reasons, finding the product related variant was surprising, in the first place.

Analysis of the product related variant demonstrates that the variant—which was initially identified as 'post-peak' in the RP-HPLC analysis—constitutes a population of Nanobody molecules in which one of the canonical disulfide bonds has not been formed. In one instance, the disulfide bond has not been formed in one of the Nanobody building blocks of a composite Nanobody comprising three Nanobody subunits with two different specificities. Evidence that the product related variant lacks a disulfide bond came from the Total Mass Measurements by mass spectrometry, the measurement of free thiol in the sample and the binding of the variant to a thiol-affinity resin and the spontaneous formation of the disulfide bond in the variant upon storage.

Multiple ways for avoiding occurrence of the variant in the first place and/or removing the variant after it has been formed are exemplified.

For example, the formation of the variant during the culturing stage can be reduced or avoided by one or more measures selected from low methanol feed, a low conductivity medium, low culturing temperature, the addition of yeast extract and/or peptone, and the overexpression of Protein Disulfide Isomerase (PDI).

Moreover, the variant can be removed from the obtained product by one or more selected from binding to thiol Sepharose under denaturing conditions, RP-HPLC, storage at elevated temperatures, oxygenation, increasing pH, refolding in the presence of denaturants and a redox buffer, and the addition of oxidizing agents, such as oxidizing metal ions, specifically $Cu^{2+}$, $Fe^{2+}$, $Fe^{3+}$ and/or $Zn^{2+}$.

The addition of oxidizing agents, in particular oxidizing metal ions, e.g. copper, iron or zinc ions, can be performed at any stage of production, i.e. during the culture stage, during various clarification and purification steps, and in the final purified product.

These measures, alone or in combination, avoid having a large proportion of active—but potentially unstable product variant in the final drug substance after the purification.

RANKL008a was previously described in WO 2008/142164 and is a trivalent bispecific Nanobody consisting of three humanized variable domains of a heavy-chain llama antibody, of which two identical subunits are specific for binding to RANKL while the remaining subunit binds to Human Serum Albumin (HSA). The subunits are fused head-to-tail with a G/S linker in the following format: 13H5-9GS-Alb8-9G5-13H5 and having the following sequence (SEQ ID NO: 6):

EVQLVESGGGLVQPGGSLRLSCAASGFTFSSYPMGWFRQAPGKGREFVSS

ITGSGGSTYYADSVKGRFTISRDNAKNTLYLQMNSLRPEDTAVYYCAAYI

RPDTYLSRDYRKYDYWGQGTLVTVSSGGGGSGGGSEVQLVESGGGLVQPG

NSLRLSCAASGFTFSSFGMSWVRQAPGKGLEWVSSISGSGSDTLYADSVK

GRFTISRDNAKTTLYLQMNSLRPEDTAVYYCTIGGSLSRSSQGTLVTVSS

GGGGSGGGSEVQLVESGGGLVQPGGSLRLSCAASGFTFSSYPMGWFRQAP

GKGREFVSSITGSGGSTYYADSVKGRFTISRDNAKNTLYLQMNSLRPEDT

AVYYCAAYIRPDTYLSRDYRKYDYWGQGTLVTVSS

In some instances the RANKL008a is followed by the acronym Pic which stands for the protein that is expressed in *Pichia pastoris* or by the acronym Omp which stand for material expressed in *E. coli* through periplasmic expression.

It is demonstrated that material containing product related variants of e.g. RANKL008a (the variant lacking one or two disulfide bridges is also referred to as RANKL008a-PRV-SS or PRV-RANKL008a) surprisingly does not show a reduced potency; binding to both the ligands, i.e. RANKL and Human Serum Albumin, surprisingly is not impaired and the variant is fully functional. Moreover evidence is presented that the disulfide bond is missing in the RANKL binding subunit of this trivalent, bispecific (for RANKL and HSA binding) Nanobody.

The RANKL008a molecule was produced by periplasmic expression in *E. coli* or in *Pichia pastoris* (secreted). Whereas all analytical methodologies and the potency measurements of the *E. coli* and the *P. pastoris* materials demonstrated not to be significantly different, the RP-HPLC showed the presence of a quantitatively important variant lacking a disulfide bridge in the *Pichia* derived material.

It is demonstrated that the occurrence of the RANKL008a-PRV-SS variant is independent of the yeast strain in which the construct is expressed, and no differences between different selected production clones could be identified. Moreover the variant is present already at the initial phases of expression and there is no relative increase during the duration of the expression. There is however a clear correlation between the expression efficiency, the final titer obtained, the feeding strategy applied (methanol feed in particular) and the relative proportion of this variant is such that the higher the expression the higher the relative proportion of the variant.

Refolding in the presence of denaturant and redox-buffer showed clearly that the variant can be converted into intact material containing the expected canonical disulfide bridge. It is also shown that by increasing the temperature, changing the pH and by adding oxidizing agents, like metal ions, the variant could be efficiently and reproducibly converted into intact protein. It is furthermore shown that such measures can be taken at different steps in the process: in the culture broth, clarified supernatant or on purified materials, as exemplified by the addition of an oxidizing agent, specifically a metal ion, more specifically CuSO4.

In a preferable embodiment a process is defined where an oxidizing metal ion, preferably Cu2+, more preferably 1 mM CuSO4 is added to the clarified culture supernatant prior to the loading on the first chromatographic step.

In this section experiments are described, amongst others, that were performed to create other hosts for the expression of RANKL008a and its effect on the PRV-RANKL008a. Moreover for a particular strain it was tested if the PRV-RANKL008a is present in all clones isolated. Over-expression of Protein Disulfide Isomerase (PDI) was explored with the aim of "facilitating" the disulfide bond formation during expression with the aim of reducing the relative proportion of the variant.

Moreover, the fermentation conditions for expression of RANKL008a in *P. pastoris* X-33 strain were explored with the aim to investigate if any of these conditions can reduce the relative proportion of this variant.

Unless described otherwise standard methods of analysis were applied.

Example 1

Fermentative Production of Nanobodies in *P. pastoris* Results in High Quality, Homogeneous Product Production of Nanobodies in lower eukaryotic hosts such as *Pichia pastoris* has been extensively described in WO 94/25591, and is known to result in good quality product.

Accordingly, the comparison of the RANKL008a material expressed in *E. coli* versus that of the materials expressed in *P. pastoris*(X-33 strain) did not reveal any significant differences as can be appreciated from FIGS. 1 to 3.

The material used for comparison has been purified as briefly set forth in the following: The RANKL008a protein is purified from clarified supernatant (obtained by centrifugation) by capturing on a Protein A resin; followed by a Source 15S cation exchange chromatography step and subsequently polished on a Superdex 75 SEC step.

FIG. 1 describes the size exclusion chromatography on *E. coli* material (two different batches denoted as "B5#201207" and "B11#140208") in comparison with the *P. pastoris* material ("Pic P #270308").

As can be seen in particular from the enlarged inset, the material produced and purified from a *P. pastoris* fermentation (also referred to as "*P. pastoris* material") using similar purification protocols resulted in an even more homogeneous material as compared to *E. coli. P. pastoris* material eluted in one peak without any pre- or post peaks. Tailing of the eluted peak was very minor, and much less than observed for the comparable material obtained from *E. coli.*

The size exclusion chromatographic findings could be confirmed by comparison of *E. coli* and *P. pastoris* produced Nanobodies by ion exchange HPLC (cation exchange). The results can be seen in FIG. 2 and the enlargement in FIG. 3. In both figures *P. pastoris* produced Nanobody traces can be identified by the term "Pic". The other batches are *E. coli* produced. In *P. pastoris* produced Nanobodies the peak at 27 min. observed for the two different batches of *E. coli* material was absent, again indicating a better homogeneity of the *P. pastoris* produced material.

Example 2

Nanobodies Produced in *P. pastoris* have Good Functionally as Exemplified by Binding to RANKL or HSA by RANKL008a (No Differences to *E. coli* Produced Material)

RANKL008a binds both to RANKL and to HSA and therefore both functionalities should be tested to compare *E. coli* and *P. pastoris* produced material. The functionality of the RANKL008a can be tested by several methodologies: e.g. a Biacore method for binding to RANKL and HSA was used to allow rapid screening of functionality of binding of RANKL008a to its respective targets. Comparisons of the slopes of the binding are used for relative comparison. Moreover ELISA assays for monitoring the relative potencies for RANKL and HSA were used.

Biacore Experiments for Binding of RANKL008a to RANKL or HSA

Experiments are performed on a Biacore3000 instrument (GE Healthcare). Chips are coated with HSA or RANKL using the Biacore amino coupling kit using NHS/EDC for activation and ethanolamine for de-activation. The CM5 chips (Biacore AB, research grade) were coated with respectively 10 μg/mL HSA (Sigma A3782/085K7541) or 7 μg/mL RANKL (Peprotech Cat#310-01 Lot#1101142) in a 10 mM sodium acetate buffer of pH 4.5. The experimental conditions are summarized in the following table:

TABLE 1 experimental conditions for Biacore experiments

|  | RANKL | HSA |
|---|---|---|
| Flow buffer | HBS-EP* | HBS-EP* |
| Flow Rate (μL/min) | 45 | 45 |
| Injection volume (μL) | 90 | 90 |
| Injection time (sec) | 120 | 120 |
| Dissociation time (sec) | 180 | 180 |
| Regeneration solution | 0.1M H3PO4 | 10 mM Glycine-HCl pH 1.5 |
| Regeneration flow rate (μL/min) | 100 | 100 |
| Regeneration volume (μL) | 5 | 15 |
| Regeneration time (sec) | 3 | 10 |

*HBS-EP: 0.01M Hepes pH 7.4 + 0.15M NaCl, 3 mM EDTA and 0.005% P20 surfactant.

Evaluation is performed using the BIAevaluation software. Slopes are determined using the "General Fit" method and the linear fit model. Initial Binding Rate (IBR) was determined on the slope between 5 and 30 sec. RANKL008a is used at 5 nM on the HSA chip, and at 2 nM on the RANKL chip; the Response Units on the HSA chip are about 5200, for the RANKL chip about 1700.

Two different batches RANKL008a (one produced in *E. coli* B11#140208 and one produced in *P. pastoris* P #270308nr1) were sent over a high density HSA chip at concentrations of 4.5 and 5 nM and slopes of the binding between 5 and 30 sec were determined. In these conditions and concentrations the binding is linear.

TABLE 2

Slopes of the binding of two different RANKL008a batches on a high density HSA chip at respectively 4.5 and 5 nM (three independent dilutions from the stock material).

|  | nM | Slope 1 | Slope 2 | Slope 3 | Aver. Slope | % CV on slope | % binding compared to 5M solution |
|---|---|---|---|---|---|---|---|
| RANKL008a | 4.5 | 2.75 | 2.68 | 2.73 | 2.72 | 1.33 | 92.00 |
| *E. coli* | 5 | 2.97 | 2.94 | 2.96 | 2.96 | 0.52 |  |
| RANKL008a | 4.5 | 2.9 | 2.97 | 2.84 | 2.90 | 2.24 | 89.33 |
| *P. pastoris* | 5 | 3.23 | 3.26 | 3.26 | 3.25 | 0.53 |  |

The % CV on the measured slopes is <2.5%; indicating that a 10% difference can be detected using this analysis, the slopes measured for a 4.5 nM and a 5 nM solution are significantly different.

At the same time these data allow to compare the slopes of the binding curves for the *E. coli* material and the *P. pastoris* material which have a relative percentage binding of 107 and 110% relative to that of the *E. coli* batch for the 4.5 and 5 nM experiments respectively. This difference can be attributed to differences in the protein concentration used for the preparation of the diluted material.

In conclusion these data show that the binding of RANKL008a produced in both expression systems to a high density HSA chip is comparable.

Two different batches RANKL008a (one produced in *E. coli* B11#140208 and one produced in *P. pastoris* P #270308nr1) were sent over a RANKL chip at concentrations of 1.8 and 2 nM, and slopes of the binding between 5 and 30 sec were determined. In these conditions and concentrations the binding is linear.

TABLE 3

Slopes of the binding of two different RANKL008a batches on a RANKL chip at respectively 1.8 and 2 nM (5 independent dilutions from the stock solution).

|  | nM | Slope 1 | Slope 2 | Slope 3 | Slope 4 | Slope 5 | Aver. Slope | % CV on slope | % binding compared to 2M solution |
|---|---|---|---|---|---|---|---|---|---|
| RANKL008a | 1.8 | 1.6 | 1.62 | 1.64 | 1.6 | 1.6 | 1.61 | 1.11 | 92.22 |
| *E. coli* | 2 | 1.74 | 1.75 | 1.72 | 1.77 | 1.76 | 1.75 | 1.10 |  |
| RANKL008a | 1.8 | 1.74 | 1.72 | 1.72 | 1.69 | 1.72 | 1.72 | 1.04 | 90.33 |
| *P. pastoris* | 2 | 1.91 | 1.9 | 1.9 | 1.89 | 1.91 | 1.90 | 0.44 |  |

The % CV on the slopes determined for the binding of RANKL008a to RANKL is low (% CV<1.2%) such that a 10% difference can be detected using this technique. The slopes measured for a 1.8 nM and a 2 nM solution are therefore significantly different.

At the same time these data allow to compare the slopes of the binding curves for the *E. coli* material and the *P. pastoris* material which have a relative percentage binding of 109 and 111% relative to that of the *E. coli* batch for the 1.8 and 2 nM experiments respectively. This difference can be attributed to differences in the protein concentration used for the preparation of the diluted material.

It can be concluded that the RANKL binding of the RANKL008a material produced in both expression systems is comparable.

ELISA

The potency ELISA assay for RANKL binding is an inhibition type assay. Briefly, RANKL008a interacts with the human soluble Receptor Activator of Nuclear Factor κB Ligand (RANKL) and blocks the interaction of this ligand with its human receptor activator of nuclear factor-κB (RANK), thereby preventing signalling though this receptor. In the assay RANKL008a is pre-incubated with a fixed amount of RANKL and RANK-Fc, the mixture is then incubated on an ELISA plate coated with an anti-Fc Nanobody; any residual RANKL not bound to RANKL008a binds to the RANK-Fc immobilized on the plate. Signal is detected by incubating with a biotinylated anti-RANKL antibody which is detected by a Streptavidin coupled to HRP (horse radish peroxidase). This assay is capable of demonstrating the avid binding of the 13H5 sub-units to RANKL and will show if any of the 13H5 building blocks is not functional.

The ELISA developed for HSA binding is based on the direct binding of the RANKL008a to HSA coated on the plate, any bound RANKL008a is detected using an anti-Nanobody-Nanobody labeled with HRP. This assay can detect if binding to HSA is impaired. The potencies measured in both ELISA assays are expressed as relative potencies compared to a reference material.

For the RANKL008a both the RANKL inhibition assay and the HSA binding assay have been performed on batch P #080408nr2 (produced in *P. pastoris*) and compared to the potencies of a batch RANKL008a purified from an *E. coli* expression (B11#140208 nr1). In the Table 4a the relative potencies of both materials (multiple analyses on different days) was found to be comparable. The HSA binding data represented in Table 4b are also not significantly different between two samples.

TABLE 4

Relative potencies of RANKL008a (*E. coli* batch B11#140208) compared to RANKL008a (batch P#080408 nr2) expressed in *P. pastoris* in the RANKL inhibition ELISA and HSA binding ELISA. With LL the lower limit and UL the upper limit of the confidence interval at 95%.

Table 4a

| | | RANKL Inhibition | | | |
|---|---|---|---|---|---|
| Assay Date | Sample ID | Relative Potency | LL | UL | Rel % CI |
| 1 | P#080408 nr2 | 0.810 | 0.769 | 0.853 | 10.4 |
| 2 | P#080408 nr2 | 0.826 | 0.762 | 0.894 | 16.0 |
| 3 | P#080408 nr2 | 0.884 | 0.813 | 0.962 | 16.9 |
| 4 | B11#140208 nr1 | 0.899 | 0.831 | 0.972 | 15.7 |

TABLE 4-continued

Relative potencies of RANKL008a (*E. coli* batch B11#140208) compared to RANKL008a (batch P#080408 nr2) expressed in *P. pastoris* in the RANKL inhibition ELISA and HSA binding ELISA. With LL the lower limit and UL the upper limit of the confidence interval at 95%.

| 5 | B11#140208 nr1 | 0.827 | 0.789 | 0.867 | 9.4 |
|---|---|---|---|---|---|
| 6 | B11#140208 nr1 | 0.791 | 0.729 | 0.858 | 16.3 |
| 7 | B11#140208 nr1 | 0.795 | 0.740 | 0.853 | 14.2 |
| 8 | B11#140208 nr1 | 0.728 | 0.675 | 0.875 | 15.1 |

Table 4b

| | | HSA Binding | | | |
|---|---|---|---|---|---|
| Assay Date | Sample ID | Relative Potency | LL | UL | Rel % CI |
| 1 | P#080408 nr2 | 0.809 | 0.773 | 0.847 | 9.1 |
| 2 | P#080408 nr2 | 0.786 | 0.743 | 0.832 | 11.3 |
| 3 | P#080408 nr2 | 0.853 | 0.816 | 0.891 | 8.8 |
| 4 | B11#140208 nr1 | 1.003 | 0.940 | 1.070 | 13.0 |
| 5 | B11#140208 nr1 | 0.937 | 0.883 | 0.995 | 12.0 |
| 6 | B11#140208 nr1 | 0.891 | 0.820 | 0.968 | 16.6 |
| 7 | B11#140208 nr1 | 0.969 | 0.909 | 1.032 | 12.6 |
| 8 | B11#140208 nr1 | 0.907 | 0.845 | 0.973 | 14.2 |

Example 3

Analysis by RP-HPLC Surprisingly Revealed the Presence of a Product Related Variant in Material Produced in *P. pastoris*

As outlined above, material produced in *P. pastoris* was characterized by equal functionality and as even higher homogeneity as compared to *E. coli* produced material.

Figure 4:
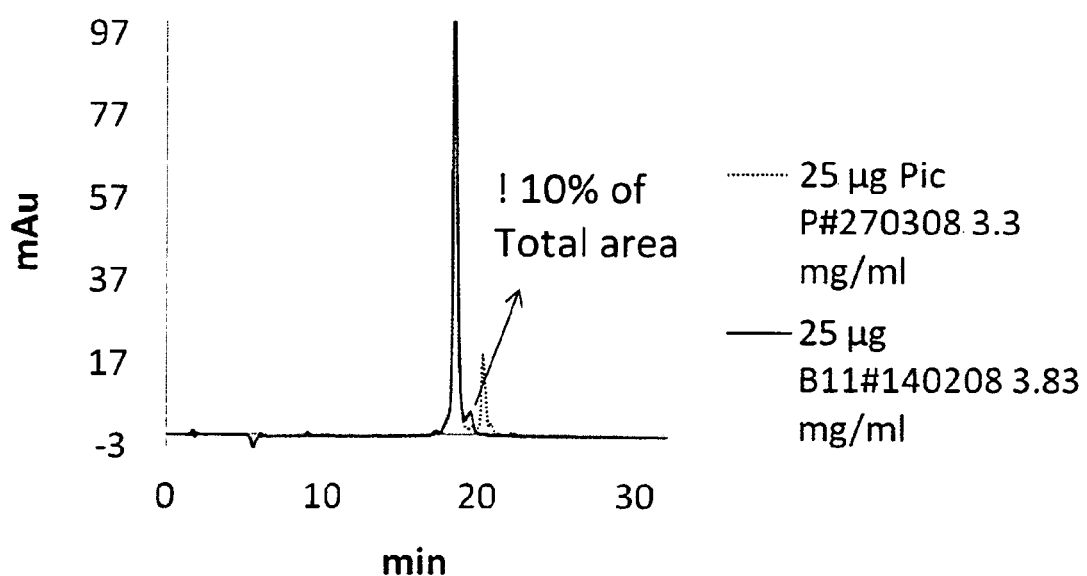
FIG. 4: RP-HPLC analysis of RANKL008a derived from *E. coli* (solid line) compared to material derived from *P. pastoris* (dotted line). X axis: retention time in minutes, Y-axis: OD monitored at 280 nm.

It was therefore highly surprising to find a product related variant in *P. pastoris* produced material upon analysis by RP-HPLC (FIG. 4). RP-HPLC was performed under following conditions:
Column: 300SB_C3 4.6*150 mm column Agilent ref 883995-909 run at 75° C.
Buffer A: water+0.1% TFA
Buffer B: 49.95% acetonitrile+49.95% isopropanol+0.1% TFA
Gradient see table below
Gradient table used in the RP HPLC method.

| Time (min) | Mobile phase B (%) |
|---|---|
| 0 | 10 |
| 2.5 | 10 |
| 3 | 27.5 |
| 30 | 36.5 |
| 30.5 | 95 |
| 33 | 95 |
| 33.1 | 10 |
| 36 | 10 |

The run can be monitored e.g. by UV detection at 214 and/or 280 nm, as indicated. In the chromatogram a pronounced and significant post peak appeared at about 20.5 minutes retention time in *P. pastoris* produced material ("Pic P #2703083.3"). In comparison, no such peak was observed in *E. coli* produced material ("B11#1402083.83"). The material of the post peak is also referred to as "product related variant", abbreviated as "PRV". Sometimes the product related variant of RANKL008a is also referred to as "PRV-RANKL008a".

It should be noted that between the different analyses performed there may be a slight difference in the absolute retention time of the main peak. However the distance between main and post peak is always constant and thus serves as the fingerprint. These differences are due to small differences in the buffer preparation.

To further characterize the nature of this product related variant, material was analyzed by Liquid Chromatography coupled to Electrospray Mass Spectrometry (LC-MS).

The material analyzed in FIG. 4 was subjected to an LC-MS analysis on a Waters Q-Tof Ultima Electro-spray Mass Spectrometer coupled directly to an Bioseparations Module (HPLC, Waters) on which a RP-HPLC analysis was performed. Total mass spectra were deconvoluted using the MaxEnt software (Waters) and demonstrate that the main peak in the RP-HPLC corresponds to a mass of 40943.01 (10 ppm accuracy), while the post-peak which takes up about 10% of the signal has a mass which is approximately 2 Da higher. The theoretical mass of RANKL008a is 40943.42 Da.

Thus, the main peak shown in FIG. 4 has the expected mass for RANKL008a. The post peak (post peak of 10% in chromatogram) corresponds to a mass of 40945.52 which corresponds to a mass of +2.1 versus the theoretical mass confirming that the mass difference between the main and post peak is 2 Da.

The total mass measurement on the ESI-MS reveals a +2 Da mass difference for the post peak. The exact nature of this post-peak was unknown at this stage, different hypotheses can be formulated:

One of the canonical disulfide bonds in one of the sub-units of the RANKL008a has not been formed, therefore the observed mass is +2 Da (two extra hydrogens).

Some amino acid substitutions can lead to a 2 Da mass difference for example a Threonine to Cystein, Aspartic Acid to Leucine substitution could lead to a mass difference of 2. However the DNA sequence of the RANKL008a gene was verified and was found to be correct. Alternatively, two sites of de-amidation (each leading to a +1 Da mass difference) could have occurred.

Further analysis of the post peak was undertaken in order to elucidate its nature.

Example 4

The Product Related Variant (Post Peak) Contains Free Thiol

Because the total mass determination described above cannot unambiguously describe the nature of the +2 Da mass difference the hypothesis of the non formed canonical disulfide bridge was explored by measuring directly the amount of free thiol in the protein sample. In RANKL008a no free thiol groups are present and the two cysteine residues present in each Nanobody sub-unit are normally linked into a disulfide bond.

Quantification of free thiol was performed using the Thiol and sulfide quantitation kit from Molecular Probes (Molecular Probes T-6060 Thiol and sulfide quantitation kit). All reagents were prepared and handled as described in the "Thiol and sulfide quantification kit" manual. The standard-curve is prepared between 0.2 and 1.4 µM; the samples are diluted to fall into the linear portion of the standard-curve, preferably at two to three positions within the linear part of the curve.

In this assay a direct comparison on RANKL008a expressed in *E. coli* was made to the RANKL008a expressed in *Pichia pastoris*.

Samples were denatured to allow full access to the free thiol groups in the protein using 6M guanidinium hydro-chloride (GuHCl) added as the solid salt. The final concentrations were: RANKL008a from *E. coli:* 53.85 µM; RANKL008a from *P. pastoris:* 46.40 µM.

The results of thiol quantification are shown in the following table:

TABLE 5

Results for the thiol quantification in samples of RANKL008a expressed in *E. coli* or in *Pichia pastoris*.

|  | RANKL008a µM | OD405 nm | Thiol µM | Free thiol per molecule |
|---|---|---|---|---|
| *Pichia* | | | | |
| Dilution 1 | 2.472 | 0.369 | 0.974 | 0.394 |
| Dilution 2 | 1.673 | 0.305 | 0.705 | 0.421 |
| Dilution 3 | 0.799 | 0.209 | 0.301 | 0.376 |
| | | | | Average: 0.397 |
| *E. Coli* | | | | |
| Dilution 1 | 2.872 | 0.184 | 0.195 | 0.068 |
| Dilution 2 | 1.943 | 0.164 | 0.111 | 0.057 |
| Dilution 3 | 0.929 | 0.158 | 0.086 | 0.092 |
| | | | | Average: 0.073 |

Using Molecular Probes' "Thiol and sulfide quantitation kit", the average ratio of free thiols per molecule of RANKL008a produced in *P. pastoris* was determined to be 0.397, whereas for RANKL008a produced in *E. coli* the measured value was 0.073.

The batch produced in *P. pastoris* used for the determination of free thiols was analyzed by RP-HPLC. The main peak amounted to 84.1% of total peak area, the post-peak accounted for 10.9% of total peak area and is assumed to consist of RANKL008a with 1 missing disulfide bridge. If this is indeed the case one would expect 0.218 free thiols/molecule of RANKL008a in this batch (2 thiols/molecule×10.9%).

The post-peak was followed by a smaller additional post-peak which accounted for 5% of the total peak area. Supposing that these represent the RANKL008a population missing a disulfide in each of its 13H5 sub domains, this would result in an average of 0.418 free thiols/molecule ((2 thiols/molecule×10.9%)+(4 thiols/molecule×5%)). The measured value of 0.397 corresponds very closely to this calculation and therefore it was concluded that the product related variant of respectively 10.5% and 5% represent a population of RANKL008a in which one or two disulfide bonds have not been formed.

Example 5

The Product Related Variant Binds to Activated Thiol Sepharose

If the preparation of RANKL008a produced in *P. pastoris* indeed contains a sub-population in which the disulfide bond has not been formed this population should bind to an Activated Thiol Sepharose 4B column. The binding to the column is performed in the absence or in the presence of increasing amounts of urea to appreciate to what extent the protein needs to unfold to allow access to the unpaired cysteine. The material is verified for the presence of the RANKL008a PRV by analyzing the sample by RP-HPLC after the binding to the affinity resin.

RANKL008a samples from expression in *P. pastoris* were diluted into D-PBS+1 mM EDTA (pH 7.0) in the presence of 6M urea. Samples were incubated with an excess amount of washed gel during 1 hour at room temperature. Samples were batch eluted and the flow through of the different samples was analyzed by RP-HPLC analysis.

Figure 5:
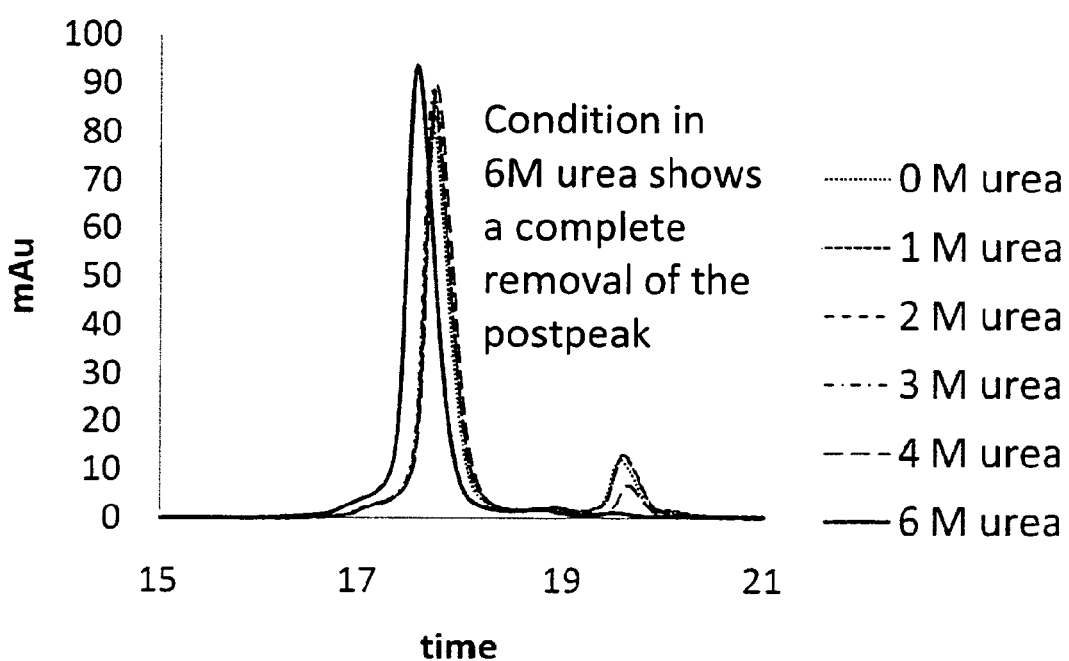
FIG. 5: RP-HPLC analysis of RANKL008a after incubation with a Thiol-Sepharose 4b resin in the presence of 0 M to 6 M urea. Chromatograms recorded at 280 nm. The condition in 6 M urea shows the complete removal of the postpeak.
Figure 6:
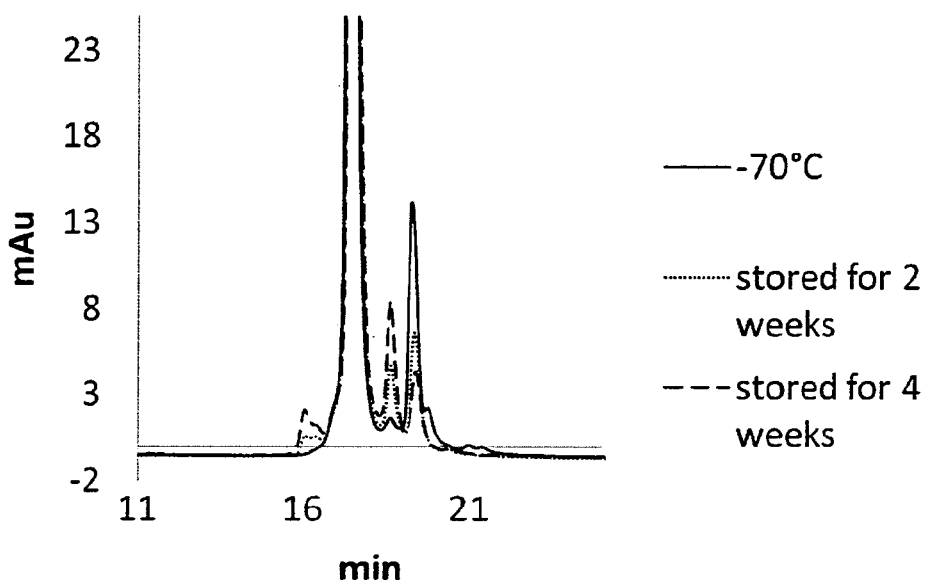
FIG. 6: RP-HPLC analysis of RANKL008a containing the product related variant stored for 2 (dotted trace) or 4 weeks (dashed trace) in comparison with the material stored at −70° C. (solid trace). Chromatograms are recorded at 280 nm.

From FIG. 5 it is clear that if RANKL008a is completely unfolded by 6M urea and is subjected to an incubation with the Thiol-Sepharose resin the product related variant—peak eluting at 19.5 minutes in RP-HPLC chromatogram—now has completely disappeared corroborating the finding that indeed the peak eluting after the main peak in the chromatogram represent the material that contains free thiols capable of binding to the thiol affinity resin. Because RANKL008a contains no other free cysteine in its sequence these data underpin the finding of the free thiols.

Example 6

Effect of Storage on the Stability of the PRV-RANKL008a

RANKL008a produced in *P. pastoris* was subjected to stability testing by placing the sterile solution in closed vials at 37° C. during 2 to 4 weeks. The RP-HPLC chromatogram was monitored in order to detect any changes occurring during the accelerated storage stress condition.

FIG. 6 illustrates that the product related variant with the missing disulfide bond (peak eluting at 19.5 min.) decreases upon storage at higher temperatures; the effect is already visible after two weeks and the peak continues to decrease after 4 weeks demonstrating that the free thiols spontaneously re-oxidize. This is corroborated by the observation that the total peak surface area that disappears at position 19.5 minutes is recovered in the surface areas of the peaks eluting at 17.5 minutes and the post peak that forms at 18.5 minutes, thereby underlining that the total mass did not change significantly during the storage (i.e. there was no loss of material e.g. due to precipitation).

During this storage a peak at 18.5 minutes elution was formed that increases with incubation time. This product is probably the pyro-glutamate formation at the N-terminus that is typically observed for all Nanobodies with an N-terminal glutamic acid and stored at higher temperatures.

Example 7

Analysis of the Nanobody 13H5-9GS-13H5

In order to confirm that the product related variant that appears in the RANKL008a protein expressed in *P. pastoris* corresponds to a variant in which the canonical disulfide bond has been disrupted a construct containing only the anti-RANKL Nanobody building block 13H5 and lacking the anti-albumin Nanobody sub-unit Alb8 was analyzed. Two 13H5 blocks were linked by a 9 GS linker sequence and the construct was named 13H5-9GS-13H5 (EVQLVESGG-GLVQPGGSLRLSCAASGFTF SSYPMGWFRQAPGKGREFVSSITGSGGSTYY-ADSVKGRFTISRDNAKNTLYLQMNSLRPED-TAVYYCA AYIRPDTYLSRDYR-KYDYWGQGTLVTVSSGGGGSGGGSEVQLVESG GGLVQPGGSLRLSCAASGFTFS SYPMGWFRQAPGKGREFVSSITGSGGSTYY-ADSVKGRFTISRDNAKNTLYLQMNSLRPEDTAVYY-CAA YIRPDTYLSRDYRKYDYWGQGTLVTVSS; SEQ ID NO: 7). The construct was expressed in *P. pastoris* and purified under identical conditions as were applied for the RANKL008a.

The 13H5-9GS-13H5 was analysed by RP-HPLC and LC-MS in the same way as RANKL008a.

Analysis of 13H5-9GS-13H5 clearly demonstrates that this construct-lacking the anti-albumin Nanobody—shows an identical result as the RANKL008a upon analysis by RP-HPLC. The elution time for this construct was—as expected—earlier in the gradient and in this chromatogram not only one clear post-peak of about 25% was detected, but a second post-peak of about 6.3% could be identified, suggesting that in this preparation there was also a population of molecules lacking the disulfide bond in both Nanobody sub-units. Subsequent LC-MS analysis demonstrated that the first post-peak indeed had a mass +2 Da.

Two aliquots of 13h5-9GS-13h5 were buffer exchanged to 20 mM Tris-HCl pH 8.0 100 mM NaCl. After this buffer exchange $CuSO_4.5H_2O$ was added to one of the samples in a final concentration of 100 μM and left at room temperature for 2 hours. Subsequently the excess Cu2+ was removed by an additional buffer exchange step. The protein concentration was determined for both samples:

13h5-9GS-13h5 untreated: 1.50 mg/mL

13h5-9GS-13h5 Cu-treated: 1.40 mg/mL

RP-HPLC analysis on a C3-RP-HPLC column of 25 μg of each sample is shown in FIG. 12. Exposing the sample to 100 μM $CuSO_4.5H_2O$ induces the formation of the disulphide bridges in 13h5-9GS-13h5 as evidenced by the disappearance of the post-peaks in the RP-HPLC chromatogram.

Thermal Shift Assay

Untreated and $Cu^{2+}$-treated 13h5-9GS-13h5 material was applied in a Thermal Shift Assay in a final concentration of 0.2 mg/mL with Sypro Orange in D-PBS buffer in order to determine if differences in the thermal stability of the molecules can be observed.

FIG. 13 shows the unfolding curves and the respective melting temperatures:

13h5-9GS-13h5 untreated: Tm1=65.36° C.

Tm2=73.81° C.

13h5-9GS-13h5 $Cu^{2+}$-treated: Tm1=73.66° C.

These profiles show that in the correctly folded protein one single melting temperature is observed corresponding to the unfolding of the 13H5 subunit. In contrast, the untreated sample shows two transitions, one corresponding to that of the correctly folded 13H5 subunit while the other 13H5 subunit—lacking the disulfide bond—unfolds already at lower temperatures.

Example 8

Despite the Presence of the Structural Variant, Function of *P. pastoris* Produced Material was Surprisingly Unaffected It is known from production of e.g. conventional Fab antibody fragments in *P. pastoris*, that the formation of interchain disulfide bonds was the rate limiting factor to assembly and secretion of functional Fabs (e.g. Gasser et al. Biotechnol. Bioeng. 94: 353, 2006).

It should therefore be expected that the presence of significant amounts of product related variant in *P. pastoris* produced Nanobodies would equally compromise function.

The presence of 10-25% product related variant lacking one disulfide bond would be expected to result in a corresponding loss of function.

Surprisingly, however, the functional comparison of the material produced in E. coli and P. pastoris did not reveal any differences in terms of Nanobody function. More specifically, the functional data (Biacore and ELISA) described above were equal for the different materials.

Biacore

As outlined above, Biacore analysis of binding of RANKL008a to HSA or RANKL was comparable for E. coli and P. pastoris derived material, and is not affected by the presence of 10-15% product related variant. For example, as was established by RP-HPLC, the batch P #270308nr1 produced in P. pastoris, which was analyzed by Biacore, contains about 15% product related variant. Nevertheless, the data described above indicate uncompromised functionality as reflected by unchanged binding to HSA or RANKL chips by Biacore. This is remarkable in view of the fact that the Biacore assay had a sensitivity that could clearly resolve a 10% concentration difference (see above).

Thus it can be assumed that the 13H5 Nanobody building block of RANKL008a in which the canonical disulfide bridge is not formed, surprisingly is fully functional (see tables 2 and 3). Similar observations were made when other batches of material were tested in independent experiment (data not shown).

ELISA

For RANKL008a both the RANKL inhibition assay and the HSA binding assay have been performed on a P. pastoris produced batch containing about 15% of the variant (P #080408nr2) and E. coli derived material which contains only the intact RANKL008a. There were no differences in this functional assay (see table 4a and 4b).

Example 9

Evaluation of Different Host Strains

The RANKL008a gene was transformed by electroporation into P. pastoris strains X-33, KM71H and SMD 1168H (all strains obtained from Invitrogen) by standard techniques. Expression for the KM71H and SMS 1168H strains was performed in 1 mL cultures in BMCM medium and induced by the addition of methanol, for each strain two different clones were analyzed. Samples from these shake-flask expressions were subjected to RP-HPLC analysis. For the X-33 RANKL008a several clones were tested repeatedly e.g. clone 5 and clone 17 and no difference in the proportion of the variant was observed between the different clones.

In order to avoid having to purify the material from the clarified culture supernatant by the standard three step purification process a methodology was used to capture the RANKL008a from the culture supernatant by a simple Protein A clean up: briefly, culture supernatant is mixed in batch mode with a quantity of a Protein A-resin, incubated and batch eluted. The purity of the material is such that a direct application (25 µg) to the RP-HPLC column is possible. The method is semi-quantitative and gives an indication on the expression yields and integrity for the different samples analyzed.

Table 6 summarizes the RP-HPLC peak area surface integration of the analysis of different culture supernatants from the expressions performed in the KM71H and SMS 1168H strains in comparison with a purified reference material obtained from expression in the X-33 strain.

TABLE 6

Summary of determination of % of PRV-RANKL008a (post peak) as determined by RP-HPLC in the supernatant of expressions of RANKL008a in different Pichia strains.

| Strain used for expression | Reference | % of peak surface area of the RP-HPLC attributed to variant (post peak) |
|---|---|---|
| X-33 | P#270308* | 14.7 |
| SMS 1168H | R8SM180408nr1 | 10.9 |
| SMS 1168H | R8SM180408nr2 | 6.3 |
| KM71H | R8KM180408nr1 | 12.7 |
| KM71H | R8KM180408nr2 | 12.8 |

*purified material; all other samples were analyzed after a ProtA clean up step as described above.

The data from Table 6 and the analysis of different clones of the X-33 produced RANKL008a (data not shown) reveals that the proportion of PRV-RANKL008a is not significantly different if expressed in the different strains or among different clones of one strain.

Example 10

Effect of Fermentation Conditions on PRV-RANKL008a

Several conditions for batch and fed batch fermentations were tested for the expression of RANKL008a, typically glycerol fed batches are performed and induction is initiated by the addition of methanol. All optimizations were performed with the X33 RANKL008a strain clone 5. The standard protocol was the Invitrogen protocol, expression at 30° C. in basal salt medium with a methanol feed rate of 10 ml/L*h.

The composition of the basal salt medium suitable e.g. for *Pichia pastoris* was as follows:

TABLE 7

Fermentation Basal Medium.

| Raw material | Concentration |
|---|---|
| Phosphoric acid, 85% | 26.7 mL/L |
| Calcium sulphate | 0.96 g/L |
| Potassium Sulphate | 18.2 g/L |
| Magnesium Sulphate•$7H_2O$ | 14.9 g/L |
| Potassium hydroxide | 4.13 g/L |
| Glycerol | 40 g/L |
| RO water | Adjust to 995 mL |
| PTM Trace salts (Table 8) (added after autoclaving) | 4.35 mL (230 x stock solution)/L |

TABLE 8

PTM Trace salts (230x stock solution; filter sterilised, 0.22 μm).

| Raw material | Concentration |
|---|---|
| RO water | ~700 mL |
| Cupric acid•5H2O | 6 g/L |
| Sodium Iodide | 0.08 g/L |
| Manganese sulphate•H2O | 3 g/L |
| Sodium Molybdate•2H2O | 0.2 g/L |
| Boric Acid | 0.02 g/L |

TABLE 8-continued

PTM Trace salts (230x stock solution; filter sterilised, 0.22 μm).

| Raw material | Concentration |
|---|---|
| Cobalt Chloride | 0.5 g/L |
| Zinc Chloride | 20 g/L |
| Ferrous sulphate•7H2O | 65 g/L |
| Biotine | 0.2 g/L |
| Sulfuric acid | 5 mL/L |
| RO water | Adjust to 1 L |

In some experiments, a rich medium was used to culture *P. pastoris*:

TABLE 9

Rich medium (components added before autoclaving).

| Medium components | Concentration |
|---|---|
| Yeast Extract | 20 g/L |
| Potassium dihydrogen phosphate | 13.5 g/L |
| Ammonium sulphate | 1.0 g/L |
| Magnesium Sulphate•7H2O | 15 g/L |
| Calcium dichloride•2H2O | 0.8 g/L |
| Glycerol | 60.0 g/L |
| RO water | Adjust to 990 mL |

After autoclaving the following components are added to the rich medium (Post Sterilization Additions):

TABLE 10

Post Sterilization Additions after autoclaving.

| | |
|---|---|
| Trace salts (Table 11) | 10 mL/L (100x stock solution) |
| Biotine | 2 mL/L from stock 0.2 g/L |

Trace salt stock solution for the rich medium has the following composition:

TABLE 11

Trace salts (100x stock solution; filter sterilised, 0.22 μm).

| Raw material | Conc. Required (per L) |
|---|---|
| RO water | ~700 mL |
| H2SO4 (conc.) | 10.0 mL |
| FeSO4•7H2O | 30.0 g |
| ZnSO4•7H2O | 4.25 g |
| CuSO4•5H2O | 1.90 g |
| Na2MoO4•2H2O | 2.00 g |
| H3BO3 | 0.50 g |
| Citric Acid (anhydrous) | 0.27 g |
| RO water | To 1 litre |

The following table summarizes the conditions tested for the optimization of the fed-batch fermentations of RANKL008a:

TABLE 12

Summary of fermentation strategies tested for RANKL008a expression in *Pichia pastoris* strain X33 clone 5.

| Medium | Modification to standard protocol | Estimated Titer (%)* | Degradation** | % of PRV-RANKL008a by RP-HPLC*** |
|---|---|---|---|---|
| Basal Salt Medium | — | 100 | +++ | 15 |
| Basal Salt Medium | Low methanol feed at 5 ml/L * h | 140 | +++ | 1 |
| Basal Salt Medium | Low conductivity (25 mS:cm versus 40 mS/cm) | <100 | +++ | 1 |
| Basal Salt Medium | Lower temperature during induction 25° C. versus 30° C. | <100 | +++ | 1-4 |
| Basal Salt medium | +yeast extract and peptone | 200 | (+) | 3-8 |
| Rich Medium | | 400 | (+) | 18 |

*% of control grown under standard conditions (first line in table above), determined in cell free supernatant by SDS-PAGE analysis and staining (coomassie brilliant blue or krypton stain) and visual comparison to a reference lane loaded with a fixed amount of material, for some conditions additional densitometric analysis in comparison with a reference curve obtained with purified material. Therefore these numbers should be regarded semi-quantitative

**determined from the coomassie stained SDS-PAGE analysis and judged as +++ pronounced degradation and (+) strongly reduced degradation into bivalent and monovalent degradation fragments

***RP-HPLC analysis of ProtA cleaned up culture supernatant. The % PRV-RANKL008a is expressed as the % of the total surface peak area for that run.

From the table the following is concluded:

There is a correlation between the observed titer and the % of PRV-RANKL008a during expression, i.e. the higher the titer the higher the % PRV-RANKL008a in the material.

Conditions of lower temperature, lower methanol feed and/or reduced conductivity result in lower growth rate and titer, but a population of RANKL008a protein that is devoid of the variant. Without being bound to theory, this may suggest that metabolic stress on the *P. pastoris* during the expression is the driver for the formation of the variant that is missing the disulfide bond.

Figure 7:
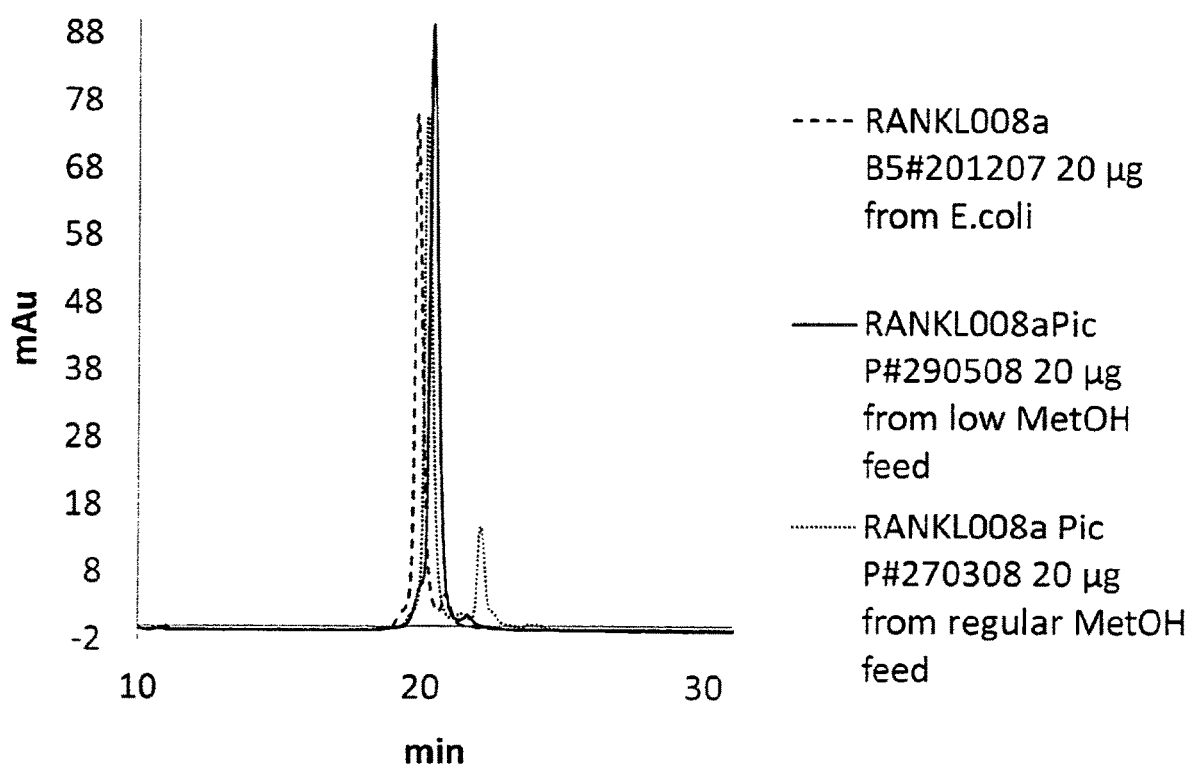
FIG. 7: RP-HPLC analysis of different batches of purified RANKL008a prepared from fermentations in *E. coli* (dashed trace), expression in *P. pastoris* shake flask experiment with standard methanol feeds (dotted trace) in comparison with fed batch fermentation expression in *P. pastoris* using a low methanol feed strategy (4 mL/h·L, solid trace).

FIG. 7 demonstrates that indeed material purified from a fed batch fermentation with low methanol feed strategy or material obtained from *E. coli* expression show the absence of the product related variant (in this chromatogram eluting at 22.5 minutes).

SDS-PAGE analysis (data not shown) of clarified culture supernatant (20 µL/lane) of RANKL008a expressed in conditions of low methanol feed (4 mL/h·L), low conductivity (20 mS/cm) and at 25° C. in basal salt medium was performed. For each condition different time points after induction (0, 9, 31 and 43 h) were analyzed. A reference of 300 ng was loaded for comparison. The major band at about the 37 kDa marker corresponds with intact RANKL008a. The pronounced bands at 22 and 14 kDa corresponded to the degradation fragments of RANKL008a, bivalent fragment and monovalent fragment respectively. It was observed that the condition with the low methanol feed has a higher expression than the two other conditions tested (conductivity and temperature). Under all three conditions degradation was pronounced.

Addition of yeast extract and peptone during the fermentation resulted in significantly less degradation of the intact material and a somewhat lower formation of the percentage of the variant. Without being bound to theory, this can probably be attributed to the fact that the addition of extra substrate will divert the protease activity from the RANKL008a to the bulk substrate present in the yeast extract and peptone. The effect of the addition of yeast extract and peptone on the degradation patterns is such that the degradation is virtually absent. The down stream process of this material—that contains much less degradation fragments—is much more straightforward and the recoveries of intact material are higher and therefore this is a preferred strategy.

Example 11

Over-Expressing Protein Disulfide Isomerase in *P. pastoris*

The enzyme Protein Disulfide Isomerase (PDI), a 55 kDa protein, has been shown to be a catalyst in protein folding, disulfide bond formation and isomerization in the endoplasmic reticulum (ER) of eukaryotic cells (Freedman et al. Trends Biochem. Sci. 19: 331, 1994; Wilkinson et al. 2005, J. Biol. Chem. 280: 11483). PDI is involved in the structure formation of immunoglobulins in vivo.

(Gonzalez et al. Biotechnol. Prog. 17: 217, 2001; Nilsson et al. Immunol. Lett. 94: 83, 2004).

Co-expression of antibodies with PDI has been applied to increase secretion rates and/or levels of functional product (Humphreys et al. FEBS Lett., 380: 194, 1996; Hsu et al. Protein Expr. Purif. 7: 281, 1996; Shusta et al. Nat. Biotechnol. 16: 773, 1998; Borth et al. Biotechnol. Prog. 21: 106, 2005). During fermentation of a *Pichia pastoris* strain that expresses a Fab, for example, the formation of inter-chain disulfide bonds was seen as the rate limiting factor to assembly and secretion of functional Fabs. Co-expression of this Fab with PDI in *P. pastoris* increased the secreted Fab level by 1.9-fold (Gasser et al. Biotechnol. Bioeng. 94: 353, 2006). In these methods, co-expression with PDI was applied to obtain increased expression rates and/or levels of functional product.

In contrast to the above difficulties observed with conventional four-chain antibodies, Nanobodies can be expressed and secreted in *P. pastoris* at a sufficient rate and level as well as functionality (see above), concluding that co-expression with PDI might not be a requirement. In a fraction of the obtained Nanobodies, however, the presence of free thiol was observed, due to unpaired cysteine residues. The absence of these disulfide bridges will have an impact on the quality and the homogeneity of the final Nanobody product and as such is undesirable, in particular in view of the therapeutic use of these products.

Cloning of PDI Gene and Generation of *Pichia* Strains that Overexpress PDI1

The gene coding PDI1 was picked up by PCR from the genome of

*Saccharomyces cerevisiae* using the FW primer 5'-GaattcatgaagttttctgctggtgccG-3' (SEQ ID NO: 1) reverse primer 5'-ctcgagTTACAATTCATCGTGAATGG-CATCTTCTTCG-3' (SEQ ID NO: 2) and cloned into the pcr4-TOPO vector.

Via EcoRI/XhoI digestion the coding region of PDI was cloned into a pPic6 derivative (Invitrogen) under the control of the constitutive GAP promoter using standard cloning techniques and transformed into a *Pichia* strain expressing RANKL008a.

The following protein sequence was retrieved (SEQ ID NO: 3):

MKFSAGAVLSWSSLLLASSVFAQQEAVAPEDSAVVKLATDSFNEYIQSHD

LVLAEFFAPWCGHCKNMAPEYVKAAETLVEKNITLAQIDCTENQDLCMEH

NIPGFPSLKIFKNSDVNNSIDYEGPRTAEAIVQFMIKQSQPAVAVVADLP

AYLANETFVTPVIVQSGKIDADFNATFYSMANKHFNDYDFVSAENADDDF

KLSIYLPSAMDEPVVYNGKKADIADADVFEKWLQVEALPYFGEIDGSVFA

QYVESGLPLGYLFYNDEEELEEYKPLFTELAKKNRGLMNFVSIDARKFGR

HAGNLNMKEQFPLFAIHDMTEDLKYGLPQLSEEAFDELSDKIVLESKAIE

SLVKDFLKGDASPIVKSQEIFENQDSSVFQLVGKNHDEIVNDPKKDVLVL

YYAPWCGHCKRLAPTYQELADTYANATSDVLIAKLDHTENDVRGVVIEGY

PTIVLYPGGKKSESVVYQGSRSLDSLFDFIKENGHFDVDGKALYEEAQEK

AAEEADADAELADEEDAIHDEL

Transformation and expression studies of wild type *Pichia* X-33 and derivatives were performed by standard techniques and in accordance to the user manual of pPicZalphaA, B and C version D, 110801, 25-0148 from Invitrogen. Clones were confirmed to overexpress PDI1 by Western Blotting.

Analysis of RANKL008a Obtained from the PDI Overexpressing *Pichia* Strains Versus Control Strain From the previous experiments it was clear that the post peak correspond to the variant of RANKL008a that lacks one disulfide bridge. The percentage of this variant peak was determined when RANKL008a was expressed in the wild type X-33 *P. pastoris* strain or in a modified strain overexpressing PDI1. For each strain 5 different clones were tested. Integration of the post peak area on the RP-HPLC profile showed that there was a small but significant reduction of post peak when RANKL008a was expressed in the PDI1 overexpressing strain (18.96±0.98% versus 14.82±0.91%; the percentage refers to the % of total peak area). These experiments clearly demonstrate the effect of PDI1 on the formation of disulfide bridges in the RANKL008a molecule.

Example 12

Chromatographic Methods Tested for Removing the PRV-RANKL008a

It is undesirable to generate e.g. a drug substance that contains both a population of intact RANKL008a and a significant proportion of 'unstable' (upon storage) variant. Therefore, 'standard' chromatographic steps were analyzed for their ability to remove this particular variant.

In particular, a Hydrophobic Interaction Chromatography step or a cation-exchange SP Sepharose chromatography was investigated for their ability to resolve intact material and the variant. The most important wash—and elution peaks of these chromatographies were analyzed by RP-HPLC to visualize any separation.

It was found that the product related variant could not be separated from the main peak by hydrophobic interaction chromatography or cation-exchange SP Sepharose chromatography.

There is also the possibility of removing the variant by using a Thiol-Sepharose affinity resin as described above. Here it is demonstrated that indeed the variant lacking a disulfide bond and thus containing free thiols can be removed on this resin, if the protein is fully denatured, e.g. in the presence of 6 M urea.

Example 13

Refolding in the Presence of Denaturant and Redox-Buffers

In order to investigate if the unformed disulfide bond in the 13H5 subunit of the RANKL008a can be brought to be formed commonly applied "refolding buffers" were tested, involving the denaturation and refolding in the presence of a redox buffer and subsequent removal of the refolding buffer by dialysis. The data obtained from the Thiol-Sepharose binding experiments also illustrate that some degree of unfolding may be needed during this process.

TABLE 13 summarizes the most relevant experimental results

| Condition tested | Effect on PRV-RANKL008a as judged by RP-HPLC |
| --- | --- |
| 6M Guanidinium hydrochloride (GdnHCl) | Completely Removed |
| Redox buffer only (cystamine/cysteamine) | Partial removal |
| 2M GdnHCl + subsequent dilution in cystamine/cysteamine (1:5 mM:mM) | Completely Removed |
| 2M GdnHCl + subsequent dilution in GSH/GSSG (5:1 mM:mM) | Partial removal |
| 2M GdnHCl + subsequent dilution in cystamine/cysteamine buffer kinetics and optimal redox buffer conditions | Completely Removed |
| Refolding of larger batch material in condition of 2M GdnHCl + cystamine/cysteamine 5:1 (mM:mM) at room temperature, overnight + subsequent dialysis and analysis of refolded material | Completely Removed |
| Urea 3M + cysteamine/cystamine buffer 1:5 (mM:mM), overnight incubation at room temperature | Completely Removed |

The above summary data presented in the table can be briefly described as follows:

RP-HPLC analysis of a batch of RANKL008a (batch P #270308nr1) that contains about 15% of the PRV was mixed with 6M GdnHCl (in some instances throughout this application guanidine hydrochloride is also abbreviated as "GuHCl") and subjected to dialysis against D-PBS (Dulbecco's Phosphate Buffered Saline). Samples were taken after different time points between 0.5 h and 10 h of dialysis. The variant, which was present in the RANKL008a preparation at about 15%, was removed after denaturation and subsequent dialysis to D-PBS; however, a new unidentified shoulder became apparent on the main peak (data not shown).

The same batch of RANKL008a (batch P #270308nr1) was diluted in cystamine/cysteamine buffer to a final concentration of 1:5 mM:mM cystamine/cysteamine without any denaturant in the buffer (D-PBS). Samples were taken after between 20 minutes and overnight incubation at room temperature and injected directly on the RP-HPLC column. It can be concluded that the presence of the redox couple cystamine/cysteamine in the buffer partially converts the variant, after an additional overnight incubation some further reduction in the proportion of the variant was observed (data not shown).

Figure 8:
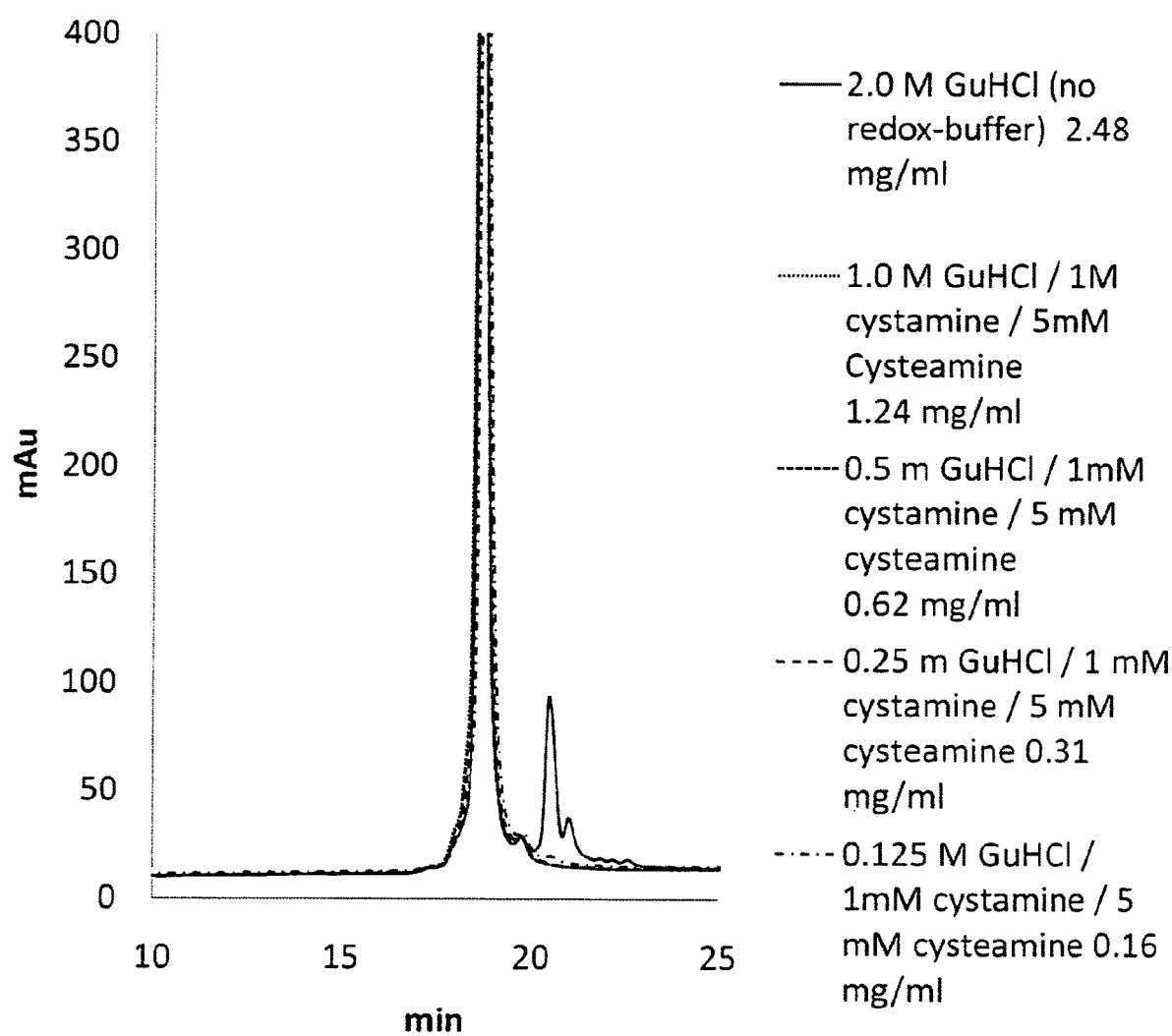
FIG. 8: RP-HPLC analysis of RANKL008a (batch P #270308nr1) mixed with 2.0 M GdnHCl ("GuHCl" in the figure) for 30 minutes at RT (solid trace) and subsequently diluted in redox buffer cystamine/cysteamine 1:5 (mM:mM) to a final concentration between 1.0 M and 0.125M GdnHCl as indicated and a subsequent overnight incubation at 4° C. Samples were directly applied to the column. Traces are recorded at 214 nm.

The same batch of RANKL008a (batch P #270308nr1) was mixed with 2M GdnHCl for 30 minutes at RT and subsequently diluted in redox buffer cystamine/cysteamine 1:5 (mM:mM) to a final concentration of 1.0 M; 0.5M, 0.25M and 0.125M GdnHCl and a subsequent overnight incubation at 4° C. Samples were directly applied to an RP-HPLC column. Traces are recorded at 214 nm and are shown in FIG. 8. FIG. 8 illustrates that if the RANKL008a is mixed upfront with 2M GdnHCl ("GuHCl" in the figure) the protein still contains the variant with the unpaired cysteines; however upon dilution of redox buffer and independent of the final concentration of GdnHCl in the buffer the variant is completely removed as evidenced from by RP-HPLC.

Figure 9:
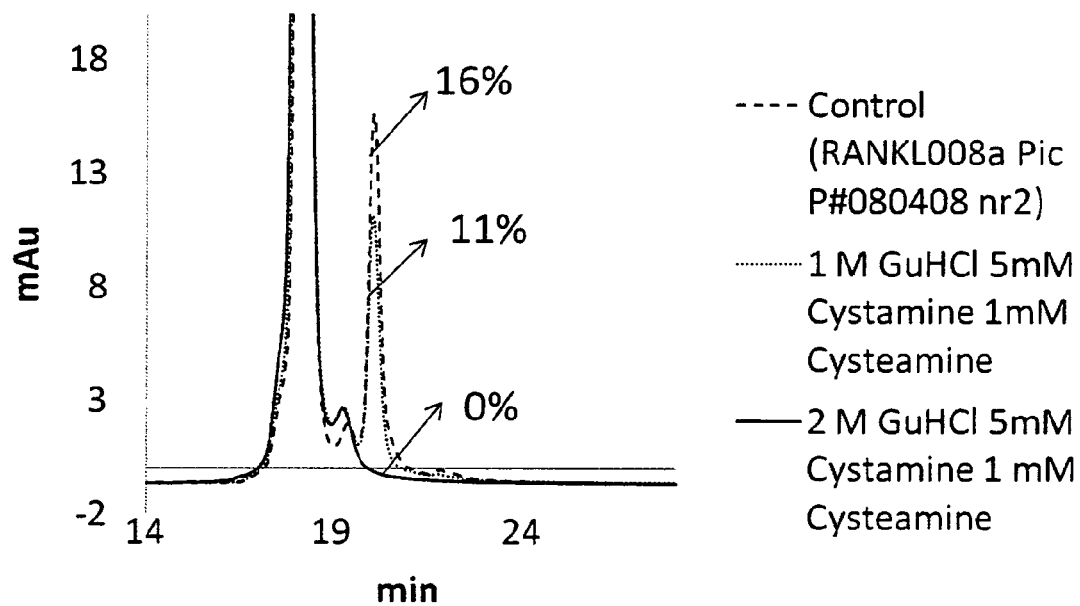
FIG. 9: RP-HPLC analysis of the RANKL008a (batch P #080408nr2) subjected to refolding overnight at room temperature in D-PBS. Untreated material is depicted in the dashed trace, the sample treated with 1M GdnHCl ("GuHCl" in the figure) and 5 mM cystamine and 1 mM cysteamine is represented in the dotted trace; while the solid trace represents the refolding in buffer containing 2M GdnHCl and 5 mM cystamine and 1 mM cysteamine. Samples were injected directly to the column. Chromatograms are recorded at 280 nm.
Figure 10:
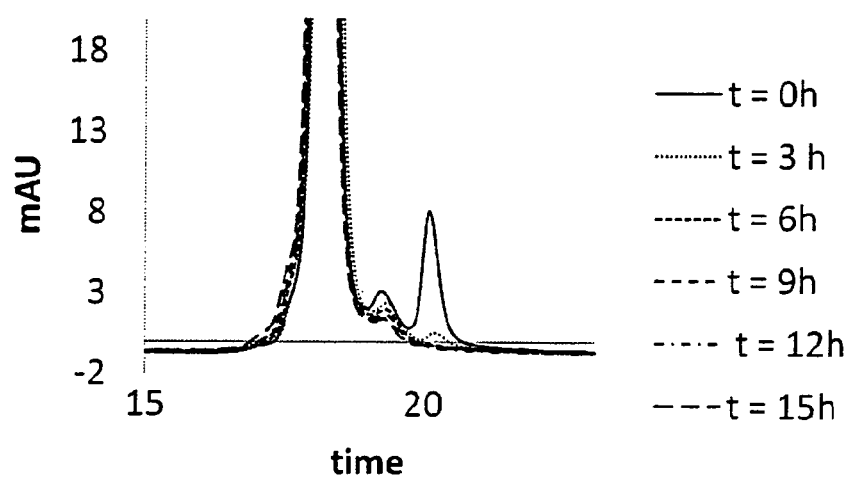
FIG. 10: RANKL008a (batch P #270308nr1) diluted in to D-PBS buffer containing 2M GdnHCl and 5 mM cystamine and 1 mM cysteamine, samples were taken at the time points indicated in the figure and analysed directly by RP-HPLC. Chromatograms are recorded at 280 nm.

Reductions of the variant could be observed at different concentrations of GdnHCl and different ratios of cystamine/cysteamine e.g. in the range from 5:1 to 1:5. Refolding is more efficient in the presence of 2M than 1M GdnHCl, and 5 mM cystamine/1 mM cysteamine as compared to the reverse ratio (FIG. 9). Refolding is nearly complete after 3 h and complete after 6 h at room temperature (FIG. 10).

The sample of FIG. 9 (solid line, 2M GdnHCl, 5:1 mM cystamine/cysteamine) was subjected to dialysis in order remove the redox buffer and to investigate if the material now contains only the completely oxidized form of the RANKL008a. Therefore the dialyzed material was analyzed by RP-HPLC and LC-MS. It was confirmed by RP-HPLC before and after dialysis and/or SEC treatment that the material remains fully oxidized also in the absence of the redox buffer. The samples were also analyzed by LC-MS to verify the correct mass after treatment.

The same batch of RANKL008a (batch P #270308nr1) was mixed with 2M GdnHCl for 30 minutes at RT and subsequently diluted in redox buffer GSH/GSSH (glutathione/reduced glutathione) 5:1 (mM:mM) to a final concentration of between 1.0 M and 0.125 M GdnHCl (in D-PBS) and subsequent overnight incubation at 4° C. Samples were directly applied to a RP-HPLC column. Mixing of RANKL008a upfront with 2M GdnHCl (assuming a partial unfolding of the protein) the protein still contains the variant with the unpaired cysteines; upon dilution of redox buffer with glutathione/reduced glutathione and independent of the final concentration of GdnHCl in the buffer the variant was not removed under these particular conditions (data not shown).

In a separate experiment it was found that a condition of 3M urea and a 1:5 mM cystamine/cysteamine buffer can lead to the refolding of the RANKL008a variant.

In conclusion, optimal refolding can be achieved in conditions that lead to the partial denaturation of the RANKL008a, e.g. 2M GdnHCl or 3M urea. Complete formation of the missing disulfide bond can be achieved and was confirmed by LC-MS analysis in the sample dialyzed against D-PBS.

Analysis by size exclusion chromatography revealed that during dialysis subsequent to the refolding of RANKL008a in the presence of GdnHCl and redox buffer a proportion of the RANKL008a is present as a dimeric aggregate of RANKL008a. This dimer is absent from the material before dialysis and clearly indicates that while the redox components are dialyzed out of the mixture a proportion of the RANKL008a forms an intermolecular cross link on the free cysteines that become temporarily accessible allowing to "escape" intra-molecular oxidation (confirmed by SDS-PAGE analysis (reducing and non reducing), data not shown).

Example 14

Effect of Temperature and Oxygenation on the Proportion of PRV-RANKL008a

Here it is shown that raising the temperature and/or oxygenation of the sample leads to formation of the missing disulfide bridge in one or both of the RANKL binding domains.

Purified RANKL008a was oxygenated in solution at elevated temperature. This was performed in a fermentation vessel where the temperature can be controlled to 50° C., the sample was purged with $O_2$ whilst gentle stirring (foaming occurred). Samples were taken at regular intervals and the percentage of PRV-RANKL008a visible in the RP-HPLC analysis as the post peak measured at about 2 min from the main peak was measured. It could be shown that this treatment results in a conversion of the variant into intact material. By holding the sample at 50° C. for about 3 h some decrease was observed, the addition of $O_2$ clearly sped up the decrease of the variant indicating that conditions of higher temperature are accompanied by a formation of the disulfide bond in the variant. After about 450 minutes at 50° C. and oxygenation the sample percentage of variant was decreased by 50%. An effect was observed for post-peak1 which elutes at +2 min from the main peak and corresponds to the RANKL008a variant in which a single disulfide bond is missing; moreover the post peak 2—which is assumed to represent the variant in which the disulfide bond is missing in each of the 13H5 sub-units and which elutes at +4 min from the main peak—was also sensitive to the treatment described above.

Example 15

Effect of pH, Temperature and Addition of Oxidizing Agents on the Removal of PRV-RANKL008a A series of experiments were performed in which the effects of pH, temperature (or combinations of both) and the addition of oxidizing agents, e.g. Cu2+ exemplified by CuSO4, was tested.

Initially these conditions were tested on a purified batch of RANKL008a that contained more than 10% of the variant and which was at a concentration of 7.8 mg/mL in PBS. In some of these conditions—especially the addition of CuSO4—the formation of a visible precipitate was observed in the mixtures. This was attributed to the fact that Cu2+ under these conditions forms insoluble Cu3(PO4)2. Therefore conditions were tested in which the sample was dialyzed to a solution of CuSO4 rather than by direct additions. Alternatively, different buffer systems can readily be applied to avoid the formation of the precipitate. For example, in the follow up experiments the samples were buffer exchanged into Tris-HCl—HCl buffer.

In the following table the different conditions that were tested are summarized. RANKL008a Batch P #080408nr2 at 7.8 mg/mL in D-PBS was used.

TABLE 14

Sample treatment scheme tested for the reduction of the PRV-RANKL008a in conditions of increased pH, temperature and addition of Cu2+.

| Conditions | Action | Incubations | | | Conc. mg/mL | Visual appearance |
| --- | --- | --- | --- | --- | --- | --- |
| pH 8.0 | Dilute in Tris-HCl—HCl pH 8.0 | ON at RT | 2 h 37° C. | 2 h 55° C. | 1 | Clear |
| pH 9.0 | Dilute in Tris-HCl—HCl pH 8.0 | ON at RT | 2 h 37° C. | 2 h 55° C. | 1 | The sample heated to 55° C. contains precipitate upon cooling to RT |

TABLE 14-continued

Sample treatment scheme tested for the reduction of the PRV-RANKL008a in conditions of increased pH, temperature and addition of Cu2+.

| Conditions | Action | Incubations | Conc. mg/mL | Visual appearance |
|---|---|---|---|---|
| CuSO4 1 mM | Dialyse to 1 mM CuSO4 for 2 h at 4° C. then dialyse overnight to PBS | 2 h 4° C. | 1 | Clear Protein concentration after dialysis is 0.94 mg/mL (no material loss) |
| CuSO4 0.5 mM + quenching by addition of EDTA | Dilute in CuSO4 1 mM + 1 mM EDTA + 20 mM citric acid pH 7.0* | ON 4° C. | 4 | |

The samples were subjected to RP-HPLC analysis, peak surface areas were determined. The results are expressed in mAU/peak for the main peak, the peak eluting at 0.2 minutes (corresponding to the pyro-glutamate variant) and the post peak at +2 minutes corresponding to the variant lacking the disulfide bond.

TABLE 15

Surface peak area for the individual peaks: Peak surface area (mAU) of the different peaks observed in the RP-HPLC chromatogram of RANKL008a samples incubated at different temperatures at pH 8.0, at pH 9 or in conditions in the presence of CuSO4 with or without quencher in comparison with untreated sample in the conditions as specified in the table above.

| | Untreated | RT | 37° C. | 55° C. |
|---|---|---|---|---|
| pH 8 | | | | |
| Main | 1268 | 1280 | 1299 | 1301 |
| Main + 0.2 min | 41 | 43 | 45 | 42 |
| Main + 2 min | 220 | 220 | 224 | 11 |
| Sum of all peaks | 1529 | 1543 | 1568 | 1354 |
| pH 9 | | | | |
| Main | 1268 | 1260 | 1280 | 1249 |
| Main + 0.2 min | 41 | 40 | 42 | 47 |
| Main + 2 min | 220 | 156 | 160 | 0 |
| Sum of all peaks | 1529 | 1456 | 1482 | 1296 |

| Cu2+ | Untreated | CuSO4 1 mM | CuSO4 1 mM + quench |
|---|---|---|---|
| Main | 1268 | 1530 | 1255 |
| Main + 0.2 min | 41 | 55 | 40 |
| Main + 2 min | 220 | 0 | 204 |
| Sum of all peaks | 1529 | 1585 | 1499 |

From the data summarized in Table 15 it is clear that:

Holding the sample at a temperature of 55° C. promotes the formation of the disulfide bond in the variant.

Holding the sample at a temperature of 55° C. and pH 9 leads to some loss in material as evidenced by the formation of a precipitate—the lower total surface area recovered in the RP-HPLC illustrates that some sample is lost during the heating (visual precipitate was observed).

The formation of the disulfide bond in the variant is faster at pH 9 than at pH 8 in comparable conditions.

Incubation at pH 9 seems to increase slightly the formation of the pyro-glutamate variant.

After exposure to 1 mM CuSO4 the variant cannot be detected after 2 hours incubation. Once the CuSO4 is removed by subsequent dialysis the disulfide bond remains intact. The total surface area of the sample before and after Cu2+ treatment is comparable. This means that all product related variant is converted quantitatively into main peak, i.e. intact material. Note that in these conditions the sample is at pH 7.

The oxidative effect of Cu2+ is completely quenched by EDTA.

Samples were verified by LC-MS and it was confirmed that in the sample before treatment the variant at +2 minutes corresponds to a mass +2 Da, while this mass +2 Da is not observed in the sample after overnight incubation at pH9 and after treatment with CuSO4.

At the end of the experiment the samples were stored for 1 week at 37° C. and re-analysed by RP-HPLC. Data—expressed as % of total surface area—are summarized in the following table.

TABLE 16

RP-HPLC analysis-% of total peak surface area-of RANKL008a samples incubated at higher pH and temperature or in the presence of CuSO4 and the subjected to an additional storage for 1 week at 37° C.

| Sample ID | Peak | % area | % area after 1 week @ 37° C. |
|---|---|---|---|
| pH 8, RT | Main peak | 81.8 | 85.9 |
| | +0.2 min | 2.7 | 4.6 |
| | +2 min | 14.1 | 9.5 |
| pH 8, 37° C. | Main peak | 81.5 | 85.9 |
| | +0.2 min | 2.8 | 4.7 |
| | +2 min | 14.1 | 9.4 |
| pH 8, 55° C. | Main peak | 94 | 95.4 |
| | +0.2 min | 3 | 4.6 |
| | +2 min | / | / |

TABLE 16-continued

RP-HPLC analysis-% of total peak surface area-of RANKL008a samples incubated at higher pH and temperature or in the presence of CuSO4 and the subjected to an additional storage for 1 week at 37° C.

| Sample ID | Peak | % area | % area after 1 week @ 37° C. |
|---|---|---|---|
| pH 9, RT | Main peak | 84.5 | 90.2 |
|  | +0.2 min | 2.7 | 4.9 |
|  | +2 min | 10.5 | 4.9 |
| pH 9, 37° C. | Main peak | 84.1 | 89.2 |
|  | +0.2 min | 2.8 | 5.2 |
|  | +2 min | 10.5 | 5.5 |
| pH 9, 55° C. | Main peak | 96.5 | 94.2 |
|  | +0.2 min | 3.5 | 5.8 |
|  | +2 min | / | / |
| Dialysis 1 mM CuSO4 | Main peak | 96.5 | 95.0 |
|  | +0.2 min | 3.5 | 5.0 |
|  | +2 min | / | / |
| 1 mM CuSO4, 1 mM EDTA, 20 mM citric acid pH 7.0 | Main peak | 83.7 | 86.5 |
|  | +0.2 min | 2.6 | 3.3 |
|  | +2 min | 13.6 | 10.3 |

Conclusions from this table are:

The % peak area attributed to the disulfide variant present in the sample after the initial overnight treatment (e.g. pH 8.0 37° C.) further reduces upon an additional week storage at 37° C.

Upon storage at higher pH's (pH 8 and 9) compared to the D-PBS for the CuSO4 treated samples the % the pyroglutamate variant at +0.2 min increases.

The material subjected to Cu2+ treatment and subsequent dialysis remains intact after 1 week 37° C. suggesting that the re-oxidized disulfide bond is stable upon storage.

In the sample that contains Cu2+ and the quencher EDTA the disulfide variant reduces slightly illustrating that the quenching is incomplete upon storage.

In conclusion, in this comparison the most efficient removal of the disulfide variant was obtained by treating the sample with Cu2+; the reaction is fast and the variant is quantitatively converted into intact material by the treatment; moreover if preferred it can be performed at neutral pH. The presence of denaturant is not required.

The conditions observed during the above experiment suggest that oxidation and formation of the disulfide bond occurs readily by incubation of the sample in the presence of Cu2+. In this follow up experiments different batches of material were included as listed in the Table 17. A batch of the 13H5-9GS-13H5 was included in these experiments. Samples were dialyzed into 20 mM Tris-HCl buffer (pH 8) and from a stock solution of CuSO4 final concentrations of 10 µM; 100 µM, 1 mM and 100 mM was added, samples were incubated for 2 h at room temperature and then dialyzed against D-PBS (overnight). Excess CuSO4 at 100 mM was added to detect any undesirable oxidation effects on the material.

TABLE 17

Samples exposed to Cu2+ in Tris-HCl HCl.

| Protein ID | Batch | Remark |
|---|---|---|
| 13H5-9GS-13H5 | B7#310708 | Bivalent Nanobody, produced in P. pastoris, ±24% postpeak lacking one disulfide bridge, ±6% postpeak lacking two disulfide bridges |
| RANKL008a | P#080408nr2 | produced in P. pastoris, ±15% postpeak lacking one disulfide bridge |
| RANKL008a | P#110708 | produced in P. pastoris, ±1% postpeak lacking one disulfide bridge |
| RANKL008a | B11#140208 | Produced in E. coli; no postpeak |

Samples were analyzed on RP-HPLC and the data plotted.

Figure 11:
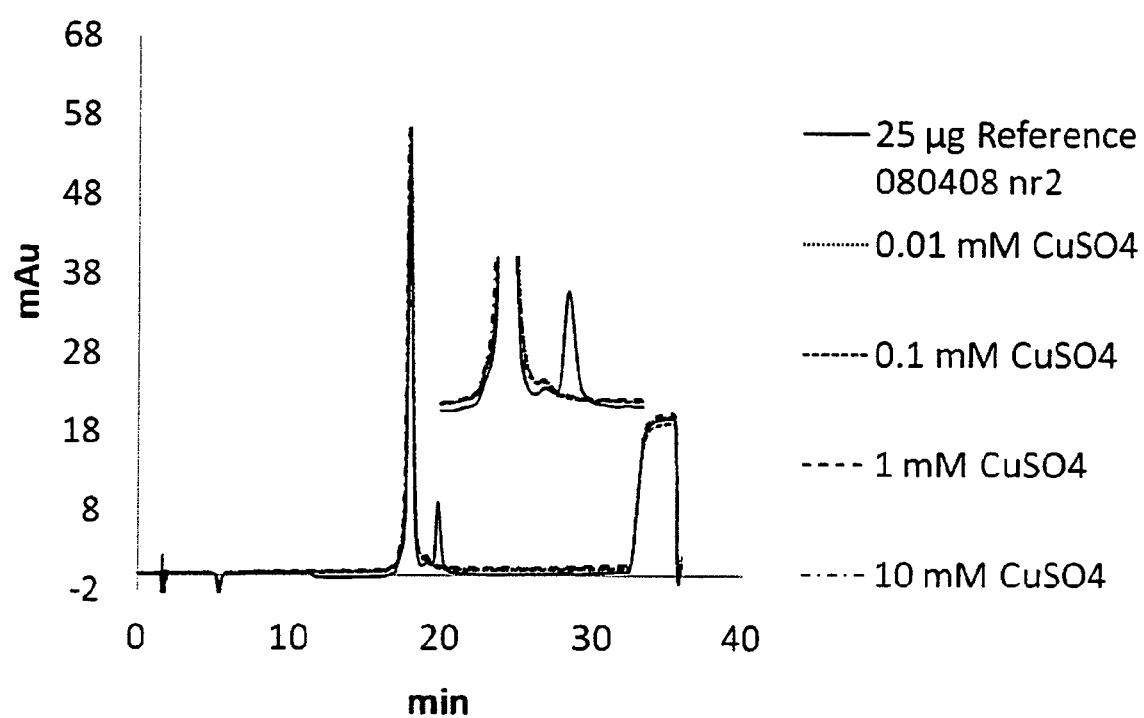
FIG. 11: RP-HPLC analysis of RANKL008a and chromatograms are recorded at 280 nm. The addition of different concentrations of CuSO4 leads to a complete disappearance of the postpeak.
Figure 12:
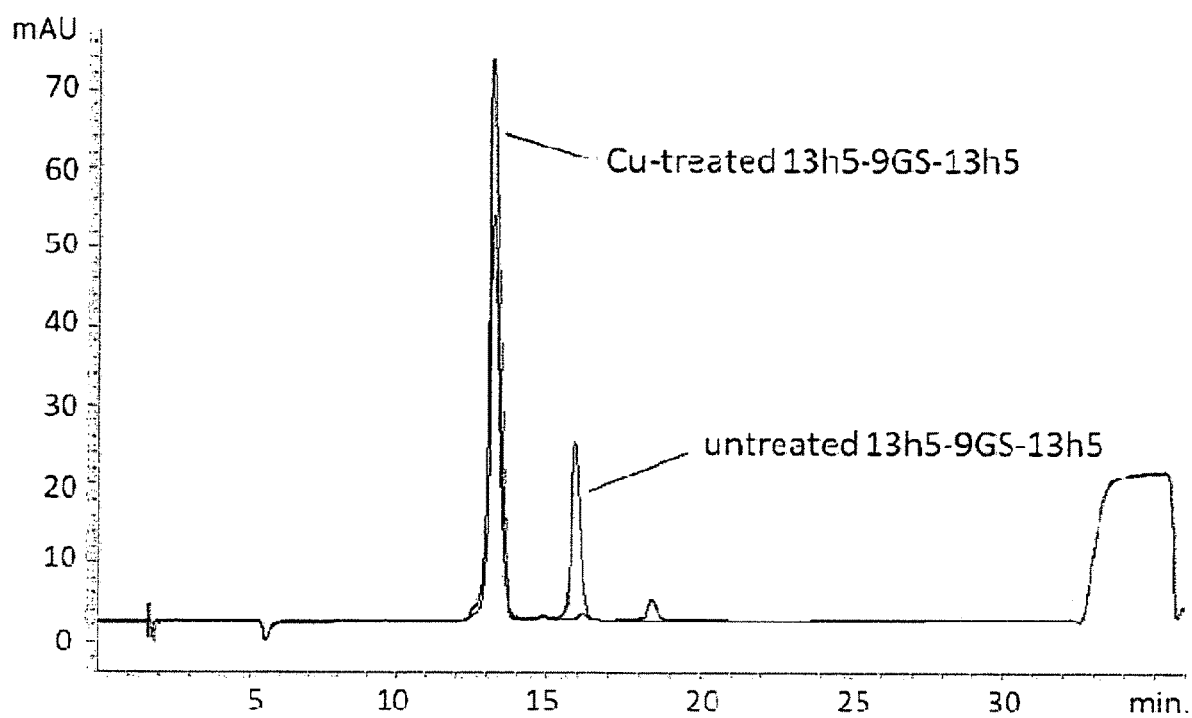
FIG. 12: RP-HPLC profiles of 13h5-9GS-13h5 untreated and Cu-treated.
Figure 13:
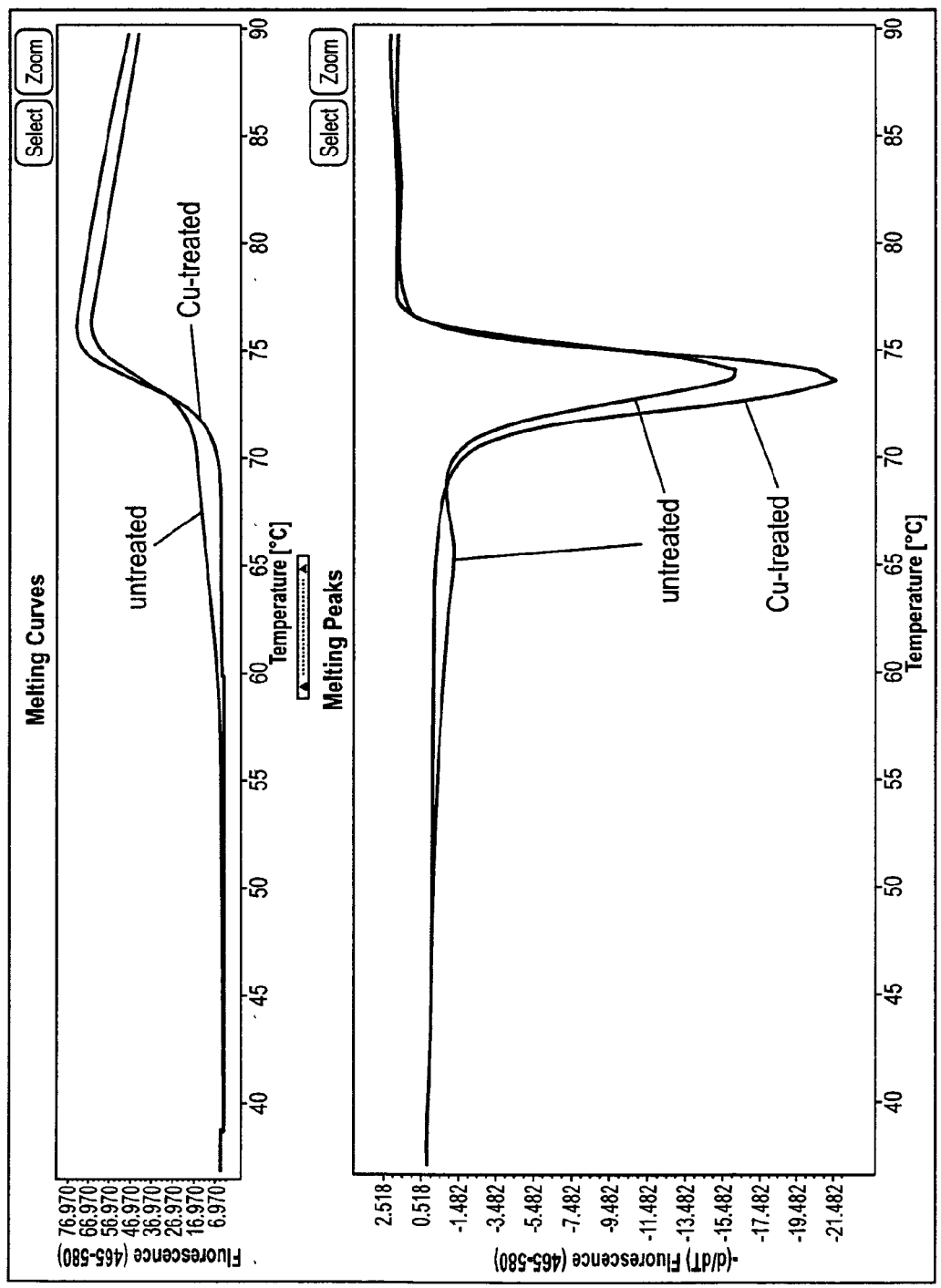
FIG. 13: TSA profiles for untreated and Cu-treated 13h5-9GS-13h5.

The data demonstrate that in the bivalent 13H5-9GS-13H5 Nanobody the variant missing respectively one or two disulfide bonds were nearly 100% absent after treatment with 1 mM CuSO4, while the process seemed to be occurring at lower CuSO4 concentrations for the P. pastoris expressed RANKL008a material that contains about 15% variant (see FIG. 11). In none of the chromatograms and the materials (expressed in E. coli or in P. pastoris or with different percentages of variant) the formation of significant (undesirable) pre-peaks was observed. If a sample of RANKL008a is subjected to strong oxidizing conditions (in the presence of the denaturant) such as H2O2 treatment the formation of methionine oxidation products was observed that typically elute before the main peak. In none of the chromatograms evidence was seen for the formation of significant pre-peaks indicating that the copper treatment does not seem to oxidize methionines in the protein, nor does the total mass analysis detect any +16 Da mass increase which would be consistent with a single oxidation on for example a methionine.

Example 16

Other Metals Tested and Other Oxidizing Agents

Fe2+, Fe3+ and Zn2+, added in the form of FeSO4 and ZnSO4 were tested and were shown to also induce the formation of the canonical disulfide bond in the variant (data not shown). Auto-oxidation of thiols by copper ions has been reported in the literature (Goldstein et al. Free Radical Biol Med 1986, 2, 3-11) while it has been demonstrated also that intra-molecular disulfide formation in synthetic peptides can be catalyzed by trace metals in the buffers (Cline et al. Analytical Biochemistry, 2004, 335, 168-170).

It is herewith suggested that other oxidizing agents (iodine, DMSO, H2O2, glutathione, and others) can accelerate the trace metal induced oxidation. Other metal-salts may also be efficient in the auto-oxidation of free thiols.

Example 17

Performing the Oxidation Step in Purified Product, Culture Broth and Clarified Culture Supernatant All the experiments described above were performed with purified RANKL008a. However if such a treatment is performed in the final stages of a production process one may anticipate having trace amounts of e.g. copper ions in the final product, which may upon storage cause further undesired oxidations of other amino acid residues. It was therefore investigated if such a treatment could be applied in materials upstream in the production process. Several experiments were performed in semi-purified samples (after one step purification on SP-Sepharose resulting in a purity of >95%) or on material that is present in the un-clarified culture broth and/or in clarified culture medium. The data confirm that also in less pure protein mixtures the variant can be removed by treating the samples with 1 mM CuSO4 at room temperature for at least 2h.

In one particular, preferable embodiment of the invention 1 mM CuSO4 is added for at least two hours at room temperature in the clarified culture supernatant (brought to pH 4.0) obtained after the fermentation.

Example 18

Analysis by RP-HPLC Revealed the Presence of a Similar Product Related Variant in Material Produced in *Saccharomyces cerevisiae* as Described in Example 3

RANKL008a was also produced in the yeast *Saccharomyces cerevisiae*. RANKL008a was expressed in *Saccharomyces cerevisiae* (INVsc1) under control of the episomal expression vector pYES (Invitrogen) The *Saccharomyces cerevisiae* produced RANKL008a protein was purified from clarified supernatant on a Protein A resin and analyzed by RP-HPLC (FIG. 14) and compared to RANKL008 expressed in *Pichia pastoris*.

Figure 14:
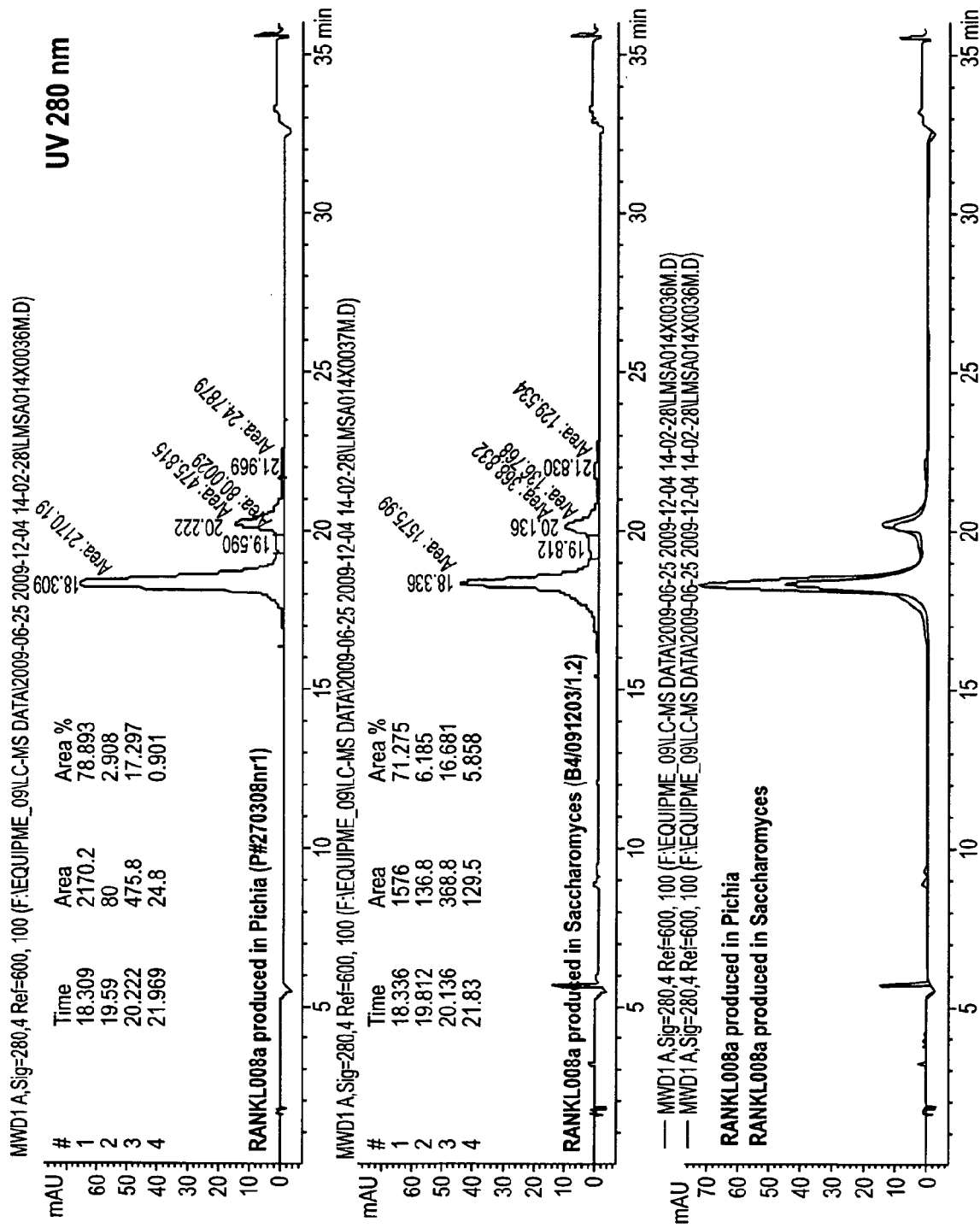
FIG. 14: UV 280 chromatograms of RANKL008a produced in *Pichia* (top panel) and *Saccharomyces* (middle panel) with the respective manual integration data and an overlay of both signals (bottom panel). Both *Saccharomyces* and *Pichia* produced RANKL008a contain the post-peak that represents the protein with a missing disulfide bridge as described in Example 3.

As determined from FIG. 14 the proportion of variant with the missing disulfide bond (post peak present at about +2 minutes from the main peak) was 16.7% for the material expressed in *S. cerevisiae* as compared to 17.3% when secreted by *Pichia pastoris*.

The material purified from supernatants of *S. cerevisiae* was analyzed in FIG. 14 and subjected to an LC-MS analysis on a Waters Q-Tof Ultima Electro-spray Mass Spectrometer coupled directly to an Bioseparations Module (HPLC, Waters) on which a RP-HPLC analysis was performed. Total mass spectra were deconvoluted using the MaxEnt software (Waters) and demonstrate that the post-peak had a mass which was approximately 2 Da higher than the main peak.

In the following Examples it is demonstrated that, upon expression of other Nanobodies in non-*E. coli* hosts, also a product related variant of these Nanobodies, lacking one or more disulfide bridges, was observed.

Example 19

Observations of a Similar Variant in Nanobody A-1 Expressed in *Pichia pastoris*

Another Nanobody construct, Nanobody A-1 was also expressed in *P. pastoris*. Nanobody A-1 consists of two identical single variable domains fused with a 3 alanine linker and has the following sequence (SEQ ID NO: 4):

```
DVQLVESGGGLVQPGGSLRLSCAASGRTFSYNPMGWFRQAPGKGRELVAA
ISRTGGSTYYPESVEGRFTISRDNAKRTVYLQMNSLRAEDTAVYYCAAAG
VRAEQGRVRTLPSEYTFWGQGTQVTVSSAAAEVQLVESGGGLVQPGGSLR
LSCAASGRTFSYNPMGWFRQAPGKGRELVAAISRTGGSTYYPESVEGRFT
ISRDNAKRTVYLQMNSLRAEDTAVYYCAAAGVRAEQGRVRTLPSEYTFWG
QGTQVTVSS
```

For Nanobody A-1 similar variants—lacking the disulfide bond—were identified both by RP-HPLC and associated LC-MS analysis of the different RP-HPLC peaks. Treatment of these Nanobodies with 1 mM CuSO4 for 2 h at room temperature removed the variant.

Example 20

Observations of a Similar Variant in Nanobody A-2 Expressed in *Pichia pastoris*

Nanobody A-2 was also produced in *P. pastoris*. Nanobody A-2 is a bispecific Nanobody that consists of two different single variable domains, having the following sequence (SEQ ID NO: 5):

```
EVQLVESGGGLVQPGGSLRLSCAASGSVFKINVMAWYRQAPGKGRELVAG
IISGGSTSYADSVKGRFTISRDNAKNTLYLQMNSLRPEDTAVYYCAFITT
ESDYDLGRRYWGQGTLVTVSSGGGGSGGGSEVQLVESGGGLVQPGNSLRL
SCAASGFTFSSFGMSWVRQAPGKGLEWVSSISGSGSDTLYADSVKGRFTI
SRDNAKTTLYLQMNSLRPEDTAVYYCTIGGSLSRSSQGTLVTVSS
```

For Nanobody A-2 similar variants—lacking the disulfide bond—were identified both by RP-HPLC and associated LC-MS analysis of the different RP-HPLC peaks. Treatment of these Nanobodies with 1 mM CuSO4 for 2 h at room temperature removed the variant.

Figure 15:
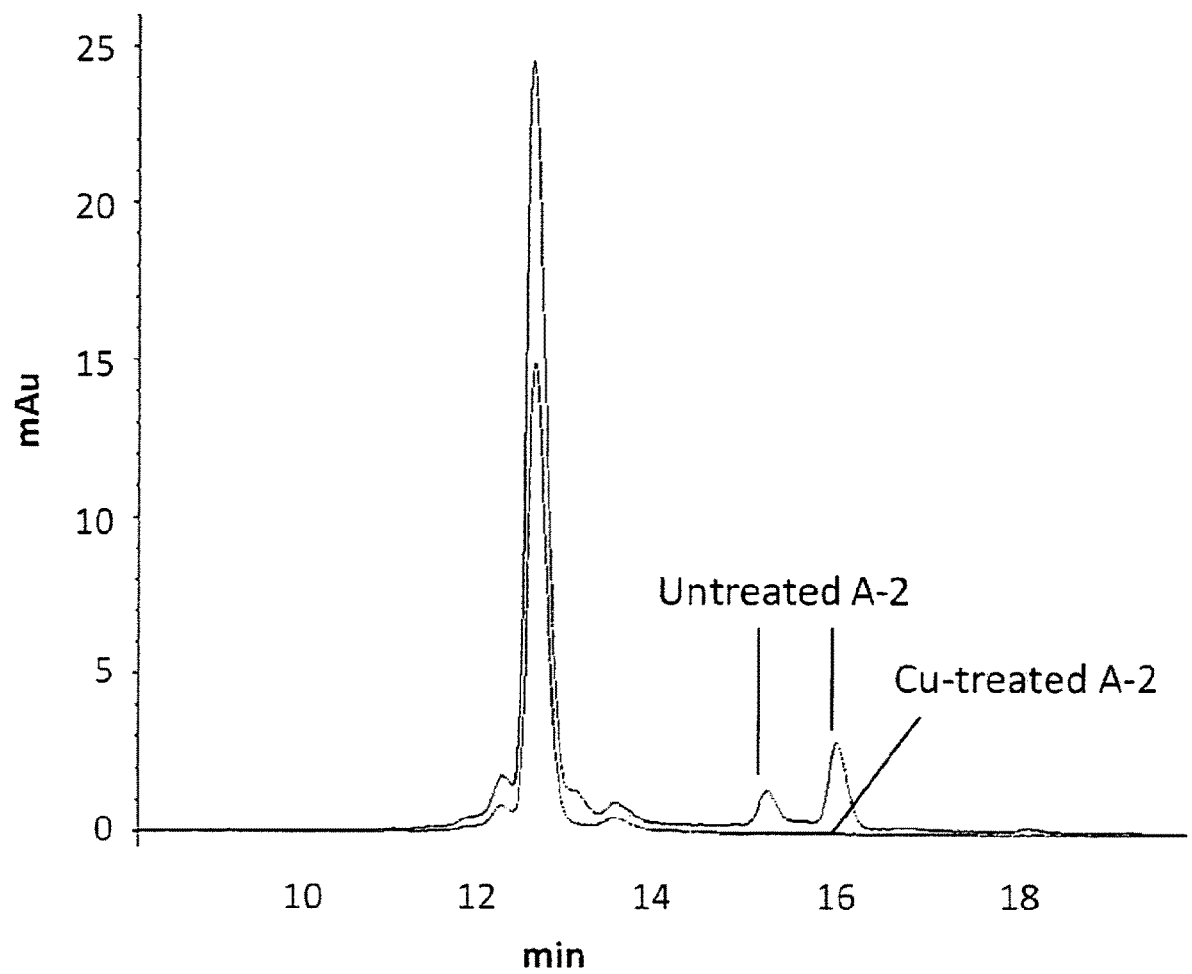
FIG. 15: RP-HPLC analysis of Nanobody A-2 before and after treatment with 1 mM CuSO$_4$ for 2 hours. The two postpeaks have disappeared completely in the Cu-treated sample. Note that because of the lower load for the Cu-treated sample, the peak height of the main peak and side-peaks is lower than for the untreated sample. Chromatograms were recorded at 280 nm.

For Nanobody A-2, two distinct postpeaks have been observed in the RP-HPLC chromatogram (FIG. 15). The postpeak at Rt+2.6 min relative to the main peak corresponds to a variant with a mass of +2 Da compared to the theoretical mass, thus representing the variant with a missing disulfide bridge. The postpeak at Rt+3.5 min relative to the main peak most likely corresponds to a variant missing two disulfide bridges, although this is not yet confirmed by LC-MS. The observation that this peak disappeared after treatment with CuSO4 however supports this hypothesis (FIG. 15).

Example 21

Observations of a Similar Variant in Nanobody A-3 Expressed in *Pichia pastoris*

Figure 16:
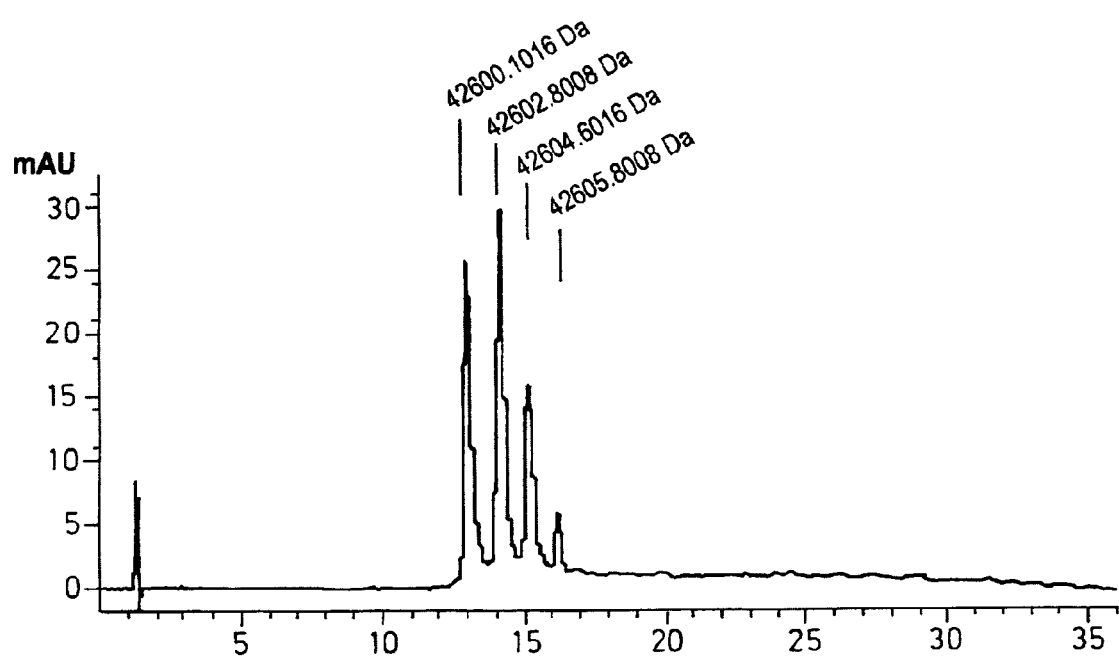
FIG. 16: RP-HPLC analysis of Nanobody A-3.
Figure 17:
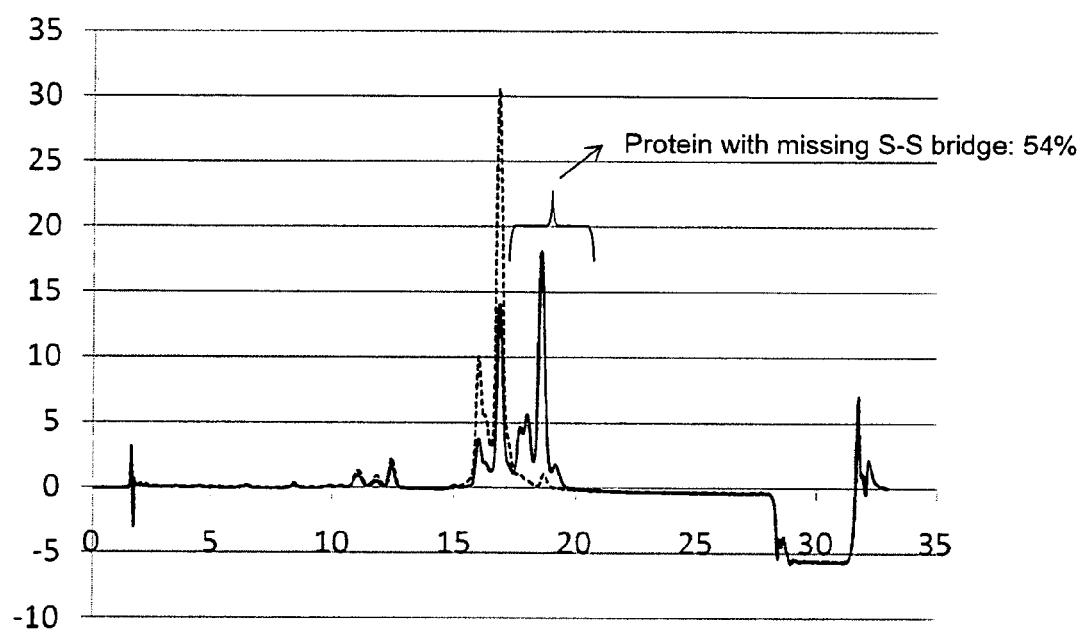
FIGS. 17A-17D: RP-HPLC analysis of a clarified culture broth sample after clean-up of Nanobodies B-1 (FIG. 17A), B-2 (FIG. 17C), B-3 (FIG. 17D) and B-4 (FIG. 17B) tested in 2 L scale fermentor, directly after harvest (full line) and after 4 hours incubation with $Cu^{2+}$ (10 µM $CuSO_4$) (dotted line).
Figure 17:
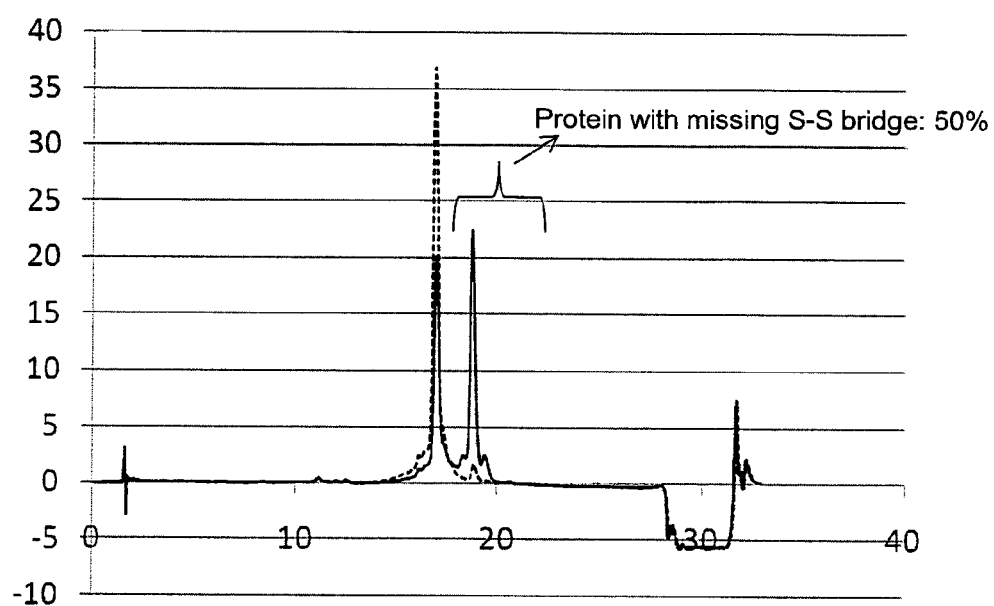
Figure 17:
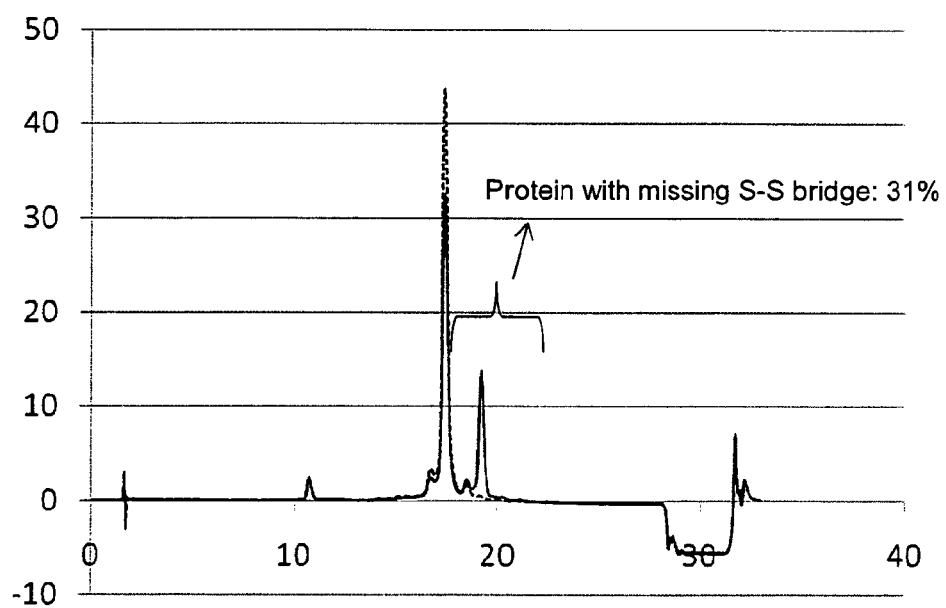
Figure 17:
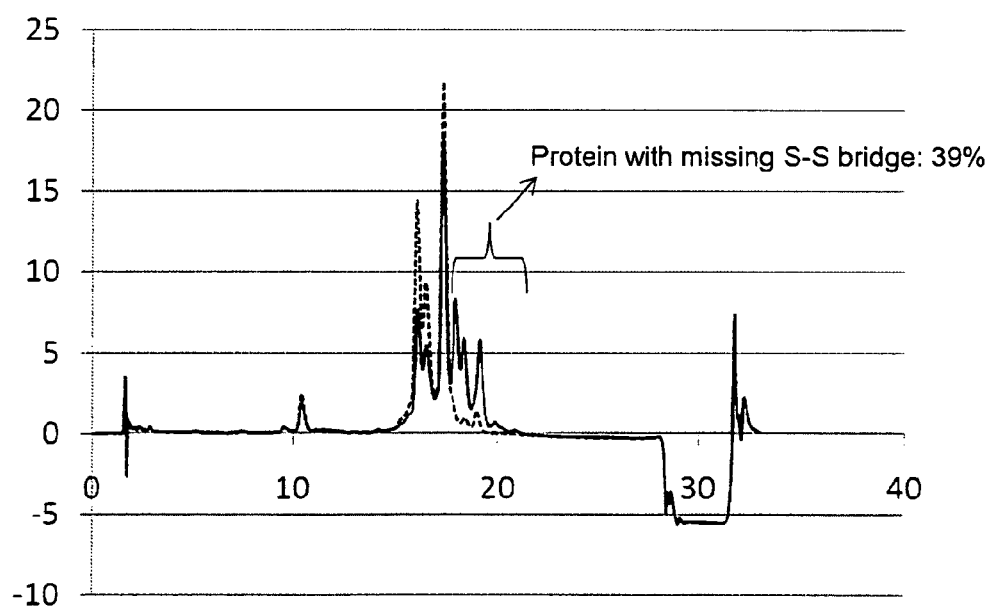

A trivalent Nanobody A-3 (DVQLVESGG-GLVQPGGSLRLSCAASGGSLSNYVLGWFRQAPG KEREFVAAINWRGDITIGPPNVEGRFTISRD-NAKNTGYLQMNSLRPEDTAVYYCGAGTPLNPGAY-IYD WSYDYWGQGTLVTVSSGGGGSGGGGSGGGG-SEVQLVESGGGLVQPGGSLRLSCAASGGSLSNYV LGWF RQAPGKEREFVAAINWRGDITIGPPNVEG-RFTISRDNAKNTGYLQMNSLRPED-TAVYYCGAGTPLNPG AYIYDWSYDYWGQGTLVTVSSGGGGSGGGGSG GGGSEVQLVESGGGLVQPGGSLRLSCAASGGSLSNY VLGWFRQAPGKEREFVAAINWRGDITIGPPNVEG-RFTISRDNAKNTGYLQMNSLRPEDTAVYYCGAGT PLNPGAYIYDWSYDYWGQGTLVTVSS; SEQ ID NO: 8) was expressed in *Pichia pastoris* using the standard conditions. An RP-HPLC analysis of a culture supernatant sample (after a clean up step) was analyzed on a C3 RP-HPLC column (conditions below) and on each peak the total mass was measured by ESI-Q-TOF-MS. In FIG. 16, four peaks can be identified, the first peak corresponds to the expected mass of the trivalent Nanobody, while each post peak that follows differs by 2 Da from the previous peak, thus representing a population of Nanobody with one, two or three subdomains in which the disulfide bond has not been formed.

Column: ZORBAX 300SB-C3
Column temperature: 80±1° C.
Mobile phase A: 0.05% TFA in 99.95% MilliQ
Mobile phase B: 0.05% TFA in 99.95% 1-propanol Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

Example 22

Observations of a Similar Variant in Nanobodies B-1, B-2, B-3 and B-4 Expressed in *Pichia pastoris*

Nanobodies B-1, B-2, B-3 and B-4 were also produced in *P. pastoris* strain X-33. Nanobodies B-1, B-2, B-3 and B-4 are trivalent Nanobodies that consist of three different single variable domains, having the following sequences:

Nanobody B-1
(SEQ ID NO: 9)
EVQLLESGGGLVQPGGSLRLSCAASGRTLSSYAMGWFRQAPGKGREFVA
RISQGGTAIYYADSVKGRFTISRDNSKNTVYLQMNSLRPEDTAVYYCAK
DPSPYYRGSAYLLSGSYDSWGQGTLVTVSSGGGGSGGGGSGGGGSEVQL
VESGGGLVQPGNSLRLSCAASGFTFSSFGMSWVRQAPGKGLEWVSSISG
SGSDTLYADSVKGRFTISRDNAKTTLYLQMNSLRPEDTAVYYCTIGGSL
SRSSQGTLVTVSSGGGGSGGGGSGGGGSEVQLLESGGGLVQPGGSLRLS
CAASGRIFSLPASGNIFNLLTIAWYRQAPGKGRELVATINSGSRTYYAD
SVKGRFTISRDNSKKTVYLQMNSLRPEDTAVYYCQTSGSGSPNFWGQGT
LVTVSS Nanobody B-2
(SEQ ID NO: 10)
EVQLLESGGGLVQPGGSLRLSCAASGRIFSLPASGNIFNLLTIAWYRQA
PGKGRELVATINSGSRTYYADSVKGRFTISRDNSKKTVYLQMNSLRPED
TAVYYCQTSGSGSPNFWGQGTLVTVSSGGGGSGGGSEVQLVESGGGLVQ
PGNSLRLSCAASGFTFSSFGMSWVRQAPGKGLEWVSSISGSGSDTLYAD
SVKGRFTISRDNAKTTLYLQMNSLRPEDTAVYYCTIGGSLSRSSQGTLV
TVSSGGGGSGGGSEVQLLESGGGLVQPGGSLRLSCAASGRTLSSYAMGW
FRQAPGKGREFVARISQGGTAIYYADSVKGRFTISRDNSKNTLYLQMNS
LRPEDTAVYYCAKDPSPYYRGSAYLLSGSYDSWGQGTLVTVSS Nanobody B-3
(SEQ ID NO: 11)
EVQLLESGGGLVQPGGSLRLSCAASGRIFSLPASGNIFNLLTIAWYRQA
PGKGRELVATINSGSRTYYADSVKGRFTISRDNSKKTVYLQMNSLRPED
TAVYYCQTSGSGSPNFWGQGTLVTVSSGGGGSGGGSEVQLVESGGGLVQ
PGNSLRLSCAASGFTFSSFGMSWVRQAPGKGLEWVSSISGSGSDTLYAD
SVKGRFTISRDNAKTTLYLQMNSLRPEDTAVYYCTIGGSLSRSSQGTLV
TVSSGGGGSGGGSEVQLLESGGGLVQPGGSLRLSCAASGRTLSSYAMGW
FRQAPGKGREFVARISQGGTAIYYADSVKGRFTISRDNSKNTVYLQMNS
LRPEDTAVYYCAKDPSPYYRGSAYLLSGSYDSWGQGTLVTVSS Nanobody B-4
(SEQ ID NO: 12)
EVQLLESGGGLVQPGGSLRLSCAASGRTLSSYAMGWFRQAPGKGREFVA
RISQGGTAIYYADSVKGRFTISRDNSKNTVYLQMNSLRPEDTAVYYCAK
DPSPYYRGSAYLLSGSYDSWGQGTLVTVSSGGGGSGGGGSGGGGSEVQL
VESGGGLVQPGNSLRLSCAASGFTFSSFGMSWVRQAPGKGLEWVSSISG
SGSDTLYADSVKGRFTISRDNAKTTLYLQMNSLRPEDTAVYYCTIGGSL
SRSSQGTLVTVSSGGGGSGGGGSGGGGSEVQLLESGGGLVQPGGSLRLS
CAASGRIFSLPASGNIFNLLTIAWYRQAPGKGRELVATIESGSRTYYAD
SVKGRFTISRDNSKKTVYLQMNSLRPEDTAVYYCQTSGSGSPNFWGQGT
LVTVSS The fermentation samples were analyzed by RP-HPLC analysis, after a sample clean up to check for product related variants. The chromatograms are shown in the FIGS. 17A-17D. In each of the constructs high amounts of variant with one missing disulfide bond were present: between 30 to 55% of the total load as estimated from the surface area on the RPC. The identity of this peak eluting approximately 2 min. after the correctly folded molecule (tR approx. 17 min in RP-HPLC) was confirmed by the fact that formation of the disulfide bridge could be induced by the addition of a low concentration of $Cu^{2+}$ to the culture supernatant. Chromatograms before and after $Cu^{2+}$ treatment show the disappearance of the significant post-peak into main peak (compare the full line with the dotted line).

Other peaks in the chromatogram might correspond to other product related variants such as pyro-glutamate formation at the N-terminus or minor impurities not removed by the partial clean up of the sample.

Example 23

Observations of a Similar Variant in Nanobody B-5 Expressed in *Pichia pastoris*

Nanobody B-5 was also produced in *P. pastoris* strain X-33. Nanobody B-5 is a Nanobody that consists of three different single variable domains and has the following sequence (SEQ ID NO: 13:

EVQLLESGGGLVQPGGSLRLSCAASGRIFSLPASGNIFNLLTIAWYRQA
PGKGRELVATINSGSRTYYADSVKGRFTISRDNSKKTLYLQMNSLRPED
TAVYYCQTSGSGSPNFWGQGTLVTVSSGGGGSGGGSEVQLVESGGGLVQ

-continued

PGNSLRLSCAASGFTFSSFGMSWVRQAPGKGLEWVSSISGSGSDTLYAD

SVKGRFTISRDNAKTTLYLQMNSLRPEDTAVYYCTIGGSLSRSSQGTLV

TVSSGGGGSGGGSEVQLLESGGGLVQPGGSLRLSCAASGRTLSSYAMGW

FRQAPGKGREFVARISQGGTAIYYADSVKGRFTISRDNSKNTLYLQMNS

LRPEDTAVYYCAKDPSPYYRGSAYLLSGSYDSWGQGTLVTVSS

Figure 18:
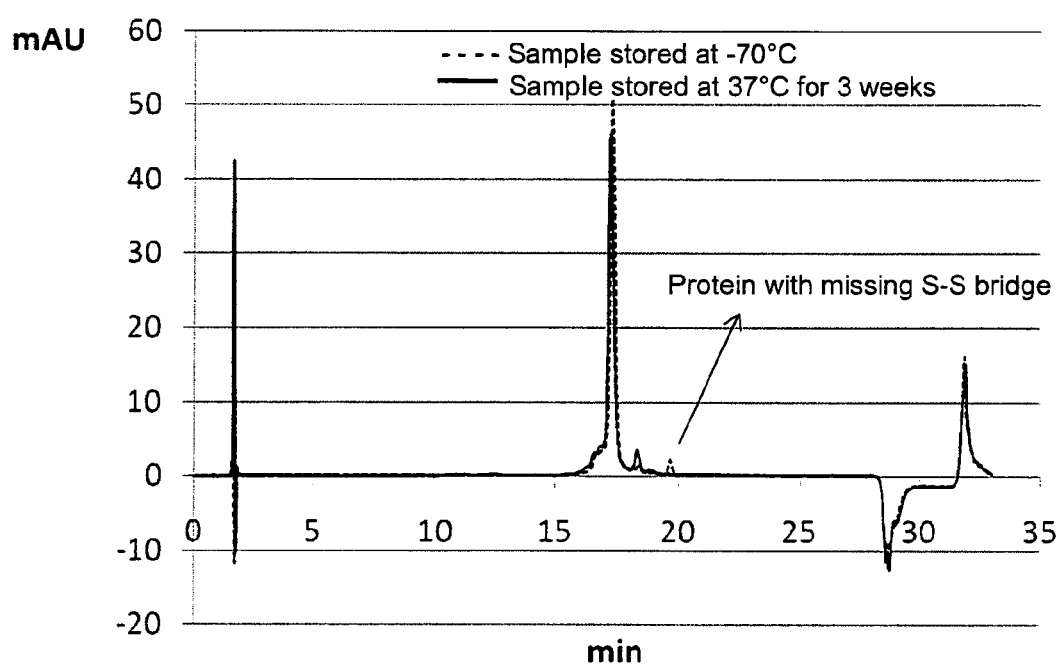
FIG. 18: RP-HPLC analysis of purified Nanobody B-5 stored at −70° C. (dotted line) and after 3 weeks storage at 37° C. (full line).

Nanobody B-5 was purified and analyzed by RP-HPLC. FIG. 18 shows an overlay chromatogram of the material stored at −70° C. (dotted line) compared to the same material after 3 weeks storage at 37° C. (full line). The post-peak eluting at approx. 20 min. in the chromatogram consisted of material with one missing disulphide bond, as identified by mass analysis (+2 Da) on an LC-Q-TOF. After 3 weeks of storage at 37° C., this peak reduced from 3.1% (at t=0, or storage at −70° C.) to only 0.2%, due to spontaneous oxidation to the correct disulphide bridge.

Summary of the Experiments

From all experiments taken together, the following general teaching can be derived: Upon expression in non-*E. coli* hosts, such as *P. pastoris* or *S. cerevisiae*, a subpopulation of the different Nanobodies, e.g. the RANKL008a, Nanobody A-1, Nanobody A-2, Nanobody A-3, and Nanobodies B-1, B-2, B-3, B-4 and B-5 is observed. This subpopulation represents a variant that lacks the canonical disulfide bridge in at least one of its subdomains (in case of a multimeric construct), or the single antigen binding domain (in case of a single domain antibody). In the case of RANKL008a a disulfide bridge was found missing in one or two of its anti-RANKL subdomains. Similar observations were observed for other Nanobodies also expressed in *P. pastoris*. If RANKL008a is expressed in *E. coli* this variant has never been observed.

RP-HPLC analysis detects the disulfide-lacking variant as a post peak in the chromatogram eluting at about +2 minutes from the main peak, LC-MS analysis demonstrates that this peak contains a mass compatible with the expected theoretical mass +2 Da, consistent with the addition of two hydrogens. Direct measurement of free thiols in the RANKL008a—which upon proper folding does not contain any free thiols—shows that free thiols can be measured in the sample and in a quantity that can be correlated with % of variant as estimated from the RP-HPLC. The variant is removed by affinity binding to a thiol-Sepharose column under denaturing conditions.

Similar product related variants have been observed for Nanobodies A-1, A-2, A-3, B-1, B-2, B-3, B-4 and B-5.

Surprisingly, the yield and potency—both for RANKL inhibition and binding and HSA binding—is unaffected by the disulfide variant suggesting that the structural integrity of the Nanobody is unaffected by the missing disulfide bond.

Classical refolding strategies under denaturing conditions in the presence of a redox couple can remove the variant; however during this process a small proportion of the RANKL008a does not form an intra-molecular disulfide bond but rather an inter-molecular disulfide bond and thus the formation of a dimer. Such dimer and potentially higher order oligomeric side products are undesirable in any pharmaceutical and will make the purification process more complex.

The free thiols can also be brought to form the desired disulfide bride by the oxygen present in the solution and this is enhanced by oxygenation, increasing pH, increasing temperature and/or high pressure. However the formation of the disulfide bond under some of these conditions is fairly slow and may also be accompanied by protein loss. Moreover the higher pH and temperatures can potentially induce the formation of other variants (pyroglutamate formation at the N-terminus is enhanced).

Addition of oxidizing metal ions, exemplified by $Cu^{2+}$, $Fe^{2+}$ and $Zn^{2+}$ caused formation of the desired disulfide bridge. In particular $Cu^{2+}$ resulted in a very efficient formation of the disulfide bond in the variant, at relatively low concentrations of this catalyst and proved applicable both on purified materials and in more crude samples (culture broth or crudely purified product). Use of $Cu^{2+}$ has previously been reported for the recombinant expression of IL-2 and β-IFN (U.S. Pat. No. 4,572,798). After removal of the $Cu^{2+}$ from the mixture the disulfide bond remains intact. Moreover this procedure does not affect the potency, nor does it induce undesired by products or variants as evidenced both by LC-MS analysis and RP-HPLC analysis.

Hence, the addition of oxidizing metal ions represents a preferred embodiment of the present invention.

ABBREVIATIONS

13H5 Humanized monovalent building block of RANKL008aa binding to RANKL
9GS 9AA glycine serine linker joining the Nanobody building blocks
ALB8 Humanized monovalent building block of RANKL008aa binding to HSA
ACN Acetonitrile
° C. degrees Celsius
D-PBS Dulbecco's Phosphate Buffered Saline
ELISA Enzyme linked immunosorbent assay
F/T Freeze thaw
GdnHCl Guanidinium hydrochloride
GuHCl Guanidine hydrochloride (GdnHCl)
HSA Human Serum Albumin
HPLC High Pressure Liquid Chromatography
IEX-HPLC Ion exchange HPLC (in this case cation-exchange)
PBS Phosphate Buffered Saline
mAU milli Absorption Units
LC-MS Liquid Chromatography coupled to Mass Spectrometer
Min minute(s)
MW Molecular Weight
MS Mass Spectrometry
PCR Polymerase Chain reaction
PDI Protein Disulfide Isomerase
PRV or PRV-SS Product related variant of Nanobody missing one disulfide bond
RANKL Receptor activator of nuclear factor-kB (RANK) ligand
RP(C) Reversed Phase (Chromatography)
RP-HPLC Reversed Phase HPLC
RT Room Temperature
Sec seconds
SE(C)-HPLC Size Exclusion (Chromatography) HPLC
TIC Total Ion Current
TFA Trifluoro Acetic acid
TOF Time of Flight
w weeks The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All references disclosed herein are incorporated by reference, in particular for the teaching that is referenced hereinabove.

The invention claimed is:

1. A method for promoting the formation of an intramolecular disulfide bridge in a domain antibody produced in yeast by fermentation in a culture medium, said method comprising:

exposing the domain antibody to oxidizing conditions by adding oxidizing metal ions to the culture medium during the culturing of the yeast, to the culture medium during the production phase of the domain antibody, to the culture medium after fermentation, to a supernatant comprising the domain antibody after removal of the yeast, and/or to a partially or highly purified preparation comprising the domain antibody, wherein the oxidizing metal ions are added to a final concentration of 0.15 to 10 mM; and applying conditions that remove domain antibodies lacking at least one intramolecular disulfide bridge, wherein the conditions that remove domain antibodies lacking at least one intramolecular disulfide bridge are selected from:

a) binding domain antibodies comprising free thiol groups to suitable reactive groups, including but not limited to immobilized thiol groups; and b) reverse phase high performance chromatography.

2. The method of claim 1, wherein the oxidizing metal ions are added to a purified preparation comprising the domain antibody.

3. The method according to claim 1, further comprising:

a) enhancing expression of a thiol isomerase in the yeast;

b) adapting the culturing conditions by one or more selected from the following: lowering culturing temperature and/or optimizing the culturing medium, by reduction of methanol feed for yeast requiring a methanol feed, lowering conductivity of the culture medium, addition of yeast extract and/or peptone, and any combination thereof;

c) refolding the domain antibody in the presence of a redox-buffer;

d) treating the domain antibody by oxygenation, increasing temperature, increasing pH, or high pressure, or any combination thereof; or e) combinations of any of a) through d).

4. The method according to claim 3, wherein the domain antibody is attached to a stationary phase of a chromatographic column.

5. The method according to claim 1, wherein said yeast is Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, or Endomycopsis.

6. The method according to claim 1, wherein the domain antibody is a light chain variable domain sequence or a heavy chain variable domain sequence.

7. The method according to claim 6, wherein the domain antibody is a heavy chain variable domain sequence that is derived from a conventional four-chain antibody or that essentially consists of a heavy chain variable domain sequence that is derived from a heavy chain antibody.

8. The method according to claim 7, wherein the domain antibody is a single domain antibody, a dAb or a Nanobody, or a VHH sequence.

9. The method of claim 1, wherein the oxidizing metal ions comprise $Cu^{2+}$, $Fe^{2+}$, $Fe^{3+}$, $Zn^{2+}$, or a combination thereof.

10. A method for promoting the formation of an intramolecular disulfide bridge in a domain antibody produced in yeast by fermentation in a culture medium, said method comprising exposing the domain antibody to oxidizing conditions by: adding oxidizing metal ions to the culture medium during the culturing of the yeast, to the culture medium during the production phase of the domain antibody, to the culture medium after fermentation, and/or to a supernatant comprising the domain antibody after removal of the yeast, wherein the oxidizing metal ions are added to a final concentration of 0.15 to 10 mM; and/or adding oxidizing metal ions to a partially or highly purified preparation comprising the domain antibody;
wherein the method further comprises:
 a) enhancing expression of a thiol isomerase in the yeast, wherein the thiol isomerase is selected from protein disulfide isomerase (PDI), calsequestrin, ERp72, ERp57, ERp60, ERp44, ERp5, ERp27 and PDIR;
 b) adapting the culturing conditions by one or more selected from the following: lowering the culturing temperature by 5° C. as compared to the standard culturing temperature for the yeast; reducing the methanol feed by 30-80% as compared to the standard methanol feed for the yeast; lowering the conductivity of the culture medium by 30%-80% as compared to the standard medium for the yeast; adding yeast extract and/or peptone to the culture medium at a concentration in the feed of 0-20%; and any combination thereof;
 c) refolding the domain antibody in the presence of a denaturant and a redox-buffer using 2M guanidinium hydrochloride and 1:5 mM/mM cystamine/cysteamine;
 d) treating the domain antibody by increasing the temperature to 40-60° C., increasing pH to pH 8-9, and/or applying high pressure to 250-5000 bar; or
 e) combinations of any of a) through d).

11. The method according to claim 10, comprising enhancing expression of a thiol isomerase in the yeast, wherein said thiol isomerase is selected from protein disulphide isomerase (PDI), calsequestrin, ERp72, ERp57, ERp60, ERp44, ERp5, ERp27 and PDIR.

12. The method according to claim 10, comprising lowering the culturing temperature by 5° C. as compared to the standard culturing temperature for the yeast.

13. The method according to claim 10, comprising reducing the methanol feed by 30-80% as compared to the standard methanol feed for the yeast.

14. The method according to claim 10, comprising lowering the conductivity of the culture medium by 30%-80% as compared to the standard medium for the yeast.

15. The method according to claim 10, comprising adding yeast extract and/or peptone to the culture medium at a concentration in the feed of 0-20%.

16. The method according to claim 10, comprising refolding the domain antibody in the presence of a denaturant and a redox-buffer using 2M guanidinium hydrochloride and 1:5 mM/mM cystamine/cysteamine.

17. The method according to claim 10, comprising treating the domain antibody by increasing the temperature to 40-60° C., increasing pH to pH 8-9, and/or applying high pressure to 250-5000 bar.

\* \* \* \* \*